US011988661B2

(12) United States Patent
Beekman et al.

(10) Patent No.: US 11,988,661 B2
(45) Date of Patent: May 21, 2024

(54) RAPID QUANTITATIVE TEST TO DIAGNOSE POLYCYSTIC KIDNEY DISEASE

(71) Applicants: UMC Utrecht Holding, B.V., Utrecht (NL); Koninklijke Nederlandse Akademie van Wetenschappen, Utrecht (NL)

(72) Inventors: Jeffrey Matthijn Beekman, Utrecht (NL); Johanna Florentia Dekkers, Utrecht (NL); Cornelis Korstiaan Van Der Ent, Utrecht (NL); Johannes Carolus Clevers, Utrecht (NL)

(73) Assignees: UMC Utrecht Holding, B.V., Utrecht (NL); Koninklijke Nederlandse Akademie van Wetenschappen, Utrecht (NL)

( * ) Notice: Subject to any disclaimer, the term of this patent is extended or adjusted under 35 U.S.C. 154(b) by 0 days.

(21) Appl. No.: 17/314,557

(22) Filed: May 7, 2021

(65) Prior Publication Data

US 2021/0333266 A1  Oct. 28, 2021

Related U.S. Application Data

(60) Division of application No. 16/003,293, filed on Jun. 8, 2018, now Pat. No. 11,035,852, which is a continuation of application No. 14/367,061, filed as application No. PCT/IB2012/057497 on Dec. 19, 2012, now Pat. No. 10,006,904.

(60) Provisional application No. 61/579,661, filed on Dec. 23, 2011, provisional application No. 61/577,110, filed on Dec. 19, 2011.

(51) Int. Cl.
G01N 33/50 (2006.01)

(52) U.S. Cl.
CPC ..... *G01N 33/5082* (2013.01); *G01N 33/5026* (2013.01); *G01N 2500/10* (2013.01); *G01N 2800/26* (2013.01); *G01N 2800/347* (2013.01); *G01N 2800/382* (2013.01); *G01N 2800/52* (2013.01)

(58) Field of Classification Search
None
See application file for complete search history.

(56) References Cited

U.S. PATENT DOCUMENTS

| | | |
|---|---|---|
| 8,642,339 B2 | 2/2014 | Sato et al. |
| 8,906,631 B2 | 12/2014 | Clevers et al. |
| 9,752,124 B2 | 9/2017 | Sato et al. |
| 9,765,301 B2 | 9/2017 | Ortega et al. |
| 9,833,496 B2 | 12/2017 | Clevers et al. |
| 10,006,904 B2 | 6/2018 | Beekman et al. |
| 10,597,633 B2 | 3/2020 | Ortega et al. |
| 10,940,180 B2 | 3/2021 | Clevers et al. |
| 10,947,510 B2 | 3/2021 | Sato et al. |
| 10,961,511 B2 | 3/2021 | Sachs et al. |
| 11,034,935 B2 | 6/2021 | Ortega et al. |
| 11,035,852 B2 | 6/2021 | Beekman et al. |
| 11,591,572 B2 | 2/2023 | Clevers et al. |
| 2012/0196312 A1 | 8/2012 | Sato et al. |
| 2013/0189327 A1 | 7/2013 | Ortega et al. |
| 2014/0044713 A1 | 2/2014 | De Lau et al. |
| 2014/0243227 A1 | 8/2014 | Clevers et al. |
| 2014/0256037 A1 | 9/2014 | Sato et al. |
| 2017/0275592 A1 | 9/2017 | Sachs et al. |
| 2018/0066233 A1 | 3/2018 | Huch Ortega et al. |
| 2018/0072995 A1 | 3/2018 | Sato et al. |
| 2018/0221441 A1 | 8/2018 | Clevers et al. |
| 2019/0100728 A1 | 4/2019 | Sato et al. |
| 2020/0172861 A1 | 4/2020 | Ortega et al. |
| 2020/0318063 A1 | 10/2020 | Ortega et al. |
| 2021/0040454 A1 | 2/2021 | Clevers et al. |
| 2021/0047618 A1 | 2/2021 | Clevers et al. |
| 2021/0208131 A1 | 7/2021 | Kretzchmar et al. |

FOREIGN PATENT DOCUMENTS

| | | | | |
|---|---|---|---|---|
| WO | WO 00/75286 A2 | 12/2000 | | |
| WO | WO 2004/080972 A1 | 9/2004 | | |
| WO | WO 2004/111014 A1 | 12/2004 | | |
| WO | WO 2007021982 A2 | 2/2007 | | |
| WO | WO 2010/090513 A2 | 8/2010 | | |
| WO | WO 2012/168930 A2 | 12/2012 | | |
| WO | WO 2020/019023 | * | 1/2020 | ............. C12N 5/071 |

OTHER PUBLICATIONS

International Search Report and Written Opinion for PCT/IB2012/057497 dated Jun. 28, 2013.
International Preliminary Report on Patentability for PCT/IB2012/057497 dated Nov. 2, 2014.
[No Author Listed] CFTR Compound Program, 2011. Cystic Fibrosis Foundation Therapeutics, Inc. Appendix B: Chemical Compound Inventory Listing and Appendix C: References, pp. 4-11.
[No Author Listed] Definition of "assay". Collins English Dictionary. Sixth Edition, 2003.
[No Author Listed] Vertex Achieves Breakthrough In Treating Basic CF Defect. Spring 2008. Last accessed at <http://www.cff.org/ECommitment/2008_spring/science_news_and_foundation_notes/features/vertex_achieves_breakthrough.html> on Mar. 12, 2014.
[No Author Listed] Vertex Announces Positive Results for VX-770, an Oral Investigational Agent That Targets a Defective Protein Responsible for Cystic Fibrosis. Mar. 27, 2008. Last accessed at <http://investors.vrtx.com/releasedetail.cfm?ReleaseID=301749> on Mar. 12, 2014.

(Continued)

*Primary Examiner* — Christina M Borgeest
(74) *Attorney, Agent, or Firm* — Wolf, Greenfield & Sacks, P.C.

(57) ABSTRACT

The invention relates to an assay for diagnosing a disease or affliction that affects fluid uptake or secretion or for studying the effectiveness of one or more drugs for treating the disease or affliction, wherein the assay comprises measuring swelling of one or more organoids.

5 Claims, 51 Drawing Sheets

(56) References Cited

OTHER PUBLICATIONS

[No Author Listed] Vertex Pharmaceuticals Initiates Phase 2 Development for CFTR Corrector VX-809 in Patients with Cystic Fibrosis. Mar. 25, 2009. Last accessed at <http://investors.vrtx.com/releasedetail.cfm?ReleaseID=372811> on Mar. 12, 2014.
Barker et al., Tissue-resident adult stem cell populations of rapidly self-renewing organs. Cell Stem Cell. Dec. 3, 2010;7(6):656-70. doi:10.1016/j.stem.2010.11.016.
Beekman et al., Syntenin-mediated regulation of Sox4 proteasomal degradation modulates transcriptional output. Oncogene. May 24, 2012;31(21):2668-79. doi: 10.1038/onc.2011.445. Epub Oct. 10, 2011.
Caci et al., CFTR activation in human bronchial epithelial cells by novel benzoflavone and benzimidazolone compounds. Am J Physiol Lung Cell Mol Physiol. Jul. 2003;285(1):L180-8. Epub Mar. 21, 2003.
Chen et al., A new role for bicarbonate in mucus formation. Am J Physiol Lung Cell Mol Physiol. Oct. 2010;299(4):L542-9. doi:10.1152/ajplung.00180.2010. Epub Aug. 6, 2010.
Cheng et al., Defective intracellular transport and processing of CFTR is the molecular basis of most cystic fibrosis. Cell. Nov. 16, 1990;63(4):827-34.
Clancy et al., Personalized medicine in cystic fibrosis: dawning of a new era. Am J Respir Crit Care Med. Oct. 1, 2012;186(7):593-7. doi:10.1164/rccm.201204-0785PP. Epub Jun. 21, 2012.
Clancy et al., Results of a phase IIa study of VX-809, an investigational CFTR corrector compound, in subjects with cystic fibrosis homozygous for the F508del-CFTR mutation. Thorax. Jan. 2012;67(1):12-8. doi:10.1136/thoraxjnl-2011-200393. Epub Aug. 8, 2011.
Cunningham et al., cAMP-stimulated ion currents in Xenopus oocytes expressing CFTR cRNA. Am J Physiol. Mar. 1992;262(3 Pt 1):C783-8.
Currid et al., Chloride secretion in a morphologically differentiated human colonic cell line that expresses the epithelial Na+ channel. J Physiol. Feb. 15, 2004;555(Pt 1):241-50. Epub Dec. 12, 2003.
De Boeck et al., New clinical diagnostic procedures for cystic fibrosis in Europe. J Cyst Fibros. Jun. 2011;10 Suppl 2:S53-66. doi: 10.1016/S1569-1993(11)60009-X.
De Jonge et al., Ex vivo CF diagnosis by intestinal current measurements (ICM) in small aperture, circulating Ussing chambers. J Cyst Fibros. Aug. 2004;3 Suppl 2:159-63.
De Lau et al., Lgr5 homologues associate with Wnt receptors and mediate R-spondin signalling. Nature. Jul. 4, 2011;476(7360):293-7. doi: 10.1038/nature10337.
Dekkers et al., A functional CFTR assay using primary cystic fibrosis intestinal organoids. Nat Med. Jul. 2013; 19(7):939-45. doi: 10.1038/nm.3201. Epub Jun. 2, 2013.
Dekkers et al., Novel opportunities for CFTR-targeting drug development using organoids. Rare Diseases. 2013;1(1):e27112(1-6).
Dekkers et al., Characterizing responses to CFTR-modulating drugs using rectal organoids derived from subjects with cystic fibrosis. Science Transl Med. Jun. 22, 2016;8(344):344ra84(1-12).
Denning et al., Processing of mutant cystic fibrosis transmembrane conductance regulator is temperature-sensitive. Nature. Aug. 27, 1992;358(6389):761-4.
Devor et al., Pharmacological modulation of ion transport across wild-type and DeltaF508 CFTR-expressing human bronchial epithelia. Am J Physiol Cell Physiol. Aug. 2000;279(2):C461-79.
Field, Intestinal ion transport and the pathophysiology of diarrhea. J Clin Invest. Apr. 2003;111(7):931-43.
Flume et al., Ivacaftor in subjects with cystic fibrosis who are homozygous for the F508del-CFTR mutation. Chest. Sep. 2012;142(3):718-24.
French et al., A delta F508 mutation in mouse cystic fibrosis transmembrane conductance regulator results in a temperature-sensitive processing defect in vivo. J Clin Invest. Sep. 15, 1996;98(6):1304-12.
Geborek et al., Association between genotype and pulmonary phenotype in cystic fibrosis patients with severe mutations. J Cyst Fibros. May 2011;10(3):187-92. doi: 10.1016/j.jcf.2011.01.005. Epub Feb. 26, 2011.
Gee et al., Rescue of $\Delta$F508-CFTR trafficking via a GRASP-dependent unconventional secretion pathway. Cell. Sep. 2, 2011;146(5):746-60. doi: 10.1016/j.cell.2011.07.021.
Hermans et al., Identification of the L927P and delta L1260 mutations in the CFTR gene. Hum Mol Genet. Jul. 1994;3(7):1199-200.
Hirth et al., Discovery of 1,2,3,4-tetrahydroisoquinoline-3-carboxylic acid diamides that increase CFTR mediated chloride transport. Bioorg Med Chem Lett. Apr. 15, 2005;15(8):2087-91.
Kerem et al., Identification of mutations in regions corresponding to the two putative nucleotide (ATP)-binding folds of the cystic fibrosis gene. Proc Natl Acad Sci U S A. Nov. 1990;87(21):8447-51.
Kerem et al., Identification of the cystic fibrosis gene: genetic analysis. Science. Sep. 8, 1989;245(4922):1073-80.
Korinek et al., Constitutive transcriptional activation by a beta-catenin-Tcf complex in APC-/-colon carcinoma. Science. Mar. 21, 1997;275(5307):1784-7.
Li et al., Impact of the cystic fibrosis mutation F508del-CFTR on renal cyst formation and growth. Am J Physiol Renal Physiol. Oct. 15, 2012;303(8):F1176-86. doi: 10.1152/ajprenal.00130.2012. Epub Aug. 8, 2012.
Liu et al., Functional Cftr in crypt epithelium of organotypic enteroid cultures from murine small intestine. Am J Physiol Cell Physiol. May 15, 2012;302(10):C1492-503. doi: 10.1152/ajpcell.00392.2011. Epub Mar. 7, 2012.
Loo et al., Rescue of DeltaF508 and other misprocessed CFTR mutants by a novel quinazoline compound. Mol Pharm. Sep.-Oct. 2005;2(5):407-13.
Loo et al., The chemical chaperone CFcor-325 repairs folding defects in the transmembrane domains of CFTR-processing mutants. Biochem J. May 1, 2006;395(3):537-42.
Luo et al., Trafficking of immature DeltaF508-CFTR to the plasma membrane and its detection by biotinylation. Biochem J. Apr. 1, 2009;419(1):211-9, 2 p following 219. doi:10.1042/BJ20081869.
Ma et al., High-affinity activators of cystic fibrosis transmembrane conductance regulator (CFTR) chloride conductance identified by high-throughput screening. J Biol Chem. Oct. 4, 2002;277(40):37235-41. Epub Aug. 2, 2002.
Ma et al., Thiazolidinone CFTR inhibitor identified by high-throughput screening blocks cholera toxin-induced intestinal fluid secretion. J Clin Invest. Dec. 2002;110(11):1651-8.
Macia et al., Dynasore, a cell-permeable inhibitor of dynamin. Dev Cell. Jun. 2006;10(6):839-50.
Mall et al., Defective cholinergic Cl(-) secretion and detection of K(+) secretion in rectal biopsies from cystic fibrosis patients. Am J Physiol Gastrointest Liver Physiol. Apr. 2000;278(4):G617-24.
Muanprasat et al., Discovery of glycine hydrazide pore-occluding CFTR inhibitors: mechanism, structure-activity analysis, and in vivo efficacy. J Gen Physiol. Aug. 2004;124(2):125-37.
Nakanishi et al. Role of CFTR in autosomal recessive polycystic kidney disease. J Am Soc Nephrol. Apr. 2001;12(4):719-725.
Ootani et al., Sustained in vitro intestinal epithelial culture within a Wnt-dependent stem cell niche. Nat Med. 2009;15(6):701-6; pp. 1-14 of author manuscript.
Oz et al., Forskolin stimulates swelling-induced chloride current, not cardiac cystic fibrosis transmembrane-conductance regulator current, in human cardiac myocytes. Circ Res. Jun. 1995;76(6):1063-70.
Pedemonte et al., Phenylglycine and sulfonamide correctors of defective delta F508 and G551D cystic fibrosis transmembrane conductance regulator chloride-channel gating. Mol Pharmacol. May 2005;67(5):1797-807. Epub Feb. 18, 2005.
Pedemonte et al., Small-molecule correctors of defective DeltaF508-CFTR cellular processing identified by high-throughput screening. J Clin Invest. Sep. 2005;115(9):2564-71. Epub Aug. 25, 2005.
Rabeh et al., Correction of both NBD1 energetics and domain interface is required to restore $\Delta$F508 CFTR folding and function. Cell. Jan. 20, 2012;148(1-2):150-63. doi: 10.1016/j.cell.2011.11.024.

(56) References Cited

OTHER PUBLICATIONS

Ramsey et al., A CFTR potentiator in patients with cystic fibrosis and the G551D mutation. N Engl J Med. Nov. 3, 2011;365(18):1663-72. doi: 10.1056/NEJMoa1105185.
Ratcliff et al., Production of a severe cystic fibrosis mutation in mice by gene targeting. Nat Genet. May 1993;4(1):35-41.
Ratjen et al., Cystic fibrosis. Lancet. Feb. 22, 2003;361(9358):681-9.
Rennolds et al., Low temperature induces the delivery of mature and immature CFTR to the plasma membrane. Biochem Biophys Res Commun. Feb. 22, 2008;366(4):1025-9. Epub Dec. 26, 2007.
Riordan et al., Identification of the cystic fibrosis gene: cloning and characterization of complementary DNA. Science. Sep. 8, 1989;245(4922):1066-73. Erratum in: Science Sep. 29, 1989;245(4925):1437.
Riordan, CFTR function and prospects for therapy. Annu Rev Biochem. 2008;77:701-26. doi: 10.1146/annurev.biochem.75.103004.142532.
Robert et al., Structural analog of sildenafil identified as a novel corrector of the F508del-CFTR trafficking defect. Mol Pharmacol. Feb. 2008;73(2):478-89. Epub Nov. 1, 2007.
Robinton et al., The promise of induced pluripotent stem cells in research and therapy. Nature. Jan. 18, 2012;481(7381):295-305. doi:10.1038/nature10761.
Rommens et al., Identification of the cystic fibrosis gene: chromosome walking and jumping. Science. Sep. 8, 1989;245(4922):1059-65.
Roth et al., The K+ channel opener 1-EBIO potentiates residual function of mutant CFTR in rectal biopsies from cystic fibrosis patients. PLoS One. 2011;6(8):e24445. doi: 10.1371/journal.pone.0024445. Epub Aug. 31, 2011.
Routaboul et al., Discovery of alpha-aminoazaheterocycle-methylglyoxal adducts as a new class of high-affinity inhibitors of cystic fibrosis transmembrane conductance regulator chloride channels. J Pharmacol Exp Ther. Sep. 2007;322(3):1023-35. Epub Jun. 10, 2007.
Saini, Cystic fibrosis patients benefit from mini guts. Cell Stem Cell Oct. 6, 2016;19:1-3. http://dx.doi.org/10.1016/j.stem.2016.09.001.
Sammelson et al., 3-(2-Benzyloxyphenyl)isoxazoles and isoxazolines: synthesis and evaluation as CFTR activators. Bioorg Med Chem Lett. Aug. 4, 2003;13(15):2509-12.
Sato et al., Long-term expansion of epithelial organoids from human colon, adenoma, adenocarcinoma, and Barrett's epithelium. Gastroenterology. Nov. 2011;141(5):1762-72. doi: 10.1053/j.gastro.2011.07.050. Epub Sep. 2, 2011.
Sato et al., Paneth cells constitute the niche for Lgr5 stem cells in intestinal crypts. Nature. Jan. 20, 2011;469(7330):415-8. doi:10.1038/nature09637. Epub Nov. 28, 2010.
Sato et al., Single Lgr5 stem cells build crypt-villus structures in vitro without a mesenchymal niche. Nature. May 14, 2009;459(7244):262-5. doi: 10.1038/nature07935. Epub Mar. 29, 2009.
Sermet-Gaudelus et al., Ataluren (PTC124) induces cystic fibrosis transmembrane conductance regulator protein expression and activity in children with nonsense mutation cystic fibrosis. Am J Respir Crit Care Med. Nov. 15, 2010;182(10):1262-72. doi: 10.1164/rccm.201001-0137OC. Epub Jul. 9, 2010.
Singh et al., Transepithelial fluctuation analysis of chloride secretion. J Cyst Fibros. Aug. 2004;3 Suppl 2:127-32.
Smith et al., Fluid and electrolyte transport by cultured human airway epithelia. J Clin Invest. Apr. 1993;91(4):1590-7.
Sonawane et al., Alpha-aminoazaheterocyclic-methylglyoxal adducts do not inhibit cystic fibrosis transmembrane conductance regulator chloride channel activity. J Pharmacol Exp Ther. May 2008;325(2):529-35. doi: 10.1124/jpet.107.132357. Epub Feb. 13, 2008.
Sonawane et al., Thiazolidinone CFTR inhibitors with improved water solubility identified by structure-activity analysis. Bioorg Med Chem. Sep. 1, 2008;16(17):8187-95. doi: 10.1016/j.bmc.2008.07.044. Epub Jul. 23, 2008.

Springsteel et al., Benzoflavone activators of the cystic fibrosis transmembrane conductance regulator: towards a pharmacophore model for the nucleotide-binding domain. Bioorg Med Chem. Sep. 1, 2003;11(18):4113-20.
Strandvik et al., Spectrum of mutations in the CFTR gene of patients with classical and atypical forms of cystic fibrosis from southwestern Sweden: identification of 12 novel mutations. Genet Test. 2001 Fall;5(3):235-42.
Sullivan et al., Chloride and fluid secretion in polycystic kidney disease. J Am Soc Nephrol. May 1998;9(5):903-16.
Sullivan et al., Coupling of cell volume and membrane potential changes to fluid secretion in a model of renal cysts. Kidney Int. May 1994;45(5):1369-80.
Takezawa et al., Collagen vitrigel: A novel scaffold that can facilitate a three-dimensional culture for reconstructing organoids. Cell Transplantation. 2004;13:463-73.
Thiagarajah et al., A small molecule CFTR inhibitor produces cystic fibrosis-like submucosal gland fluid secretions in normal airways. Faseb J. May 2004;18(7):875-7. Epub Mar. 4, 2004.
Thiagarajah et al., CFTR inhibitors for treating diarrheal disease. Clin Pharmacol Ther. Sep. 2012;92(3):287-90. doi: 10.1038/clpt.2012.114. Epub Aug. 1, 2012.
Toczyłowska-Mamińska et al., Ion transporting proteins of human bronchial epithelium. J Cell Biochem. Feb. 2012;113(2):426-32. doi: 10.1002/jcb.23393.
Torres et al., Autosomal dominant polycystic kidney disease. Lancet. Apr. 14, 2007;369(9569):1287-301.
Tradtrantip et al., Nanomolar potency pyrimido-pyrrolo-quinoxalinedione CFTR inhibitor reduces cyst size in a polycystic kidney disease model. J Med Chem. Oct. 22, 2009;52(20):6447-55. doi:10.1021/jm9009873.
Van Goor et al., Correction of the F508del-CFTR protein processing defect in vitro by the investigational drug VX-809. Proc Natl Acad Sci U S A. Nov. 15, 2011;108(46):18843-8. doi: 10.1073/pnas.1105787108. Epub Oct. 5, 2011.
Van Goor et al., Rescue of CF airway epithelial cell function in vitro by a CFTR potentiator, VX-770. Proc Natl Acad Sci U S A. Nov. 3, 2009;106(44):18825-30. doi: 10.1073/pnas.0904709106. Epub Oct. 21, 2009.
Van Goor et al., Rescue of DeltaF508-CFTR trafficking and gating in human cystic fibrosis airway primary cultures by small molecules. Am J Physiol Lung Cell Mol Physiol. Jun. 2006;290(6):L1117-30. Epub Jan. 27, 2006.
Venkatasubramanian et al., Ion transport in the small intestine. Curr Opin Gastroenterol. Mar. 2010;26(2):123-8. doi: 10.1097/MOG.0b013e3283358a45.
Welch et al., PTC124 targets genetic disorders caused by nonsense mutations. Nature. May 3, 2007;447(7140):87-91. Epub Apr. 22, 2007.
Wilke et al., Mouse models of cystic fibrosis: phenotypic analysis and research applications. J Cyst Fibros. Jun. 2011;10 Suppl 2:S152-71. doi: 10.1016/S1569-1993(11)60020-9.
Wong et al., Directed differentiation of human pluripotent stem cells into mature airway epithelia expressing functional CFTR protein. Nat Biotechnol. Sep. 2012;30(9):876-82.
Yanda et al. A potential strategy for reducing cysts in autosomal dominant polycystic kidney disease with a CFTR corrector. J Biol Chem. Jul. 20, 2018;293(29):11513-11526. doi: 10.1074/jbc.RA118.001846. Epub Jun. 6, 2018.
Yang et al., Nanomolar affinity small molecule correctors of defective Delta F508-CFTR chloride channel gating. J Biol Chem. Sep. 12, 2003;278(37):35079-85. Epub Jun. 27, 2003.
Yang et al., Small-molecule CFTR inhibitors slow cyst growth in polycystic kidney disease. J Am Soc Nephrol. Jul. 2008;19(7):1300-10. doi: 10.1681/ASN.2007070828. Epub Apr. 2, 2008.
Yoo et al., 4'-Methyl-4,5'-bithiazole-based correctors of defective delta F508-CFTR cellular processing. Bioorg Med Chem Lett. Apr. 15, 2008;18(8):2610-4. doi:10.1016/j.bmcl.2008.03.037. Epub Mar. 16, 2008.
Zielenski, Genotype and phenotype in cystic fibrosis. Respiration. 2000;67(2):117-33.
Zimmerman, Lung organoid culture. Differentiation. 1987;36:256-109.

(56) References Cited

OTHER PUBLICATIONS

*U.S. Appl. No. 12/705,336, filed May 10, 2010, U.S. Pat. No. 8,906,631.
*U.S. Appl. No. 14/494,511, filed Sep. 23, 2014, U.S. Pat. No. 9,833,496.
*U.S. Appl. No. 15/813,863, filed Nov. 15, 2017, U.S. Pat. No. 10,940,180.
*U.S. Appl. No. 17/161,376, filed Jan. 28, 2021.
*U.S. Appl. No. 13/147,163, filed Sep. 14, 2011, U.S. Pat. No. 8,642,339.
*U.S. Appl. No. 14/079,545, filed Nov. 13, 2013, U.S. Pat. No. 10,947,510.
*U.S. Appl. No. 16/113,445, filed Aug. 27, 2018, 2019-0100728.
*U.S. Appl. No. 13/194,866, filed Jul. 29, 2011, U.S. Pat. No. 9,752,124.
*U.S. Appl. No. 15/654,243, filed Mar. 15, 2018, 2018-0072995.
*U.S. Appl. No. 13/812,614, filed Apr. 8, 2013, U.S. Pat. No. 9,765,301.
*U.S. Appl. No. 15/665,363, filed Jul. 31, 2017, U.S. Pat. No. 11,034,935.
*U.S. Appl. No. 17/191,650, filed Mar. 3, 2021.
*U.S. Appl. No. 14/124,884, filed May 9, 2014, 2014-0243227.
*U.S. Appl. No. 14/367,061, filed Jun. 19, 2014, U.S. Pat. No. 10,006,904.
*U.S. Appl. No. 16/003,293, filed Jun. 8, 2018, U.S. Pat. No. 11,035,852.
*U.S. Appl. No. 16/954,506, filed Jun. 16, 2020, 2021-0208131.
*U.S. Appl. No. 15/310,905, filed Nov. 14, 2016, U.S. Pat. No. 10,597,633.
*U.S. Appl. No. 16/743,191, filed Jun. 4, 2020, 2020-0172861.
*U.S. Appl. No. 16/906,515, filed Oct. 8, 2020, 2020-0318063.
*U.S. Appl. No. 15/529,346, filed May 24, 2017, 2017-0275592.
*U.S. Appl. No. 15/529,150, filed May 24, 2017, U.S. Pat. No. 10,961,511.
*U.S. Appl. No. 17/182,457, filed Feb. 23, 2021.
*U.S. Appl. No. 16/078,354, filed Aug. 21, 2018, 2021-0040454.
*U.S. Appl. No. 16/310,933, filed Dec. 18, 2018.
PCT/IB2012/057497, Jun. 28, 2013, International Search Report and Wirtten Opinion.
PCT/IB2012/057497, Nov. 2, 2014, International Preliminary Report on Patentability.

* cited by examiner

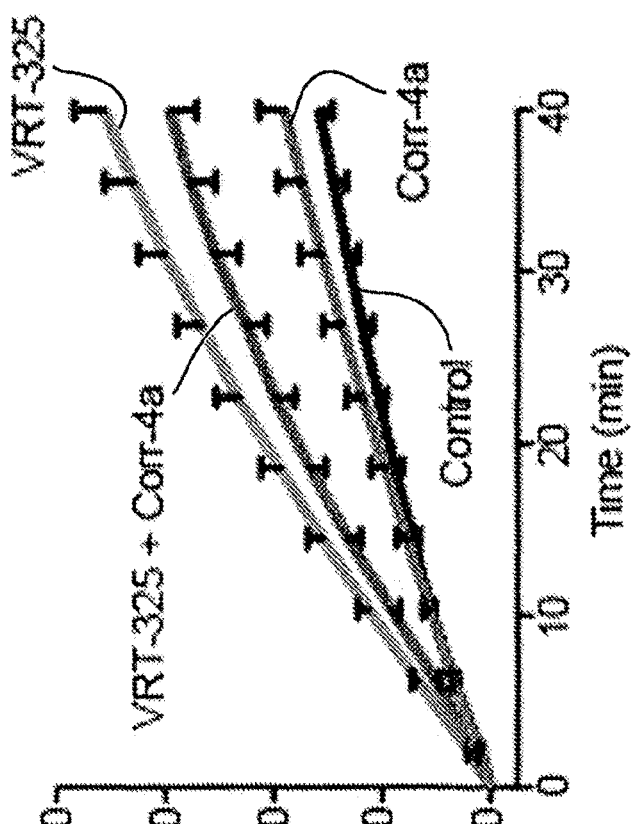
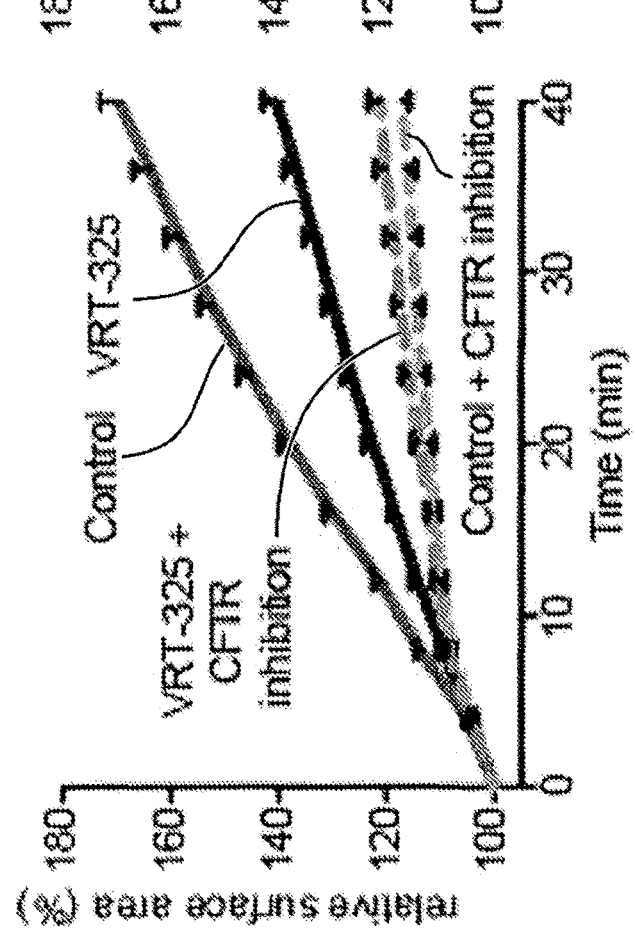
FIG. 6a
FIG. 6b

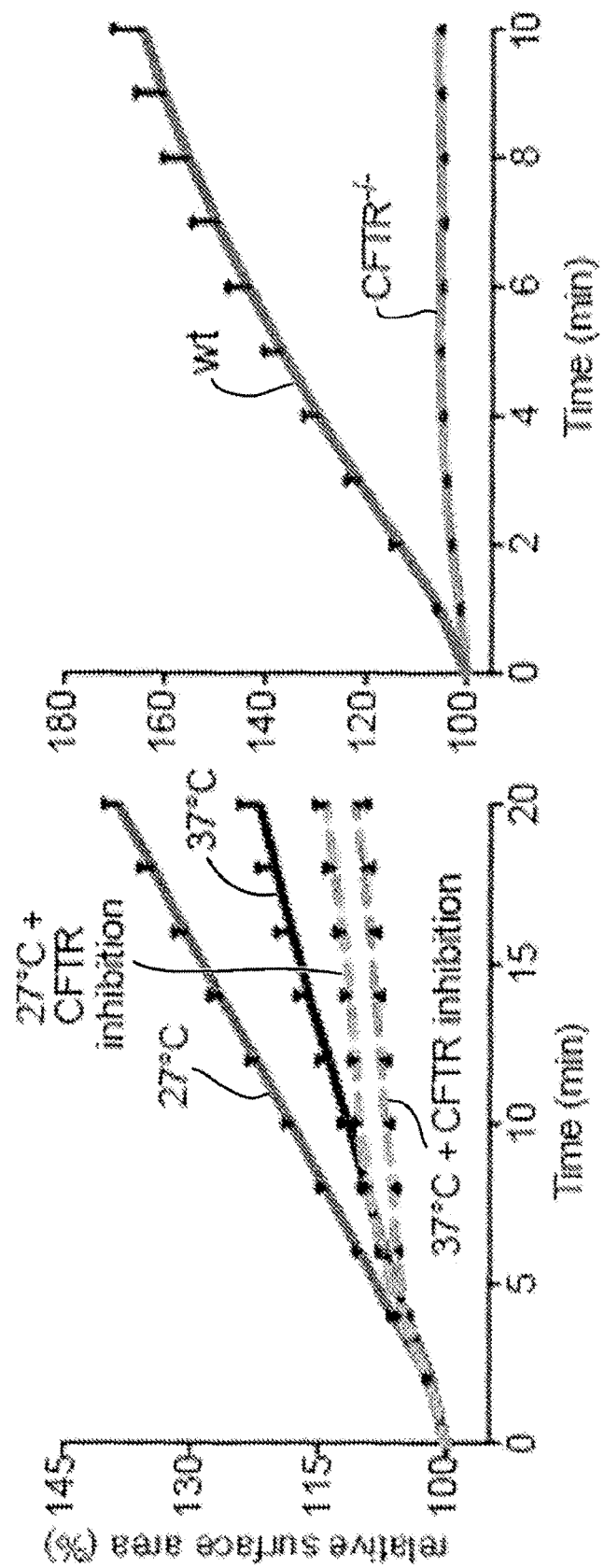

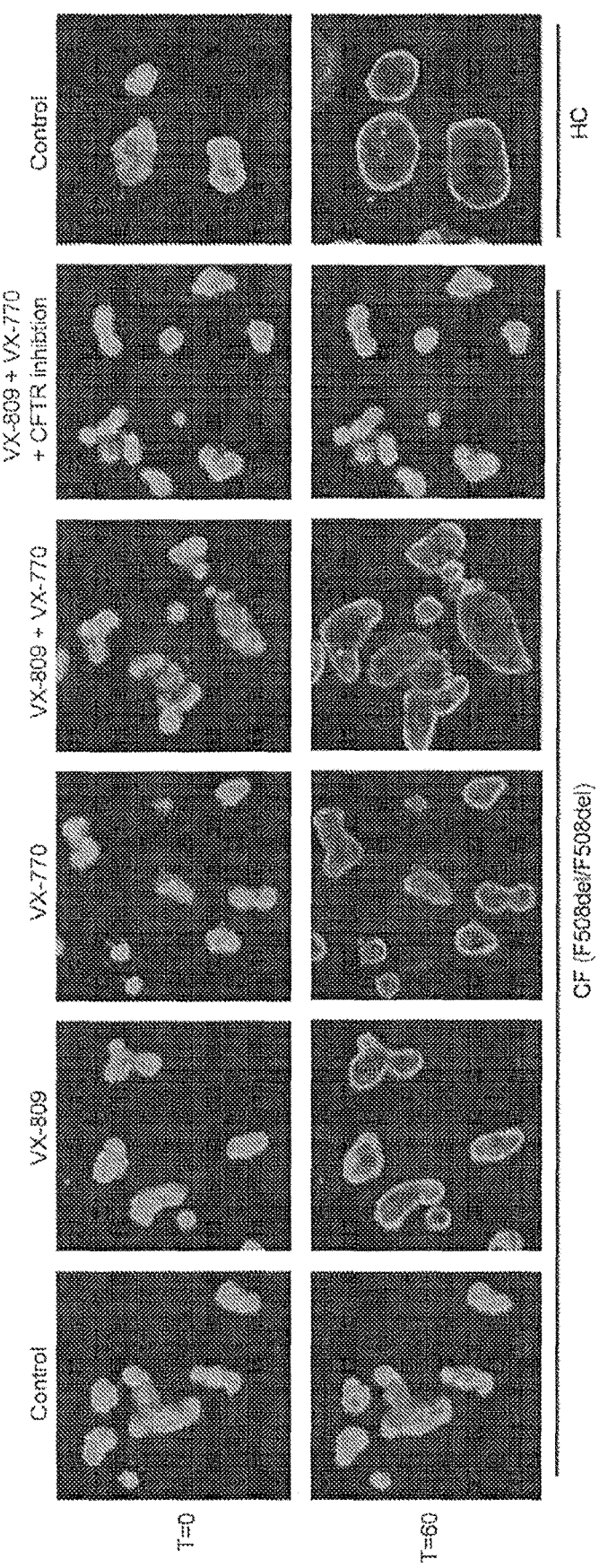

*FIG. 14c*
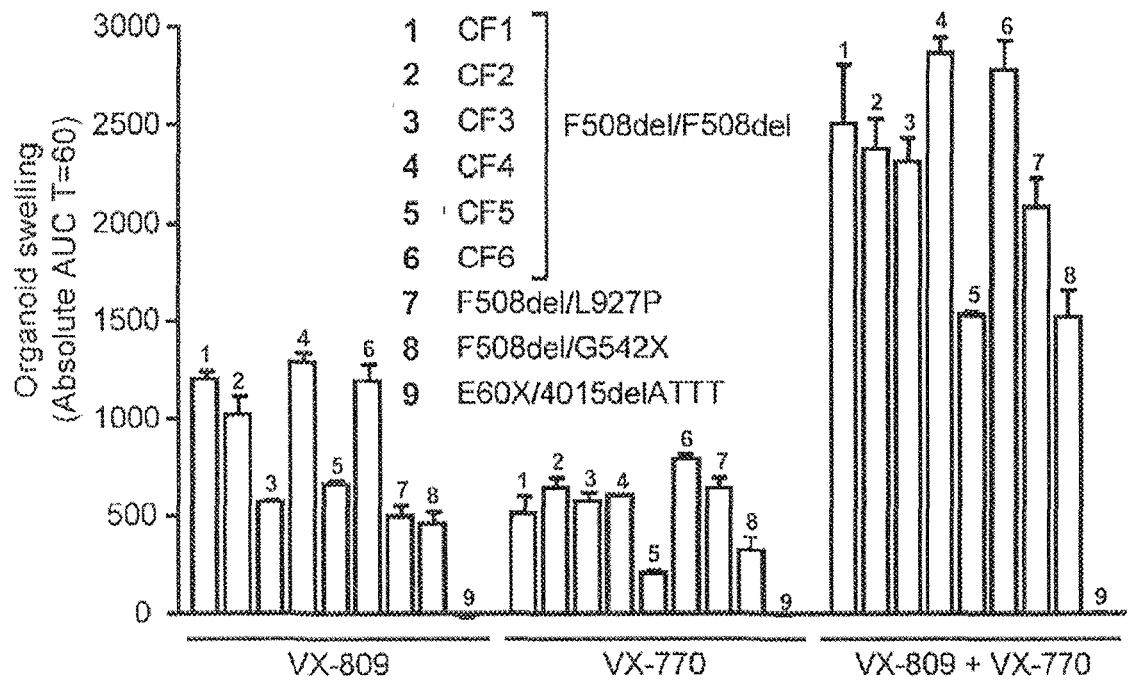
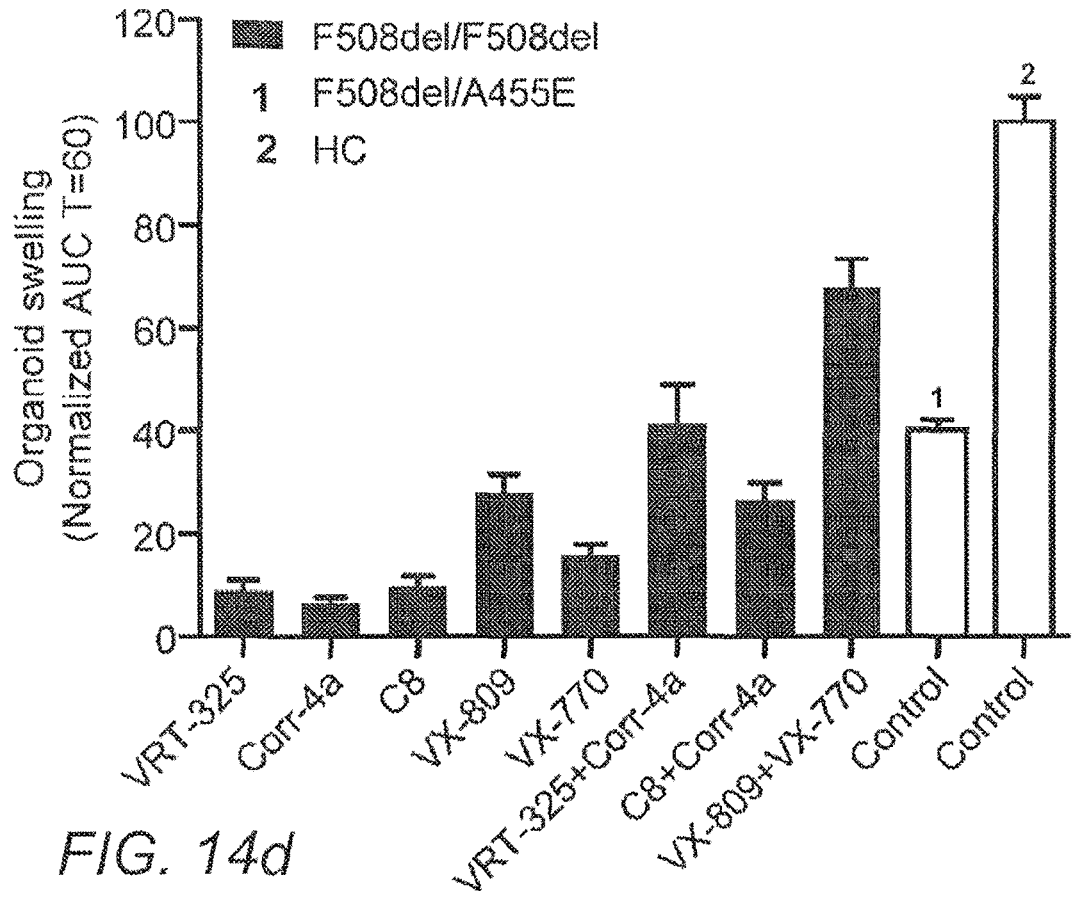
*FIG. 14d*

FIG. 15
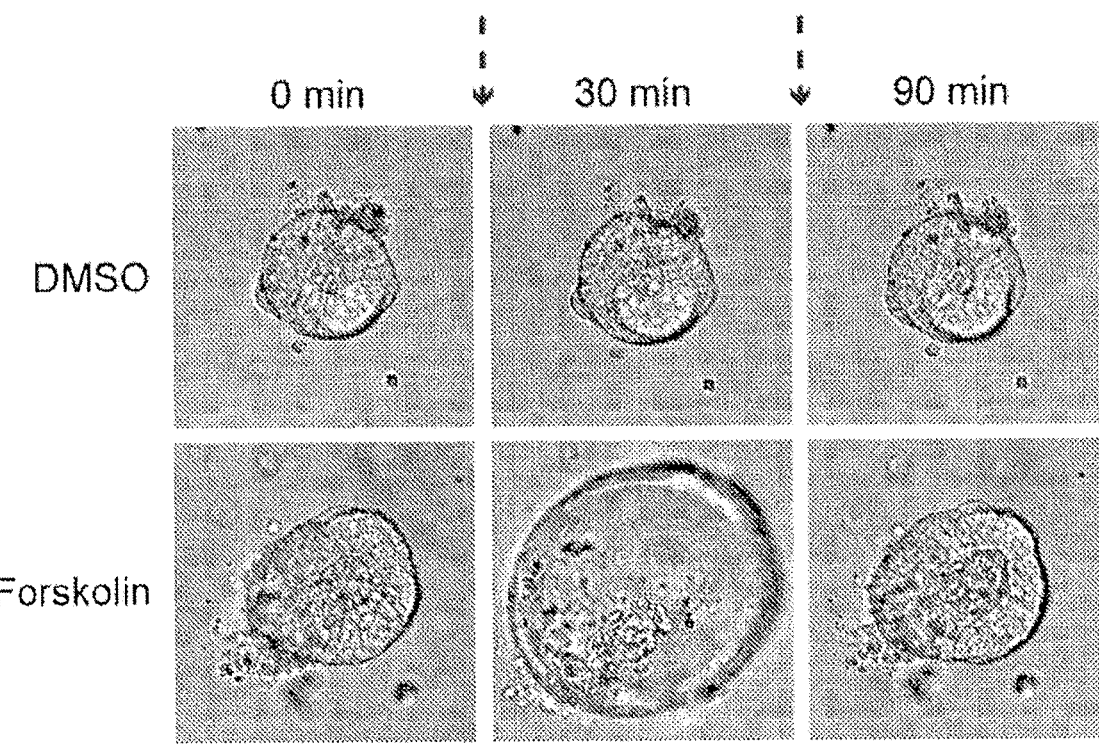
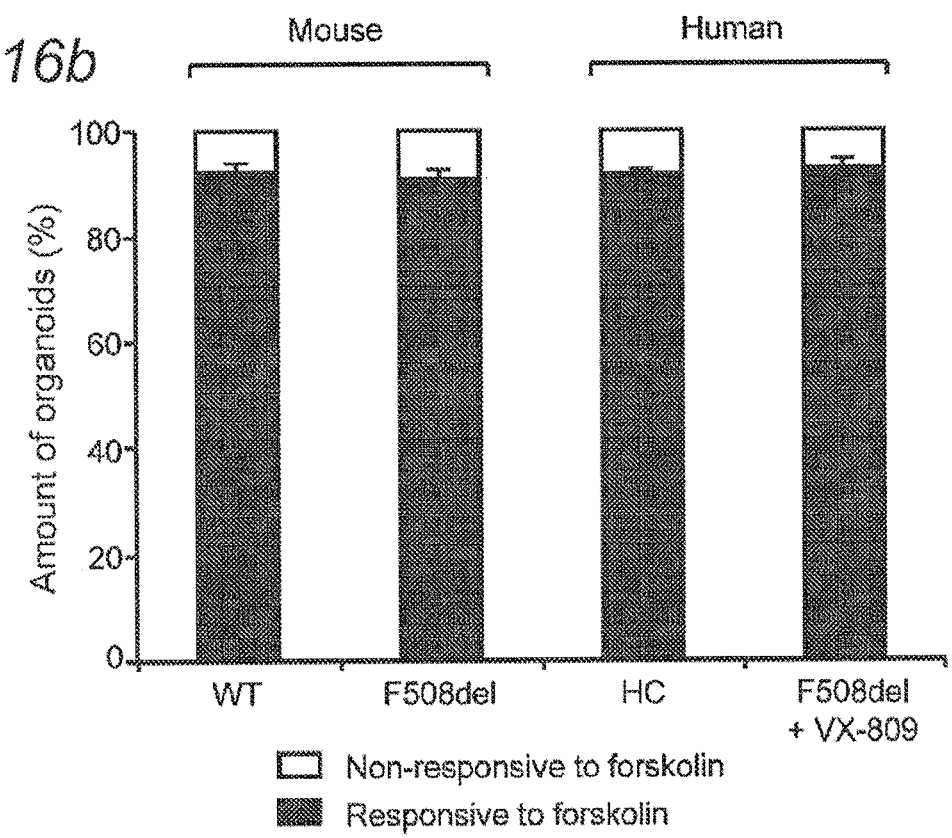
FIG. 16b

Non-responsive to forskolin

Responsive to forskolin

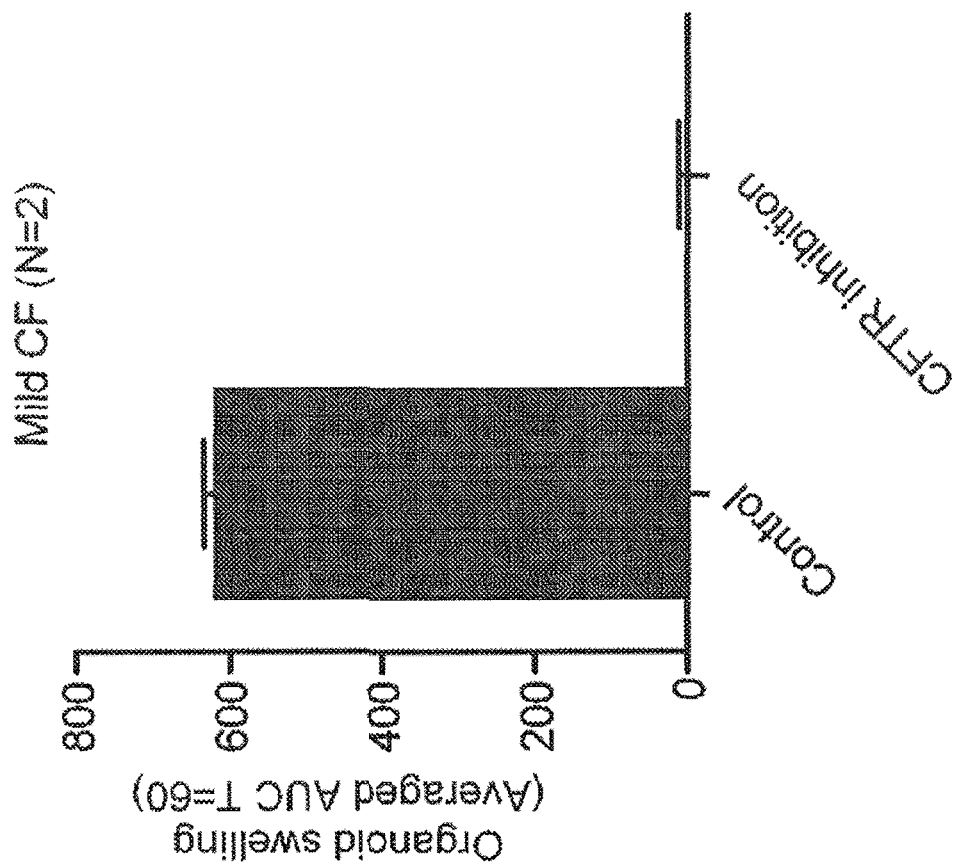
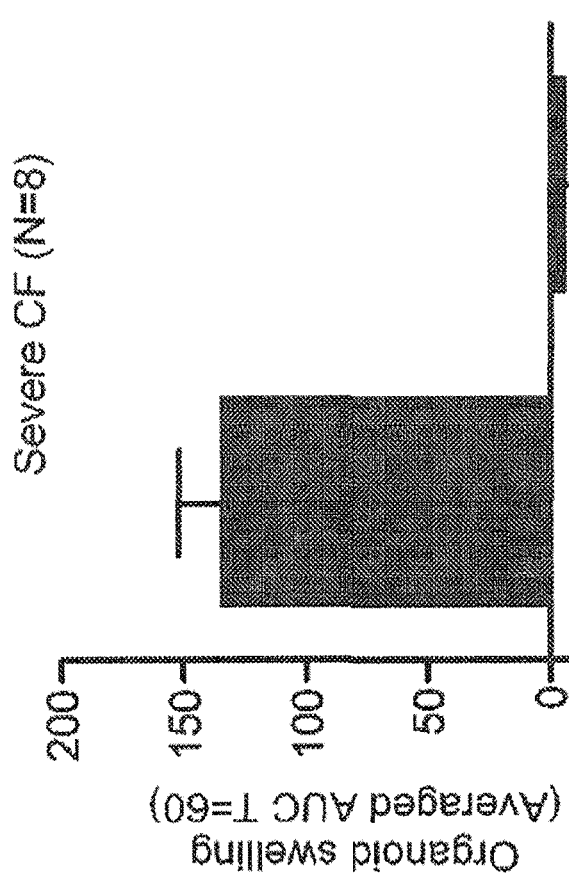
FIG. 19b
FIG. 19c

ICM tracing

| | Forskolin-induced swelling (AUC T=60) | SD | Forskolin-induced Cl⁻ secretion (µ Amp/cm²) | SD |
|---|---|---|---|---|
| E60X/4015delATTT | 2.63 | 4.56 | -5.1 | 3.9 |
| F508del/G542X | 32.49 | 30.65 | 0.5 | 0.8 |
| F508del/F508del | 60.52 | 4.75 | 7 | 3.1 |
| F508del/F508del | 149.93 | 49.52 | 5.3 | 1.7 |
| F508del/F508del | 98.21 | 21.45 | 7.9 | 3.2 |
| F508del/F508del | 164.14 | 20.54 | 9.1 | 4.4 |
| F508del/F508del | 179.33 | 23.90 | -10.1 | -3.7 |
| F508del/A455E | 1494.00 | 118.03 | 14.2 | 4.4 |
| F508del/A455E | 1343.33 | 81.29 | 17 | 4.7 |
| Healthy control | 3191.33 | 724.50 | 26.3 | 12.8 |
| Healthy control | 3755.00 | 762.86 | 57 | 18.2 |
| Healthy control | 3666.75 | 287.97 | 50.1 | 14.5 |

Ileal F508del/F508del organoids

Ileal F508del/F508del organoids

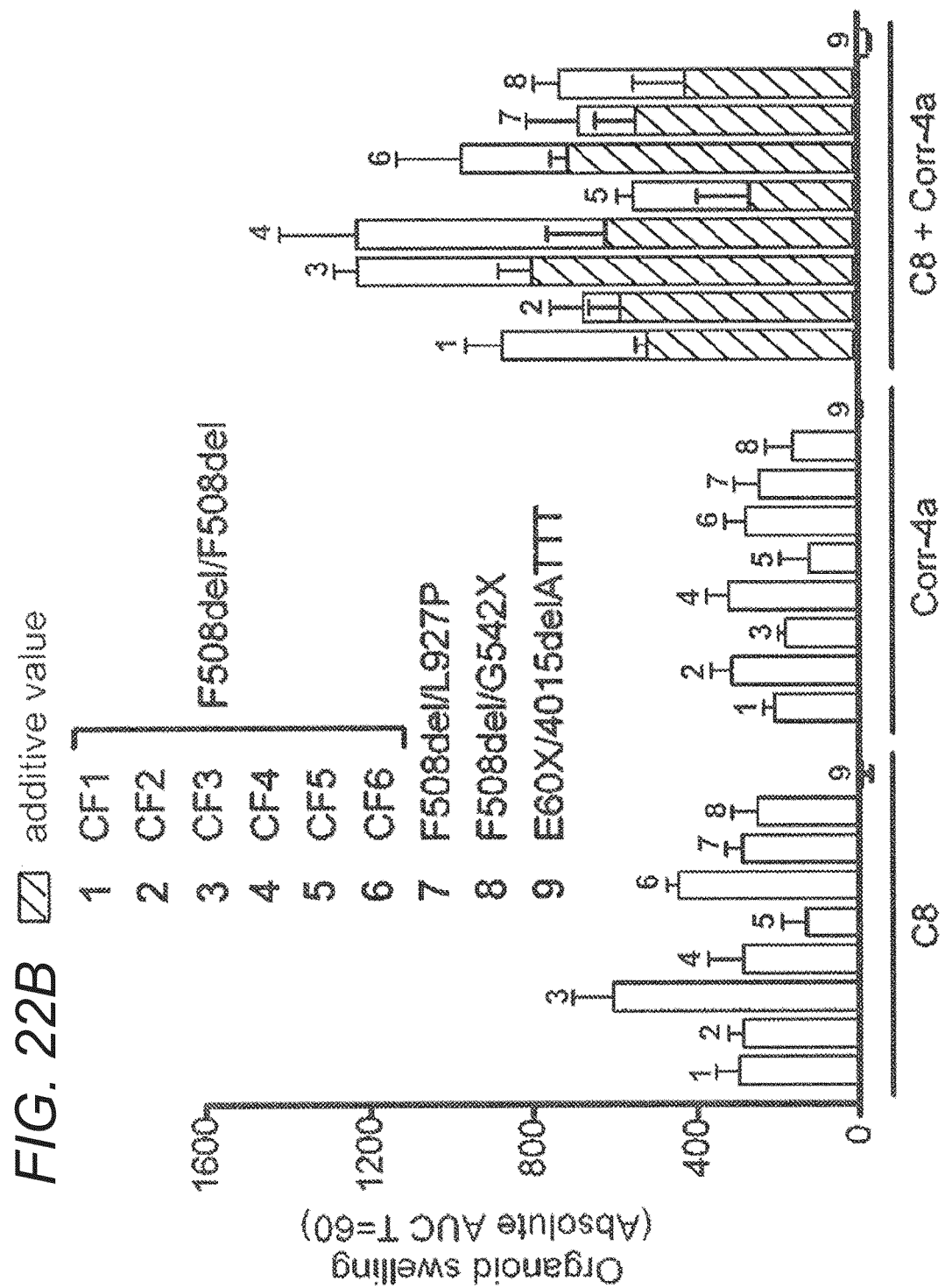

RAPID QUANTITATIVE TEST TO DIAGNOSE POLYCYSTIC KIDNEY DISEASE

RELATED APPLICATIONS

This application is a divisional of U.S. patent application Ser. No. 16/003,293, filed Jun. 8, 2018, which is a continuation of U.S. patent application Ser. No. 14/367,061, filed Jun. 19, 2014, which is a national stage filing under 35 U.S.C. § 371 of International Application No. PCT/IB2012/057497 filed Dec. 19, 2012, which was published under PCT Article 21(2) in English, and which claims the benefit of U.S. Provisional Patent Application Serial Nos. 61/577,110 filed Dec. 19, 2011, and 61/579,661 filed Dec. 23, 2011, the entire contents of each of which are incorporated by reference herein.

FIELD OF THE INVENTION

The invention relates to an assay for fluid and electrolyte homeostasis in an organoid-based culture method.

BACKGROUND

Cystic fibrosis transmembrane conductance regulator (CFTR) functions as an anion channel, and is essential for fluid and electrolyte homeostasis at epithelial surfaces of many organs, including lung and intestine. The autosomal-recessive disorder cystic fibrosis (CF) is caused by mutations of the CFTR gene. CF disease is highly variable, and patients have a median life expectancy of approximately 40 years. Loss-of-function mutations cause altered ion and fluid transport, which results in accumulation of viscous mucus in the pulmonary and gastrointestinal tract. This is associated with bacterial infections, aberrant inflammation and malnutrition. Over 1500 mutations have been described, but the most dominant mutation (~67% of total mutant alleles world-wide) is a deletion of phenylalanine at position 508 (CFTR-delF508). This causes misfolding, ER-retention and early degradation of the CFTR protein which prevents function at the plasma membrane. Other mutations in the CFTR gene that have been found in CF patients also impair protein folding or impair protein production, gating, conductance, splicing and/or interactions with other proteins.

Current therapy for CF is mainly symptomatic and focuses on reduction of bacterial pressure, inflammation, and normalization of nutrient uptake and physical growth. Recently, multiple compounds have been identified that target mutation-specific defects of the CFTR protein itself. Clinical trials are currently performed using compounds that induce i) premature stop codon readthrough, ii) correction of plasma membrane trafficking of CFTR (correctors), and iii) enhance CFTR gating (potentiators). Recently, a phase III clinical trial has successfully been completed for a potentiator in CF patients with a CFTR-G551D mutation, demonstrating that mutation-specific drug targeting is feasible in CF. Combinations of correctors and potentiators are currently assessed in a phase 11 trial for the dominant patient-group harboring the CFTR-delF508 mutation.

Although these recent developments are very promising, the level of functional restoration of CFTR by these drugs in in vitro model systems is still limited. In addition, patients show variable responses to these therapies due to yet undefined mechanisms. The inability to select these non-responding subgroups limits clinical efficacy and drug registration. Together, this indicates that development of new compounds and efficient screenings of drug efficacy at the level of individual patients, as well as the screening of large libraries to identify novel compounds are urgently needed. Thus far, there are no primary cell models available to screen for compounds that restore mutant CFTR function, only transformed cell lines have been used to identify compounds and their efficiency. An in vitro model which allows for the expansion and maintenance of primary human cells will allow the analysis of the drug response of individual patients and identify subgroups of responsive patients for each treatment. In addition, it will allow the screening of libraries of novel drugs for their effect on primary cells.

SUMMARY OF INVENTION

The invention provides an assay for diagnosing a disease or affliction that affects fluid uptake or secretion or for studying the effectiveness of one or more drugs for treating the disease or affliction, wherein the assay comprises measuring swelling of one or more organoids.

The term "assay" is intended to be equivalent to "method". Thus, the invention also provides a method for diagnosing a disease or affliction that affects fluid uptake or secretion or for studying the effectiveness of one or more drugs for treating the disease or affliction, wherein the method comprises measuring swelling of one or more organoids.

The invention provides a rapid and simple quantitative assay for CFTR (or other diseases or affliction that affect fluid uptake or secretion) function in a primary intestinal crypt-based culture method[15-17]. This culture method enables intestinal stem cells to expand into closed organoids containing crypt-like structures and an internal lumen lined by differentiated cells, recapitulating the in vivo tissue architecture. Intestinal CFTR is predominantly expressed at the apical membrane of the crypt cells where its activation drives secretion of electrolytes and fluids[18-20]. Forskolin[21] was found to induce rapid swelling of both human healthy control (HC) and murine wild-type organoids that completely depends on CFTR, as demonstrated by stimulation of intestinal organoids derived from CFTR-deficient mice or CF patients, or upon chemical inhibition of wild-type CFTR. Levels of forskolin-induced swelling by in vitro expanded rectal organoids are comparable with forskolin-induced anion currents measured in ex vivo human rectal biopsies. Temperature and chemical correction of F508del-CFTR function was easily detected by organoid-based fluid transport measurements, and responses to a panel of CFTR-restoring drugs were variable between rectal organoids derived from different F508del homozygous patients. This robust assay is the first functional readout developed in human organoids, and will facilitate diagnosis, functional studies, drug development, and personalized medicine for CF and other related diseases and afflictions.

Organoids

The term "organoid" refers to an in vitro collection of cells which resemble their in vivo counterparts and form 3D structures. Thus the assay is an ex vivo or an in vitro assay.

In some embodiments, the organoids of the assay are mammalian organoids, for example human or murine organoids i.e. they are derived from cells taken from a mammal. The mammal may be any mammal of interest, for example a human or mouse. In some embodiments the organoids are non-human. In a preferred embodiment, the organoids are human.

In some embodiments, the organoids of the assay are epithelial organoids or endothelial organoids. In a preferred embodiment the organoids are epithelial organoids. In some embodiments, the organoids do not comprise non-epithelial cells, i.e. the only cell type present in the organoid is an epithelial cell.

The organoids of the assay typically comprise a lumen, preferably a closed lumen. The cells of the organoid typically form an epithelial layer or endothelial layer around the lumen and the cells of the epithelial layer or endothelial layer are polarised. By polarised, it is meant that the epithelial layer or endothelial layer mimics the functionality of an in vivo epithelial layer or endothelial layer such that it has a functional basolateral side (facing outwards) and a functional apical side (facing the lumen). A functional polarised arrangement is important for the assay because it means that all ion channels are orientated in the same direction so that fluid uptake or secretion occurs in a consistent fashion, allowing swelling to occur.

In some embodiments, the organoids of the assay are gastric, intestinal (for example, small intestinal, colonic, rectum, duodenum or ileum), pancreatic, prostate, lung, breast, kidney, blood vessel or lymphatic vessel organoids. This typically means that the organoids are derived from gastric, intestinal (for example, small intestinal, colonic, rectum, duodenum or ileum), pancreatic, prostate, lung, breast, kidney, blood vessel or lymphatic vessel cells respectively. However, the skilled person will understand that there may be alternative ways of generating an organoid that has an in vivo genotype and phenotype. Thus, an organoid that has the in vivo genotype and phenotype of the intestine, is for the purposes of this invention comprised within the definition of an intestinal organoid. The same applies for the other organoid types listed above. In some embodiments, the one or more organoids are intestinal or lung organoids.

The term "resembles" means that the organoid has genetic and phenotypic characteristics that allow it to be recognised by the skilled person as being from or associated with a particular tissue type (such as the tissues listed above). It does not mean that the organoid necessarily has to be genetically and phenotypically identical (or thereabouts) to the corresponding in vivo tissue cell type. However, in a preferred embodiment, the organoids used in the assay comprise cells that are genetically and phenotypically stable relative to the in vivo cell or cells that the organoid was derived from. By genetically and phenotypically stable, it is meant that there is no genetic manipulation involved, only a minimum number of mutations (i.e. close to the normal number of mutations that would be expected in in vivo cells, for example during replication and DNA synthesis).

Cell lines and iPS cells are not genetically and phenotypically stable according to this definition, for example MDCK cells (for example, as described in Yang et al., *J am Soc Nephrol* 19(7) 1300-1310, 2008) are not genetically and phenotypically stable. Traditionally, cell lines and more recently iPS cells have been used as ex vivo cell/organ model (for example, Currid et al. *J. Physiol.* 555, 241-250, 2003) and/or disease models (for example, see Robinton et al. *Nature* 481, 295, 2012; Yang et al., *J am Soc Nephrol* 19(7) 1300-1310, 2008). However, traditionally, these cells have suffered a number of challenges and disadvantages. For example, cell lines cannot always be obtained from all patients (only certain biopsies result in successful cell lines because only infrequently and often after prolonged periods of time, will cells start to proliferate allowing them to be passaged to become a cell line; these cell lines typically comprise mutations which allow immortality) and therefore, cell lines cannot be used in personalised diagnostics and medicine and are generally poor predictors of therapeutic outcome, for example in drug screening. iPS cells also usually require some level of genetic manipulation to reprogramme the cells into specific cell fates. Alternatively, they are subject to culture conditions that affect karotypic or genetic integrity and so the time in culture must be kept to a minimum (this is also the case for human embryonic stem cells). This means that iPS cells cannot accurately represent the in vivo situation but instead are an attempt to mimic the behaviour of in vivo cells. Cell lines and iPS cells also suffer from genetic instability. Preferred organoids for use in the assay of the invention provide a genetically and phenotypically stable platform which faithfully represents the in vivo situation. The genetic integrity of stem cells of the invention can be confirmed, for example, by karyotype analysis or sequencing analysis. Cells can be karyotyped using known methods as described in Sato, T et al., (Single Lgr5 stem cells build crypt-villus structures in vitro without a mesenchymal niche. *Nature* 459, 262-265, 2009). A "normal karyotype" is one where all chromosomes are present (i.e. euploidy) with no noticeable alterations. Accordingly, in preferred embodiments more than 50%; more than 70%; more than 80%; more than 90%; more than 95%; or more than 99% of the cells in an organoid exhibit normal karyotypes. A "normal phenotype" refers to cells which display, to a first approximation, the same visual characteristics, gene expression and behaviour as the average in vivo counterpart cell. In preferred embodiments of the invention more than 50%; more than 70%; more than 80%; more than 90%; more than 95%; or more than 99% of the cells in an organoid cultured according to the invention exhibit normal phenotypes. Examples of genetically and phenotypically stable organoids suitable for use with the assay of the invention and methods of obtaining such organoids are provided in WO2010/090513, WO2012/168930 and Sato et al., *GASTROENTEROLOGY* 2011; 141:1762-1772. The cells of these organoids have a particularly stable genome and have a low mutational rate. For example, intestinal organoids can be expanded, maintained and differentiated according to the methods disclosed in these applications.

In some embodiments, intestinal organoids (such a small intestinal organoids) are obtained using a culture medium for small intestinal crypts, such as human small intestinal crypts, which comprises or consists of a basal medium, (for example consisting of Advanced DMEM/F12 supplemented with penicillin/streptomycin, 10 mM HEPES, Glutamax, 1× N2, 1× B27 (all from Invitrogen) and 1 mM N-acetylcysteine (Sigma)), and additionally comprising: a mitogenic growth factor such as EGF; a BMP inhibitor, such as Noggin; and any one or more of Rspondin 1-4, such as Rspondin-1 or 4. In some embodiments, this culture medium further comprises a TGF-beta inhibitor (such as A83-01) and/or a p38 inhibitor (such as SB202190). In some embodiments, intestinal organoids (such as colonic organoids) are obtained using a culture medium for colonic crypts, such as human colonic crypts, comprising or consisting of a basal medium, for example as described above, additionally comprising: a Wnt agonist, such as recombinant Wnt-3A or Wnt-3A conditioned medium; mitogenic growth factor, such as EGF; a BMP inhibitor, such as Noggin; and any one of Rspondin 1-4, such as human Rspondin-1 or 4. In some embodiments, this culture medium further comprises a TGF-beta inhibitor (such as A83-01) and/or a p38 inhibitor (such as SB202190). In some embodiments, the culture medium for human intestinal stem cells, human small intestinal crypts or human colonic crypts (also known as the HISC culture medium), comprises or consists of a basal medium, for example as described above, additionally comprising: a Wnt agonist, such as recombinant human Wnt-3A or Wnt-3A conditioned medium; EGF; a BMP inhibitor, such as Noggin; Rspondinl-4, such as human Rspondin-1; a TGF-beta inhibitor, such as A83-01; a p38 inhibitor, such as SB202190; gastrin; and nicotinamide. In some embodiments, the p38 inhibitor and/or gastrin can be excluded from the HISC culture medium. In some embodiments the invention provides a culture medium for culturing intestinal cells, comprising or consisting of a basal medium, Wnt-3a, EGF, Noggin, any one of Rspondin 1-4, a TGF-beta inhibitor, nicotinamide, and preferably a p38 inhibitor. In some embodiments, the culture medium for expanding small intestine or colon stem cells, for example human small intestine or colon cells, comprises or consists of a basal medium (for example comprising Advanced DMEM/F12, B27 (50×), n-Acetylcysteine (1 mM) and glutamin/glutamax), Wnt3A (optionally conditioned medium), any one of Rspondin 1-4 (preferably 1 ug/ml), Noggin (preferably 50-100 ng/ml), nicotinamide (preferably 10 mM), EGF (preferably 10-50 ng/ml), gastrin (preferably 10 nM), a TGF-beta inhibitor, for example A83-01 (preferably 500 nM). In a further embodiment, this culture medium additionally comprises a p38 inhibitor, for example SB202190 (preferably 100 nM). In a further embodiment, this culture medium additionally comprises a Rock inhibitor, for example LY2157299. In some embodiments, the culture medium for differentiating intestinal cells, comprises or consists of a basal medium, EGF, Noggin, a TGF-beta inhibitor and a p38 inhibitor. In some embodiments, the culture medium for differentiating small intestine or colon stem cells, for example human small intestine or colon cells, comprises or consists of a basal medium (for example comprising Advanced DMEM/F12, B27 (50×), n-Acetyl-cysteine (1 mM) and glutamin/glutamax), Noggin (preferably 50-100 ng/ml), EGF (preferably 10-50 ng/ml), gastrin (preferably 10 nM), a TGF-beta inhibitor, for example A83-01 (preferably 500 nM) and a p38 inhibitor, for example SB202190 (preferably 100 nM). In some embodiments, gastrin can be excluded from this differentiation medium. In some embodiments, a gamma-secretase inhibitor may be added to the differentiation medium (preferably at a concentration of 1 µM). Gamma-secretase inhibitors can influence cell fate decisions during differentiation e.g. towards secretory cells, such as goblet cells. In some embodiments, a RANKL may be added to the differentiation medium (for example at a concentration of 100 ng/ml). RANKL can influence cell fate decisions during differentiation e.g. towards M-cells. Also see Example 2, for a description of how one can generate organoids for use in the invention.

In some embodiments, the organoids are "disease" organoids. Similarly to "normal" organoids, disease organoids mimic the in vivo disease genotype and phenotype. This typically means that they are derived from in vivo cells with disease phenotypes. However, there may be other means for obtaining disease organoids, for example, by mutation of a normal organoid. Thus in some embodiments, the organoids have a disease or affliction. In some embodiments, the disease or affliction is characterised by altered ion and/or fluid transport. For example, in some embodiments the disease of affliction is cystic fibrosis or cholera. An organoid having a cystic fibrosis genotype and phenotype is referred to herein as a "cystic fibrosis organoid". Other disease organoids are referred to in the same way. Several diseases and/or afflictions are described in more detail in the "dis-eases or afflictions" section. All the diseases or afflictions listed in this section are relevant for disease organoids.

In preferred embodiments, the organoids of the assay are generated from primary cells, for example, from primary human cells. By "primary", it is meant that the cell is genetically substantially identical to an in vivo cell. For example, a primary cell could be a cell taken directly from a patient of interest. In an alternative embodiment, a primary cell is taken from a cell culture, preferably an organoid, and wherein the rate of accumulation of mutations in the cells is substantially the same as the rate of accumulation of mutations of in vivo cells. In preferred embodiments, the organoids are generated from stem cells, preferably adult stem cells, more preferably adult stem cells expressing Lgr5 (Barker et al., Cell Stem Cell 7, 656 2010, WO2010/090513, WO2012/168930 and Sato et al., *GASTROENTEROLOGY* 2011; 141:1762-1772). In preferred embodiments, the organoids are generated and maintained using the culture media and methods described in WO2010/090513, WO2012/168930 and/or Sato et al., *GASTROENTEROLOGY* 2011; 141:1762-1772.

In one embodiment, the organoids are not derived from tumour-derived immortalised cell lines or a cell therefrom. In one embodiment, the organoids are not derived from a clonal population of cells or a cell therefrom. In one embodiment, the organoids are not derived from a cell line or a cell from a cell line.

In some embodiments, the assay of the invention further comprises generating the one or more organoids by expanding stem cells into closed organoids which include a closed lumen on the apical membrane of the cells.

In some embodiments, the assay of the invention further comprises generating the one or more organoids from a primary cell.

In some embodiments, the assay of the invention further comprises generating the one or more intestinal organoids by expanding intestinal stem cells into closed organoids which include a closed lumen on the apical membrane of the cells.

Swelling

In some embodiments, the swelling of the one or more organoids comprises a change in size, such as a change in surface area, diameter and/or volume, and/or wherein the swelling comprises a change in content of the organoid.

The inventors have shown that normal organoids have observably and measureably different phenotypes to disease organoids. This difference can arise from mutations in the ion channels and regulatory proteins that regulate fluid uptake and secretion. Typically, fluid uptake and secretion is regulated by active transport of ions across cellular membranes or layers which leads to changes in osmotic pressure and movement of water into/out of the lumen. For example, in normal secretory epithelia, fluid secretion into the lumen is driven by chloride exit across the cell apical membrane which results in transepithelial sodium and water secretion. This luminal fluid accumulation is mimicked by the organoids and, as has been observed for the first time by the inventors, causes "swelling" of the normal organoids. This results in organoids with relatively high internal pressure (e.g. in the lumen) which forces the organoids into a large turgid ball shape, typically resulting in cell stretching which promotes division and thinning.

By contrast, a disease organoid characterised by altered ion and/or fluid transport displays "abnormal swelling". In some embodiments, a disease organoid may have reduced swelling (when compared to a normal organoid), which is characterised by a reduction in one or more of the features described above e.g. lower internal pressure, smaller organoid, lower turgidity, reduced ball-like shape, reduced stretching etc. when compared to a normal organoid. These characteristics result in a more folded structure (more extrusions or fold-like structures forming the surface of the organoid). An example of a disease organoid with reduced swelling is a cystic fibrosis organoid. Stimulation of the organoids with certain drugs and/or compounds can also result in reduced swelling. Examples of compounds which result in reduced swelling are CFTRinh172 and GIyH-101 FIGS. 3 and 4). In alternative embodiments, a disease organoid may have increased swelling (when compared to a normal organoid), which are characterised by an enhancement of one or more of the features described above e.g. higher internal pressure, larger organoid, greater turgidity, enhanced ball-like shape, increased stretching etc. when compared to a normal organoid. An example of a disease organoid with increased swelling is a cholera organoid. Stimulation of the organoids with certain drugs and/or compounds can also result in enhanced swelling. Examples of compounds which result in enhanced swelling are forskolin, salbutamol, epinephrine, ritodrine, dopamine or cholera toxin. An example of a drug which results in enhanced swelling (particularly when stimulating a cystic fibrosis organoid) is genistein (for example see FIG. 7). Other cystic fibrosis drugs which would result in enhanced swelling of cystic fibrosis organoids are listed in Table 2.

Accordingly, as mentioned above, the extent of the organoid swelling can be determined by measuring the change in size or the change in content of the one or more organoid in the assay. The "change" may refer to the difference when a normal organoid is compared to a disease organoid and/or when a control organoid is compared to an organoid that has been stimulated by one or more drug or compound. Alternatively, the "change" may refer to the difference in swelling of an organoid before and after stimulation with a drug and/or compound.

Thus in some embodiments, the change in size and/or the change in content is the change in size compared to a healthy control organoid. In a preferred embodiment, the healthy control organoid is similar or substantially identical to the disease organoid, except that it does not have the disease of interest. For example, in a preferred embodiment, the control and disease organoids are derived from the same tissue type (for example, the size of an organoid generated from an CF intestinal biopsy would be compared to the size of an organoid generated from a healthy intestinal biopsy). It would be understood by the skilled person that the organoids are preferably the same "age", i.e. the cells have been cultured and/or passaged a similar number of times and/or the starting size is substantially the same.

In an alternative embodiment, the change in size and/or the change in content is the change in size compared to a control organoid that has not been stimulated with the one or more drugs. In a preferred embodiment, the control organoid is similar or substantially identical to the organoid that been stimulated with the one or more drugs, except that it has not been stimulated with the one or more drugs. For example, in a preferred embodiment it is derived from the same tissue type. It would be understood by the skilled person that the organoids are preferably the same "age", i.e. the cells have been cultured and/or passaged a similar number of times and/or the starting size is substantially the same.

In a further embodiment, the change in size and/or the change in content is the change in swelling of an organoid before and after stimulation with a drug and/or compound.

In some embodiments, the change in organoid size may occur concurrently with a change in the diameter or volume of the lumen. However, one of the advantages of the assay of the invention is that it allows the organoid size, rather than the lumen size to be used as an indication of healthy versus diseased versus successfully treated organoids. Currid et al., (2003) describe the observation that forskolin treatment of tumour-derived cell lines (with organoid-like structures) results in the formation of a lumen-like structure. However, the authors do not make the link that this lumen-formation would be inhibited by diseases of afflictions that inhibit the function of the CFTR (or other proteins involved in fluid transport and secretion). Furthermore, the Currid "organoids" do not change in size in response to forskolin treatment; the only change appears to be the formation of the lumen (in particular see FIG. 1 of Currid et al.). By contrast the assay of the present invention involves observation of swelling of the organoids themselves. This is advantageous because overall organoid size (e.g. diameter/volume/surface area) is far easier to measure. For example, as described in the present examples, under certain labeling conditions, quantification software was not able to discriminate between the cells and the lumen due to the lack of contrast. Therefore, it is not always possible to observe changes in lumen size. By contrast, it is possible to use automated quantification methods to determine overall changes in organoid size.

The change can be assessed by manual or automated measurement of the organoid, as described below.

In some embodiments, measuring comprises quantitatively measuring the change in size of the organoid. By change in size, it is meant that there is a change in the surface area and/or diameter and/or volume of the organoid. In some embodiments, the change in size will be a change of at least 1%, at least 2%, at least 5%, at least 10%, at least 20%, at least 50% or more of the surface area and/or diameter and/or volume of the organoid. In some embodiments, the change in size is a change of at least 2-fold, at least 3-fold, at least 4-fold, at least 5-fold, at least 6-fold at least 7-fold, at least 10-fold, at least 20-fold or more of the surface area and/or diameter and/or volume of the organoid. The change can be an increase in size (enhanced swelling) or a decrease in size (reduced swelling). For example, FIG. 8 shows that forskolin and cholera toxin causes human organoids to more than double in size in the space of 120 minutes.

In other embodiments, measuring comprises observing the organoid swelling. This may involve, for example, determining the change in content of the organoid. By change in content, it is meant that the content or structure of the organoid changes. In some embodiments, the change in content is characterised by a change in organoid shape (e.g. more ball-like or more folded or less ball-like or less folded); change in cell size and stretching and/or change in internal pressure and/or rigidity. Thus in some embodiments, measuring the change in content or structure comprises observing whether the organoid becomes more or less folded, or for example, determining whether an organoid of interest (a disease organoid or a drug-treated organoid, respectively) is larger or smaller than a control organoid (e.g. a healthy organoid or a non-drug treated organoid, respectively). In some embodiments, if there is reduced swelling, observing the swelling may involve determining whether it becomes more deflated and folded. Change in content and structure can also be quantitatively measured.

In some embodiments, the organoid swelling can be visibly observed such that one or more of the features described above can be seen. It is to be understood that "visibly" does not require visibility using the naked eye, but includes, for example, the use of microscopy, imaging and/or staining techniques.

Various techniques known in the art could be used to determine organoid size or content. In a preferred embodiment, the organoid size or content is determined using live cell imaging, for example using a microscope, such as a confocal microscope. In some embodiments the organoids are stained prior to imaging to improve the contrast of the image. In a further embodiment the organoids are stained with cell-permeable dyes that optionally fluoresce upon metabolic conversion by living cells e.g. Cell Tracker-Orange, Cell Tracker-Green, Calcein-Green (all available commercially from Invitrogen). In one embodiment, the organoids are stained with Calcein-Green, optionally at approximately 10 µM for approximately 60 minutes. Thus in some embodiments the assay of the invention comprises the step of staining the organoids e.g. by incubation with a staining agent.

In some embodiments, the change in size can be quantified, for example using imaging software such as "Volocity quantification software". In some embodiments, the total organoid area increase relative to T=0 (time of stimulation) is calculated and optionally averaged from multiple organoids. The area under the curve (AUC) can be calculated, for example using Graphpad Prism, to show the change in area of the organoid.

In some embodiments, the organoids may undergo rapid swelling, (e.g. in response to stimulation by drugs or compounds) that can be detected within hours, minutes or even seconds. Thus, in some embodiments of the assay, the organoid swelling is measured in less than 48 hours, less than 36 hours, less than 24 hours, less than 18 hours, less than 12 hours, less than 6 hours, less than 1 hour, less than 45 minutes, less than 30 minutes, less than 15 minutes, less than 10 minutes, less than 9 minutes, less than 8 minutes, less than 7 minutes, less than 6 minutes, less than 5 minutes, less than 4 minutes, less than 3 minutes, less than 2 minutes, less than 1 minute or less than 30 seconds.

In some embodiments, the organoids may undergo slow swelling, (e.g. when determining the difference between a diseased and normal organoid which have not been stimulated by drugs or compounds) that can be detected within weeks or days. Thus, in some embodiments of the assay, the organoid swelling is measured in less than 4 weeks, less than 3 weeks, less than 2 weeks, less than 1 week, less than 6 days, less than 5 days, less than 4 days or less than 3 days.

Stimulation of Organoid Swelling

In some embodiments, the assay comprises stimulation of the one or more organoids with a compound which is capable of inducing swelling, for example, a change in size, of the organoids.

The inventors have shown that certain compounds result in enhanced organoid swelling. For example, forskolin, which is known to raise intracellular cAMP and thereby activate the cystic fibrosis transmembrane receptor (CFTR) results in enhanced organoid swelling, presumably owing to increased fluid uptake into the organoid lumen. The effect is CFTR-dependent, as demonstrated using CFTR-inhibitors which prevent forskolin-induced swelling. Thus the inventors have demonstrated that organoids stimulated by forskolin, or other CFTR activators, enhance the swollen phenotype seen in normal organoids and also enhance swelling in successfully treated disease organoids. This effect can be used to enhance the "change" in size or content of the organoid measured in the assay of the invention and to achieve rapid organoid responses, which could be useful for rapid diagnosis, drug testing or personalised medicine.

Forskolin is a labdane diterpene, with the chemical formula $C_{22}H_{34}O_7$, that is produced by the Indian *Coleus* plant. Thus it is a small-molecule inhibitor with a molecular mass of 410.5 g/mol. Its UPAC ID is: (3R,4aR,5S,6S,6aS,10S,10aR,10bS)-6,10,10b-trihydroxy-3,4a,7,7,10a-pentamethyl-1-oxo-3-vinyldodecahydro-1H-benzo[f]chromen-5-yl acetate. Forskolin is commonly used to raise levels of cyclic AMP in the study and research of cell physiology. Salbutamol, epinephrine, ritodrine, dopamine and cholera toxin have been shown to have a similar effect to Forskolin on the organoids.

Thus in some embodiments, the assay comprises stimulation of the one or more organoids with a compound which is capable of inducing a change in size of the organoids, wherein the compound indirectly activates the CFTR, for example via the cAMP-PKA pathway. In some embodiments, the compound is forskolin, salbutamol, epinephrine, ritodrine, dopamine or cholera toxin.

In some embodiments, the compound is a G-coupled protein receptor (GCPR) that enhances cAMP levels. In some embodiments, the compound is a small-molecule that enhances cAMP levels, for example forskolin. In some embodiments, the compound is a diterpene or diterpenoid, optionally a ladane diterpene and/or a forskolin-like diterpene of diterpenoid as described, for example, in Rijo P et al. (*Magn Reson Chem.* 2005 July; 43(7):595-8).

All reagents associated with modulation of fluid secretion or absorption by modulating cellular signaling that is generally accepted to regulate CFTR ion channel function. These include modulators of cAMP, cGMP, protein kinase A, protein kinase C, phosphorylation of CFTR and CFTR ATP-ase activity.

In some embodiments, the compound is a cAMP-generating compound, such as an adrenergic receptor stimuli. Examples of adrenergic stimuli include but are not limited to isoproperenol, salbutamol, epinephrine; prostaglandine E2, VIP, and substance P. In some embodiments, the compound is a cGMP generating compound, such as a guanylin or bile acid. In some embodiments, the compound is an inhibitor of phosphodiesterases, for example milrinone, IBMX, sildenafil (Viagra). In some embodiments, the compound is a calcium modulators, for example, ionomycin, acetyl choline or carbachol. In some embodiments, the compound is a modulator of cellular signalling, such as P13K, Syk or p38. In some embodiments, the compound is a modulator of CFTR folding and trafficking, for example Vertex-809 and Vertex-661, SAHA, miRNA-138. In some embodiments, the compound is an epigenetic modulator, for example, of SAHA or TSA. In some embodiments, the compound is a modulator of CFTR expression, such as miRNA-138, IL-1, TNF-alpha, or p38 regulator. In some embodiments, the compound is a modulator of CFTR degradation, such as a proteasome inhibitor including bortezimib or a modulator of endoplasmic reticulum associated degradation via ubiquitin-dependent pathways. In some embodiments, the compound is a CFTR inhibitor adapted from JR Thiagarajah et al. (*Clin Pharmacol Ther,* 2012 CFTR Inhibitors for Treating Diarrheal Disease), for example one of the compounds shown below:

Original CFTR inhibitors

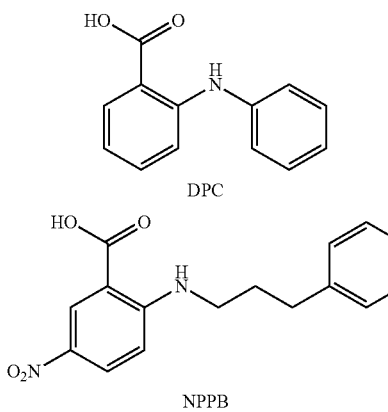

DPC

NPPB glibenclamide

Absorbable inhibitors

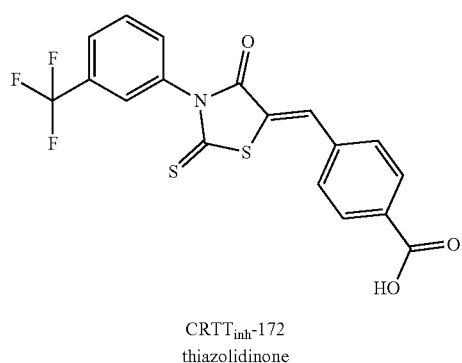

CRTT$_{inh}$-172
thiazolidinone

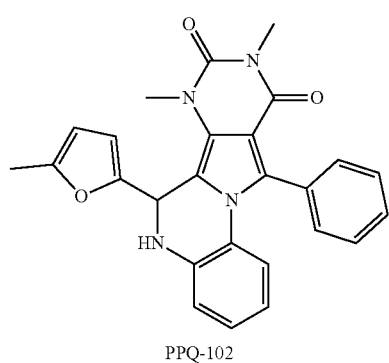

PPQ-102

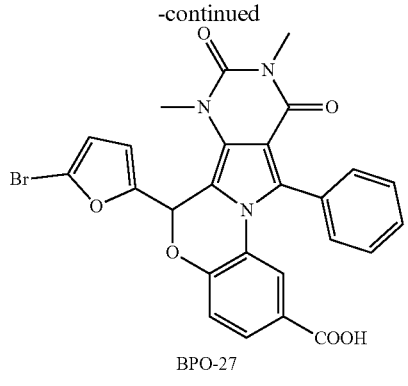

BPO-27
PPQ/BPO inhibitors

Externally acting inhibitors hydrazides

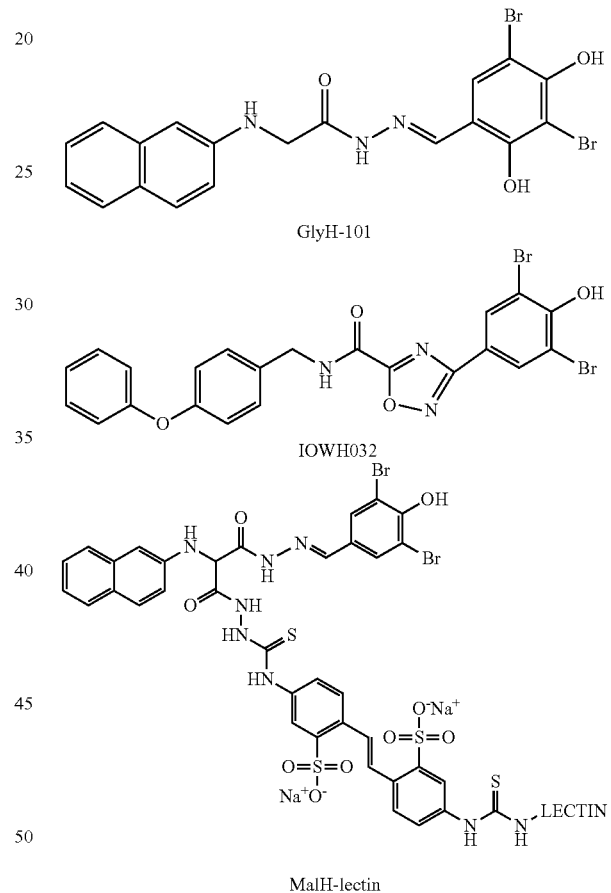

GlyH-101

IOWH032

MalH-lectin

Any suitable compound may be used to stimulate the one or more organoids in the assay of the invention. For example, all reagents associated with modulation of fluid secretion or absorption by modulating cellular signalling may be used to stimulate the one or more organoids in the assay of the invention. Examples of compounds which may be used to stimulate the one or more organoids in the assay of the invention include modulators of cAMP, cGMP, protein kinase A, protein kinase C, phosphorylation of CFTR and CFTR ATP-ase activity. For example, other compounds which activate the CFTR and thus could replace forskolin in the assay include cholera toxin and salbutamol and mimics and derivatives thereof.

In some embodiments, the assay comprises stimulation of the one or more organoids with a compound which is capable of inducing a change in size of the organoids, wherein the compound is forskolin or a mimic or derivative thereof. In a further embodiment, forskolin-induced swelling of organoids can be reversed upon removal of forskolin by washing. Similarly, swelling of organoids caused by other compounds can be reversed by washing to remove the compound.

A number of non-CFTR ion channels and other proteins are involved in transferring organoid and inorganic substances across cellular membranes at the apical and basolateral membranes, and thus affect fluid secretion or uptake. Thus, in some embodiments the compound indirectly activates the CFTR or another ion channel or regulatory protein involved in the regulation of fluid uptake and secretion. In an alternative embodiment, the compound directly activates the CFTR or another ion channel or regulatory protein involved in the regulation of fluid uptake and secretion.

Ion channels other than the CFTR, and other proteins involved in ion channel regulation in cells, are also important for the regulation of fluid and electrolyte homeostasis in cells. For example, all of the ion channels shown in Tables 1 and 2 are involved in the regulation of fluid secretion and uptake in cells. In a further example, the CFTR is predicted to help regulate a number of other ion channels including but not limited to: ORCC, ROMKK$^+$, ENaC, and the Cl—/HCO$^3$ exchanger. Modulators of these ion channels and regulatory proteins, such as the activators and inhibitors listed in Tables 1 and 2 (adapted from Toczylowska-Maminska et al, 2012, *J of Cell Biochem* 113:426:-432), are hypothesised to function in a similar way to forskolin by enhancing or reducing the swelling of organoids. Thus, in some embodiments of the invention, the compound of the assay which is capable of inducing a change in size of the organoids directly or indirectly activates or inhibits any one or more of the ion channels in Tables 1 or 2 and/or any one or more of NHE3 ion exchanger, DRA, SGLT1, short-chain fatty acid transporters, ORCC, ROMKK$^+$, ENaC, or the Cl/HCO$^3$ exchanger.

In some embodiments, the compound of the assay which is capable of inducing a change in size of the organoids may be any one or more of the activators or inhibitors listed in Tables 1 or 2.

TABLE I

Activators and Inhibitors of Transport Proteins in Apical Membrane of the Human Bronchial Epithelium.

| Name | Gene | Activator | Inhibitor |
| --- | --- | --- | --- |
| K$^-$ channels | | | |
| TREK-1 | kcnk2 | halothane, chloroform, isoflurane, arachidonic acid | lidocaine, quinidine, Gd$^{3-}$, fluoxetine bupivicaine |
| TWIK-1 | kcnk1 | PMA | quinidine, Ba$^{3-}$ |
| TWIK-2 | kcnk6 | arachidonic acid | halothane |
| TASK-2 | kcnk5 | halothane | bupivacaine, quinine, quinidine, acidic pH, lidocaine, clofilium |
| Kir4.2 | kvnj15 | ATP | Ba$^{2+}$ |
| Cl$^-$ channels | | | |
| CFTR | cftr | ATP, forskolin, genistein, phloxine, apigenin | glibenclamide, arachidonic acid, Ibuprofen |
| CaCC (CLCA) | clca1 clca2 unem16a | ionamycin, >2 mM Ca$^{2-}$, norephinephrine, ATP, endothelin | niflumic acid, DIDS, DTT |
| VSOR | not known | H$_2$O$_2$ | glibenclamide, DIDS, NPPB, niflumic acid Mg$^{3+}$, verapamil |
| Na$^+$ channels | | | |
| ENaC | enac | aldosterone, insulin, vasopressin | amiloride, triamterene, benzamil |
| Ion transporters | | | |
| Na/H ion exchanger | nhe1 | acidic pH | angiotensis II, amiloride |
| HKATPase | atp1al1 | histamine | ouabein, oligomycin, SCH28080 |

TABLE II

Activators and Inhibitors of Transport Proteins in Basolateral Membrane of the Human Bronchial Epithelium

| Name | Gene | Activator | Inhibitor |
| --- | --- | --- | --- |
| K$^+$ channels | | | |
| KvLQT1 | kcnq1 | cAMP, Ca$^{2+}$, 1-EBIO | chromanol compound 293B, clofilium, linopirdine, Ba$^{2+}$ |
| hIK-1 (hSK4, KCa3.1) | kcan4 | 1-EBIO, Ca$^{2-}$, 7,8-benzoquinoline | clotrfinazolum, ChTx, Ba$^{3+}$ |
| Cl$^-$ channels | | | |
| ORCC | not known | cAMP Gd$^{3+}$ | DIDS |
| ClC-2 | clc-2 | acidic pH, lubiprostone, arachidonic acid, omeprazole | Zn$^{2+}$ |
| bestrophins | best1 | NO, ATP, ionomycin | DIDS, niflumic acid |
| Ion transporters | | | |
| Na2HCO3 ion transporter | nbc1, nbc4 | forskolin, calmodulin, carbachol | DIDS, DNDS |
| NaK2KCl ion transporter | nkcc1 | ATF, placidil | bumetamide, furosemide, benzmetanide, torsemide |

TABLE II-continued

Activators and Inhibitors of Transport Proteins in Basolateral Membrane of the Human Bronchial Epithelium

| Name | Gene | Activator | Inhibitor |
|---|---|---|---|
| Cl/HCO3 ion exchanger | ac2 | $NH_4^+$ | calmidazolium, acidic pH, DNDS, DIDS |
| NaKATPase (NKA, EC 3.6.1.3) | atp1q1, atp1a2 | thyrotropin, aldosterone | β-mercaptoethanol, vanadate, DTT, ouabain, oligomycin, 3,4,5,6-tetrahydroxy-xanthone, oleandrin, digoxin |

In some embodiments, the compounds capable of inducing a change in size for use in the assay of the invention may be, for example, proteins, peptides, synthetic small molecules, aptamers, nucleic acids (such as antisense compounds) or antibodies (or fragments thereof).

In a further embodiment, some organoids, such as mouse CFTR-delF508 organoids have higher residual CFTR activity than human counterparts (for example, see FIGS. 6A to 6D), and respond to CFTR correction by temperature as well as compounds by increased forskolin-induced swelling.

Mutations in ion channels (such as those mentioned above or listed in Tables 1 and 2) and regulatory proteins may cause altered ion and fluid transport resulting in disease phenotypes including, but not limited to: bacterially induced diarrhoea (e.g. caused by cholera, or other bacterial toxins); rotavirus infection; enterohemorrhagic E. coli, adrenoleukodystrophy; asthma, Tangier disease; multi-drug resistance (many cancers, as well as some antibiotic resistant bacteria); obstetric cholestasis and polycystic kidney disease. Thus in some embodiments, the disease or affliction diagnosed or studied by the assay of the invention is selected from: bacterially induced diarrhoea (e.g. caused by cholera, or other bacterial toxins); rotavirus infection; enterohemorrhagic E. coli; adrenoleukodystrophy; asthma, Tangier disease; multi-drug resistance (many cancers, as well as some antibiotic resistant bacteria); obstetric cholestasis and polycystic kidney disease. The skilled person would understand which ion channels and which mutations to target depending on the disease being studied.

The invention provides an assay according to the invention, which comprises stimulation of one or more organoids with a compound targeting the CFTR and imaging said one or more organoids, whereby compound-induced swelling of the one or more organoids is CFTR-dependent.

The invention also provides an assay for screening a compound library to identify compounds that affect the fluid uptake and/or secretion, wherein the assay comprises:
 stimulation of one or more organoids with the compound library;
 imaging swelling of said one or more organoids; and
 identifying a compound which is capable of inducing swelling of the organoids.

It is to be understood that any of the compounds listed in this section may be equally applicable as examples of drugs for drug screening and personalised medicine. Conversely, any of the examples of drugs provided in the drug screening and personalised medicine section may be equally applicable as examples of compounds for inducing organoid swelling. One difference that may exist between appropriate compounds for stimulating organoid swelling in the assay versus the drugs that might be tested in the assay is that the compounds typically act upstream of the ion channels and/or proteins that regulate fluid secretion and uptake into a cell and thereby enhance (or reduce) organoid swelling. By contrast, the drugs typically act on and/or downstream of dysfunctional ion channels and/or proteins to correct normal fluid secretion and uptake.

Disease or Affliction

In some embodiments, the invention provides an assay for diagnosing a disease or affliction that affects fluid uptake or secretion (of organoids and/or the cells of the organoids) or for studying the effectiveness of one or more drugs for treating the disease or affliction, for example, wherein the disease is preferably cystic fibrosis or cholera.

Thus, in one embodiment the invention provides an assay according to the invention wherein the swelling of the one or more organoids is a measure of the effect of CFTR mutation and/or drug treatment.

Other diseases or afflictions, in addition to cystic fibrosis and cholera, that are relevant for use with the assay of the invention include, but are not limited to: bacterially induced diarrhoea (e.g. enterohemorrhagic E. coli or caused by cholera toxins or other bacterial toxins); rotavirus infection; adrenoleukodystrophy; asthma, Tangier disease; multi-drug resistance (many cancers, as well as some antibiotic resistant bacteria); obstetric cholestasis, COPD, smoking, sinusitis, pancreatic insufficiency, pancreatitis, infertility, malnutrition, inflammatory diseases, renal disease including polycystic kidney disease, allergic disease, osteoporosis, diabetics, hypertension, hypotension, pathogen-induced diarrhoea (cholera, E. coli), 'drying out', liver cirrhosis, malfunction of liver, tumorigenesis. Smoking can reduce CFTR function and thus smoker's cough or other side-effects of smoking are other afflictions that are relevant for use with the assay of the invention.

The CFTR also plays an important role in the pathogenesis of polycystic kidney disease, particularly autosomal dominant polycystic kidney disease (Li et al., Am J Phsiol Renal Physiol 303, 1176-1186, 2012). Mutations in the polycystin proteins lead to the formation of epithelial cysts containing a fluid-filled cavity surrounded by a single layer of immature renal epithelial cells (e.g. Sullivan et al., J. Am Soc Nephrol 9, 903-916, 1998). Fluid accumulation within these cysts involves cAMP-stimulated transepithelial $C_1$ movements reminiscent of those found in secretory epithelia affected by cystic fibrosis (e.g. Torres et al., Lancet 369, 1287-1301, 2007). It has been shown that F508del-CFTR mutation disrupts renal cyst formation. This shows that the assay would also be suitable for diagnosing polycystic kidney disease and for studying the effectiveness of one or more drugs for treating polycystic kidney disease. The assay would also be suitable for other diseases, such as those listed above, which result in similar fluid transport dysfunction.

In some embodiments, the disease or affliction is associated with a loss-of-function mutation of an ion channel, for example CFTR, ORCC, ROMKK$^+$, ENaC, or the $C_1/HCO^3$ exchanger, or is associated with a loss-of-function mutation of other proteins associated with the regulation of these ion channels. In some embodiments the disease or affliction is associated with a deletion of phenylalanine at position 508 (CFTR-delF508). This causes misfolding, ER-retention and early degradation of the CFTR protein which prevents function at the plasma membrane. Thus, in some embodiments, the disease or affliction is characterised by misfolding, ER-retention and/or early degradation of the CFTR protein. In some embodiments, the disease or affliction is associated with one or more mutations in the CFTR gene that impair protein folding, protein production, gating, conductance, splicing and/or interactions with other proteins. In some embodiments, the disease or affliction is associated with the CFTR-G551D mutation. In some embodiments, the disease or affliction is associated with the CFTR-G542X mutation. In some embodiments, the disease or affliction is associated with the CFTR-L927P mutation. In some embodiments, the disease or affliction is associated with the CFTR-E60X mutation. In some embodiments, the disease or affliction is associated with the CFTR-4015delATTT mutation. In some embodiments, the disease or affliction is associated with the CFTR-A455E mutation (see for example, FIG. 14A), In some embodiments, the disease or affliction may be caused by the homozygous allele of any one of the above-mentioned mutations. In an alternative embodiment, the disease or affliction may be caused by the heterozygous allele of any combination of the above mutations or a combination of the above mutation with a normal (non-mutant) CFTR gene. In some embodiments, a loss of function mutation in CFTR leads to cystic fibrosis, and this disease can be detected and/or diagnosed by observation of reduction in organoid swelling compared to a normal healthy organoid.

In an alternative embodiment, the functionality of CFTR is altered by a toxin, such as a bacterial toxin, such as the cholera toxin, and thus cholera toxin can be detected and/or diagnosed by observation of enhanced organoid swelling compared to a normal healthy organoid.

The above-mentioned diseases and/or afflictions are also relevant for the types of disease organoid that are mentioned above. A disease organoid can be used as a disease model to study the effect of drugs on a particular disease phenotype and/or genotype, optionally for drug discovery or for personalised medicine, such as choice of drug treatment, as explained in more detail below.

The invention provides an assay according to the invention which further comprises correlating the swelling of the one or more organoids with:
the presence or severity of the disease or affliction, or
the responsiveness of the organoid to treatment with a known or putative drug
or the effectiveness of a known or putative drug.

Use of the Assay in Diagnosis

The invention also provides an assay according to the invention, for use in diagnosis of a disease or affliction. The disease or affliction can be any disease or affliction mentioned herein or any disease or affliction that affects fluid uptake or secretion.

The invention also provides an assay according to the invention, which comprises measuring the swelling in one or more organoids from a patient being diagnosed, for example for cystic fibrosis or cholera, and comparing this with the swelling in one or more organoids from a healthy control.

In some embodiments, the assay further comprises stimulation of the one or more organoids with a compound, such as forskolin, that enhances the normal swelling phenotype.

In some embodiments, change in swelling of the patient organoid compared to the healthy organoid indicates the presence of the disease or affliction. Furthermore, quantification of the change in size can demonstrate the presence of the disease or affliction and/or its severity. For example, reduced swelling of a patient organoid might indicate the presence of a dysfunctional CFTR (or other ion channel or regulatory protein that affects fluid uptake or secretion). For example, in some embodiments, the change is exemplified by comparison of forskolin-induced swelling in organoids grown from a healthy control or a CF patient carrying homozygous F508del mutations (for example, see FIG. 5A). In some embodiments, this would indicate a positive diagnosis for cystic fibrosis. Alternatively, increased swelling of a patient organoid might indicate the presence of an overactive CFTR (or other ion channel or regulatory protein that affects fluid uptake or secretion). In some embodiments, this would indicate a positive diagnosis for cholera. Diagnosis of a disease or affliction, such as cystic fibrosis or cholera, can then lead to treatment of the patient for the relevant disease or affliction.

The invention also provides the use of one or more organoids for diagnosis of a disease or affliction such as cystic fibrosis or cholera, wherein said diagnosis comprises use of an assay according to the invention.

The invention also provides a method for treating a patient, wherein the method comprises use of the assay of the invention for diagnosis, wherein if a positive diagnosis is obtained the patient is treated for the disease or affliction.

A therapeutic agent for use in treating a disease or affliction wherein said treating comprises diagnosing a patient for the presence of a disease or affliction using an assay of the invention and wherein if a positive diagnosis is obtained, the patient is treated for the disease or affliction.

In some embodiments, the patient is treated using one or more drugs identified using a drug screening assay of the invention as described below.

Use of the Assay in Drug Screening

The invention also provides an assay according to the invention for use in drug screening, for example for screening a library of potential drugs.

In some embodiments, the assay is a high-throughput screening assay. For example, in some embodiments, organoids are cultured in an array format, for example in multi-well plates, such as 96 well plates or 384 well plates.

In some embodiments, the organoids in the drug screen, for example in the array, are derived from one individual patient. In some embodiments, the organoids in the drug screen, for example in the array, are derived from different patients. In other embodiments, the drug screen, for example the array, comprises organoids derived from one or more diseased patients in addition to organoids derived from one or more healthy controls.

Libraries of molecules can be used to identify a molecule that affects the organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich) natural compound libraries (Specs, TimTec) or small molecule libraries.

Furthermore, genetic libraries can be used that induce or repress the expression of one of more genes in the progeny of the stem cells. These genetic libraries comprise cDNA libraries, antisense libraries, and siRNA or other non-coding RNA libraries. The cells may be exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death.

In some embodiments, the organoids can be used in the assay to test libraries of chemicals, antibodies, natural product (plant extracts), etc for suitability for use as drugs, cosmetics and/or preventative medicines. For instance, in some embodiments, a cell biopsy from a patient of interest, such as intestinal cells from a cystic fibrosis patient, can be cultured using culture media and methods of the invention and then treated with a drug or a screening library. It is then possible to determine which drugs effectively restore function to the faulty ion channel or other regulatory protein. This allows specific patient responsiveness to a particular drug to be tested thus allowing treatment to be tailored to a specific patient. Thus, this allows a personalized medicine approach, which is described in more detail below.

The added advantage of using the organoids for identifying drugs in this way is that it is also possible to screen normal organoids (organoids derived from healthy tissue) to check which drugs and compounds have minimal effect on healthy tissue. This allows screening for drugs with minimal off-target activity or unwanted side-effects.

In some embodiments, the assay is for testing the effect of novel drugs on functional restoration of mutant ion channels or other proteins involved in regulating fluid uptake or secretion. In some embodiments, functional restoration comprises restoration of translation, transcription, of gene loci or biological interactors, for treatment of diseases and afflictions associated with fluid uptake or secretion.

For example, the inventors observed forskolin-induced swelling in CF organoids upon addition of drugs that are known to correct CFTR function in vitro (FIG. 5B). Thus, in some embodiments, the assay of the invention can be used to measure the effect of existing or novel treatments for CFTR.

In some embodiments, the invention provides a method or assay using the organoids to test effect of novel drugs to treat CFTR deficiency through CFTR function correction.

In some embodiments, the assay is for testing the effect of novel drugs on functional restoration of mutant CFTR protein, or functional restoration of CFTR translation, transcription, CFTR gene loci or biological interactors of CFTR, for example for treatment of cystic fibrosis or microbial toxins, such as cholera. In some embodiments the drugs are potentiators or correctors. For example in some embodiments the potentiator is genistein (see for example FIG. 7, which shows that genistein can induce rapid organoid swelling).

Functional restoration of CFTR comprises functional restoration of mutant CFTR protein, functional restoration of CFTR translation (e.g. premature stop codons), transcription (e.g. splicing defects), or functional restoration of the CFTR gene (e.g. gene therapy) or the CFTR interactome (some mutations impact protein-protein interactions required for CFTR function).

In some embodiments, the assay for drug screening is for identifying drugs that target mutation-specific defects in ion channels or other proteins involved in regulating fluid uptake or secretion, for example mutation-specific defects of the CFTR protein itself. For example, in some embodiments, the assay for drug screening is for identifying drugs that induce i) premature stop codon readthrough, ii) correction of plasma membrane trafficking of CFTR (correctors), and/or iii) enhance CFTR gating (potentiators). In some embodiments, the assay for drug screening is for identifying combinations of correctors and potentiators, for example for treatment of the CFTR-delF508 dominant patient-group.

In some embodiments, the assay for drug screening comprises stimulation of the one or more organoids with a drug known to treat the disease or affliction of interest, or being tested for its efficacy in treating the disease or affliction of interest, wherein enhancement or reduction of organoid swelling is indicative of an effective drug for treatment of said disease or affliction.

In some embodiments, the drug being tested is selected from a synthetic small molecule, protein, peptide, antibody (or derivative thereof), aptamer and nucleic acid (such as an antisense compound).

In a further embodiment, the assay for drug screening additionally comprises stimulation of the one or more organoids with a compound, such as forskolin, which is capable of enhancing swelling of the organoids.

In some embodiments, the assay for drug screening comprises stimulation of one or more organoids with a compound which is capable of inducing swelling of the organoids;

stimulation of the one or more organoids with a drug known to affect CFTR function or with a drug being tested for its efficacy in affecting CFTR function; and imaging the swelling of the one or more organoids, and optionally comparing the swelling of the organoid to the swelling of an organoid which has been stimulated with the compound but has not been stimulated with the drug;

wherein swelling of the one or more organoids in response to stimulation by the drug indicates that the drug is effective for treatment of functional restoration of mutant CFTR.

In some embodiments, the assay further comprises the step of selecting the effective drug and optionally using said drug for treatment.

The invention also provides the use of one or more organoids for drug screening, wherein the drug screening comprises using an assay according to the invention.

Use of the Assay in Personalised Medicine

In some embodiments, the invention provides an assay wherein the organoids are patient derived small intestinal organoids for the assessment of the individual responsiveness to certain treatment options.

In some embodiments, the assay comprises stimulation of the one or more organoids with one or more drugs, for example for use in personalised medicine.

In some embodiments, the invention provides an assay for use in personalised medicine, for example to test individual patient response to drugs for the disease or affliction of interest.

In some embodiments, the invention provides a method using organoids for testing individual patient response to drugs such as correctors or potentiators or other drugs used to treat CF, for example any of the drugs shown in Table 3 or Table 4.

TABLE 3

Examples of known drugs for cystic fibrosis

| ID | Chemical Name | Chemical Structure | Comments |
|---|---|---|---|
| B1 | 4-[4-Oxo-2-thioxo-3-(3-trifluoromethyl-phenyl)-thiazolidin-5-ylidenemethyl]-benzoic acid | 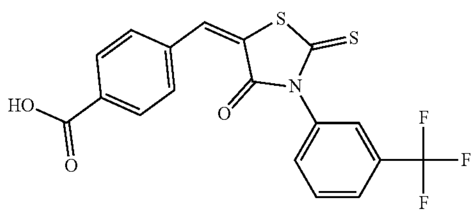 [SMILES: O=C(O)c1ccc(/C=C2/SC(=S)N(c3cccc(C(F)(F)F)c3)C2=O)cc1] | Reference #**1<br>Name: CFinh-172<br>Potency: Ki = 300 nM<br>Solvent: DMSO<br>Hints For Use: Slow onset of inhibition in some cell types (eg. T84 cells) requiring prolonged incubation.<br>M.W.: 409 |
| B2 | (Naphthalen-2-ylamino)-acetic acid (3,5-dibromo-2,4-dihydroxy-benzylidene)-hydrazide | 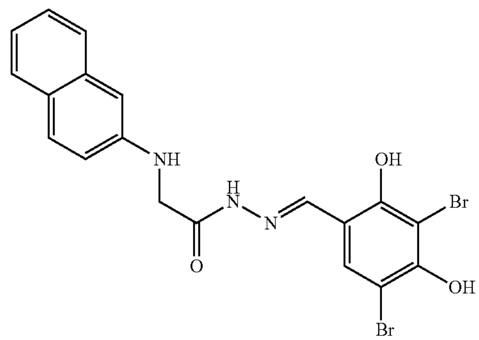 [SMILES: O=C(CNc1ccc2ccccc2c1)N/N=C/c1cc(Br)c(O)c(Br)c1O] | Reference #**2<br>Name: GlyH-101<br>Potency: Ki = 5 microM<br>Solvent: DMSO<br>Hints For Use:<br>M.W.: 493 |
| B3 | Diarylsulfonylurea | 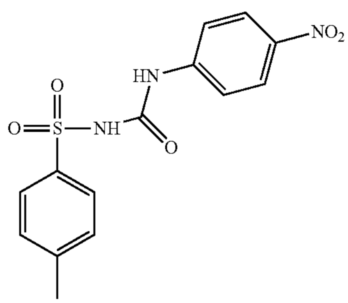 [SMILES: Cc1ccc(S(=O)(=O)NC(=O)Nc2ccc([N+](=O)[O-])cc2)cc1] | Reference #**3<br>Name: DASU-01<br>Potency: Ki >100 microM<br>Solvent: Water or buffer<br>Hints For Use: Useful for CFTR noise anaylsis M.W. 335.3 |
| B4 | (7R,9S)-7,8-dihydroxy-3-(4-hydroxy-5-(hydroxymethyl)tetrahydrofuran-2-yl)-7,9-dimethyl-3,7,8,9-tetrahydropyrimido[1,2-i]purine-9-carboxylic acid | 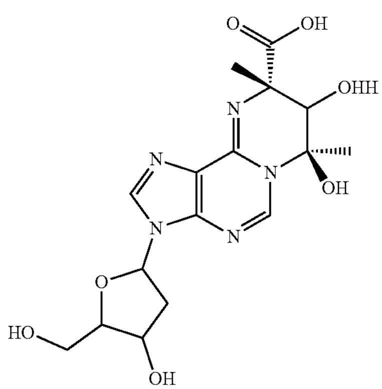 | Reference #**16<br>Name: Blocker 5ab<br>Potency: Ki <100 pM but see Ref. #17<br>Solvent: Water or buffer<br>Hints For Use:<br>M.W. 395.37 |
| B5 | (2S,4R)-3,4-dihydroxy-2,4-dimethyl-3,4-dihydro-2H-pyrimido[2,1-a]isoquinoline-2-carboxylic acid | 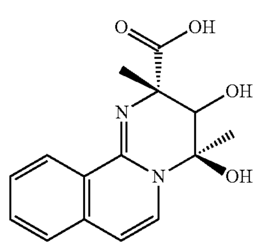 [SMILES: C[C@]1(C(=O)O)N=C2c3ccccc3C=CN2[C@](C)(O)C1O] | Reference #**16<br>Name: Blocker 8ab<br>Potency: Ki <20 nM but see Ref. #17<br>Solvent: Water or buffer<br>Hints For Use:<br>M.W. 288.3 |

TABLE 3-continued

Examples of known drugs for cystic fibrosis

| ID | Chemical Name | Chemical Structure | Comments |
|---|---|---|---|
| B6 | 7,9-dimethyl-11-phenyl-6-(5-methylfuran-2-yl)-5,6-dihydro-pyrimido-[4',5'-3,4]pyrrolo[1,2-a]quinoxaline-8,10-(7H,9H)-dione | 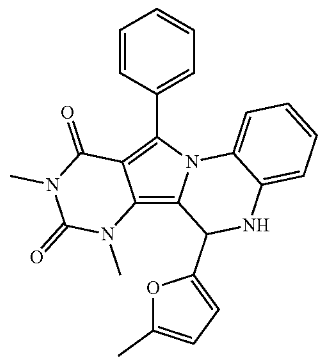 [SMILES: Cc1ccc(C2Nc3ccccc3-n3c(-c4ccccc4)c4c(=O)n(C)c(=O)n(C)c4c32)o1] | Reference #22<br>Name: PPQ-102.<br>Potency Ki = 90 nM<br>Solvent: DMSO<br>Hints for use:<br>M.W. 438.48 |
| B7 | 5-[[4-(2h-tetrazol-5-yl)phenyl]methylene]-2-thioxo-3-[3-(trifluoromethyl)phenyl]-4-thiazolidine | 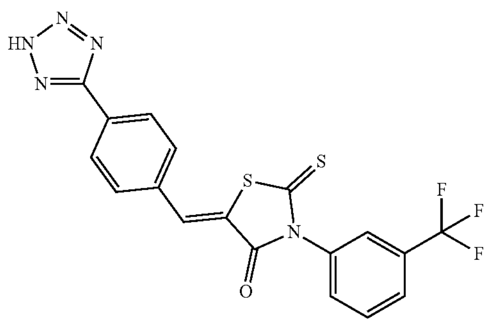 [SMILES: O=C1/C(=C/c2ccc(-c3nn[nH]n3)cc2)SC(=S)N1c1cccc(C(F)(F)F)c1] | Reference #23<br>Name: Tetrazolo-Inh.-172.<br>Potency:<br>Ki ~1 microM<br>Solvent: DMSO<br>Hints for use:<br>Reported to be more water soluble than Inh.-172<br>M.W. 433.43 |
| B8 | 4-[[3-[3-(trifluoromethyl)phenyl]-2,4-dioxo-5-thiazolidinylidene]methyl]benzoic acid | 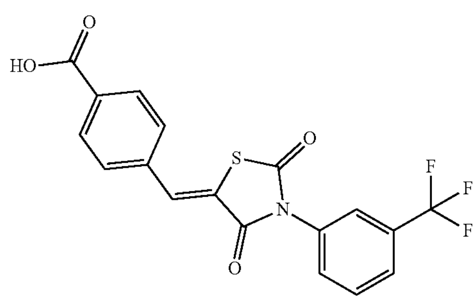 [SMILES: O=C(O)c1ccc(/C=C2\SC(=O)N(c3cccc(C(F)(F)F)c3)C2=O)cc1] | Reference #23<br>Name: Oxo-Inh.-172.<br>Potency:<br>Ki ~1 microM<br>Solvent: DMSO<br>Hints for use:<br>Reported to be more water soluble than Int.-172<br>M.W. 393.34 |
| P1 | 4-Methyl-2-(5-phenyl-1H-pyrazol-3-yl)-phenol | 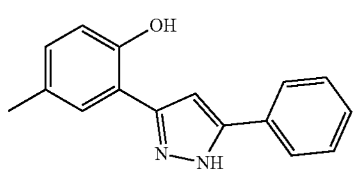 [SMILES: Cc1ccc(O)c(-c2cc(-c3ccccc3)[nH]n2)c1] | Reference #**12 & 15<br>Name: VRT-532<br>Potency: Ks 3 to 5 microM<br>Solvent: DMSO<br>Hints For Use:<br>M.W.: 250 |
| P2 | 2-[(2-1H-Indol-3-yl-acetyl)-methyl-amino]-N-(4-isopropyl-phenyl)-2-phenyl-acetamide | 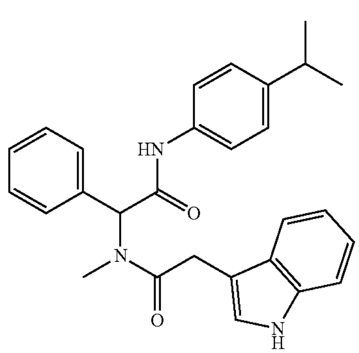 [SMILES: CC(C)c1ccc(NC(=O)C(c2ccccc2)N(C)C(=O)Cc2c[nH]c3ccccc23)cc1] | Reference #**4<br>Name: PG-01<br>Potency: Ks = 300 nM<br>Solvent: DMSO<br>Hints For Use:<br>M.W.: 439.5 |

TABLE 3-continued

Examples of known drugs for cystic fibrosis

| ID | Chemical Name | Chemical Structure | Comments |
|---|---|---|---|
| P3 | 6-(Ethyl-phenyl-sulfonyl)-4-oxo-1,4-dihydro-quinoline-3-carboxylic acid 2-methoxy-benzylamide | 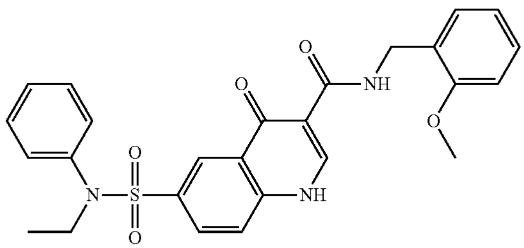 [SMILES: CCN(c1ccccc1)S(=O)(=O)c1ccc2[nH]cc(C(=O)NCc3ccccc3OC)c(=O)c2c1] | Reference #**4 Name: SF-03 Potency: Ks = 30 nM Solvent: DMSO Hints For Use: M.W.: 491.6 |
| P4 | 1-(3-chlorophenyl)-5-trifluoromethyl-3-hydrobenzimidazol-2-one | 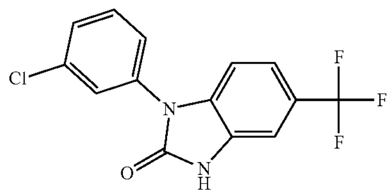 [SMILES: O=c1[nH]c2cc(C(F)(F)F)ccc2n1-c1cccc(Cl)c1] | Reference #**5 Name: UCCF-853 Potency: Ks = 3 microM Solvent: DMSO Hints For Use: M.W.: 312.7 |
| P5 | 2-(2-Chloro-benzoylamino)-4,5,6,7-tetrahydro-benzo[b]thiophene-3-carboxylic acid | 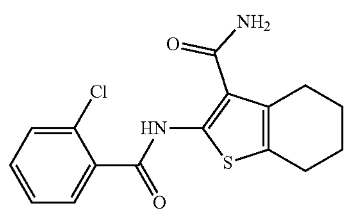 [SMILES: NC(=O)c1c(NC(=O)c2ccccc2Cl)sc2c1CCCC2] | Reference #**6 Name: dF508$_{act}$-02 Potency: Ks = 70 nM Solvent: DMSO Hints For Use: M.W.: 334.8 |
| P6 | 5,7,Dihydroxy-3-(4-hydroxy-phenyl)-chroman-4-one | 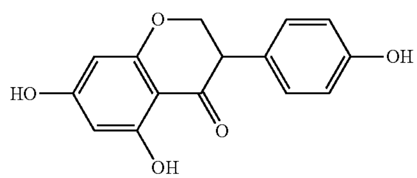 [SMILES: O=C1c2c(O)cc(O)cc2OCC1c1ccc(O)cc1] | Reference #**8 Name: Genistein (discounted-available from Sigma #G6649) Potency: Ks = 10 to 30 microM Solvent: DMSO Hints For Use: M.W.: 272.3 |
| P7 | 1-(5-Chloro-2-hydroxy-phenyl)-5-trifluoromethyl-1,3-dihydro-indol-2-one | 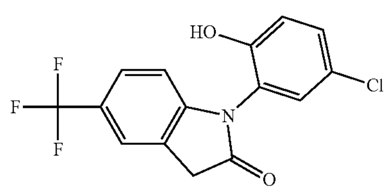 [SMILES: O=C1Cc2cc(C(F)(F)F)ccc2N1c1cc(Cl)ccc1O] | Reference #**8 Name: NSOO4 Potency: EC50 3 microM Solvent: DMSO Hints For Use: Does not work in excised patches. M.W.: 327.7 |
| P8 | 4-(4-Oxo-4H-benzo[h]chromen-2-yl)-pyridinium; bisulfate | 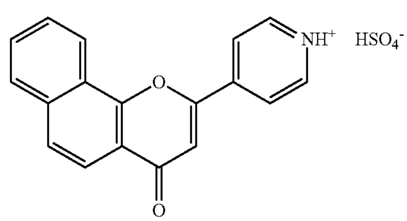 | Reference #**9 and 10 Potency: Ks = 2 microM Solvent: DMSO Hints For Use: M.W.: 371.4 |
| P9 | 3-But-3-ynyl-5-methoxy-1-phenyl-1H-pyrazole-4-carbaldehyde | 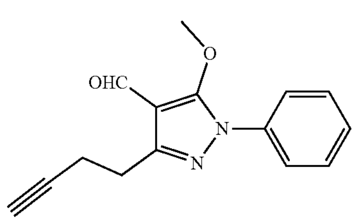 [SMILES: C#CCCc1nn(-c2ccccc2)c(OC)c1C=O] | Reference #**10 Potency: Ks = 10 microM Solvent: DMSO Hints For Use: M.W.: 254.3 |

TABLE 3-continued

Examples of known drugs for cystic fibrosis

| ID | Chemical Name | Chemical Structure | Comments |
|---|---|---|---|
| P10 | 3-(2-Benzyloxy-phenyl)-5-chloromethyl-isoxazole | 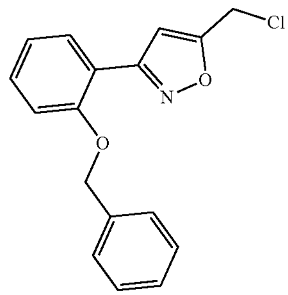 [SMILES: ClCc1cc(-c2ccccc2OCc2ccccc2)no1] | Reference #**10<br>Potency: Ks >50 microM<br>Solvent: DMSO<br>Hints For Use:<br>M.W.: 299.8 |
| C1 | 6-(1H-Benzoimidazol-2-ylsulfanylmethyl)-2-(6-methoxy-4-methyl-quinazolin-2-ylamino)-pyrimidin-4-ol | 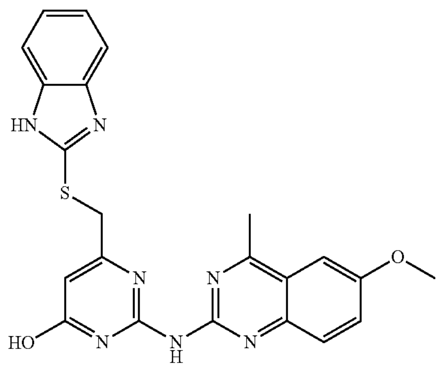 [SMILES: COc1ccc2nc(Nc3nc(O)cc(CSc4nc5ccccc5[nH]4)n3)nc(C)c2c1] | Reference #**11<br>Potency: Ks = 3 microM<br>Solvent: DMSO<br>Hints For Use:<br>M.W.: 445.5 |
| C2 | 2-{1-[4-(4-Chloro-benzenesulfonyl)-piperazin-1-yl]-ethyl}-4-piperidin-1-yl-quinazoline | 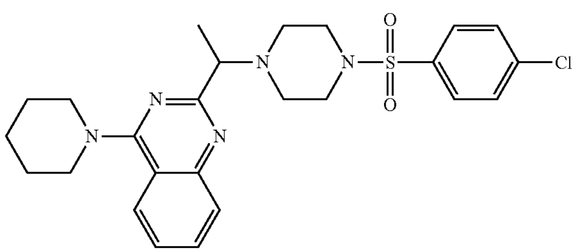 [SMILES: CC(c1nc(N2CCCCC2)c2ccccc2n1)N1CCN(S(=O)(=O)c2ccc(Cl)cc2)CC1] | Reference. Vertex Presentation<br>Name: VRT-640<br>Potency: unknown<br>Solvent: DMSO<br>Hints For Use:<br>Likely binds to serum proteins.<br>M.W.: 500.1 |
| C3 | 4-Cyclohexyloxy-2-{1-[4-(4-methoxy-benzenesulfonyl)-piperazin-1-yl]-ethyl}-quinazoline | 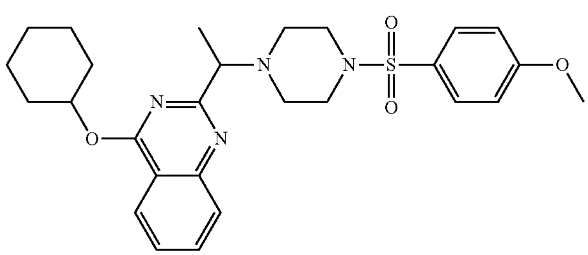 [SMILES: COc1ccc(S(=O)(=O)N2CCN(C(C)c3nc(OC4CCCCC4)c4ccccc4n3)CC2)cc1] | Reference #**12,13, 15<br>Name: VRT-325<br>Potency: EC50 2 microM<br>Solvent: dry DMSO<br>Hints For Use: Binds to serum proteins<br>M.W.: 510.65 |
| C4 | N-[2-(5-Chloro-2-methoxy-phenylamino)-4'-methyl-[4,5']bithiazolyl-2'-yl]-benzamide | 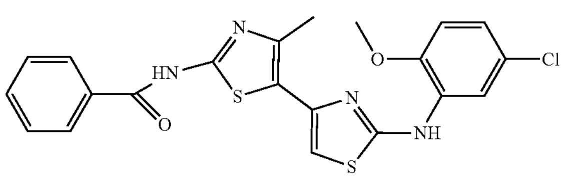 [SMILES: COc1ccc(Cl)cc1Nc1nc(-c2sc(NC(=O)c3ccccc3)nc2C)cs1] | Reference #**11<br>Name: cmpd 4a<br>Potency: EC50 2 microM<br>Solvent: DMSO<br>Hints For Use:<br>M.W.: 440.9 |
| C5 | 4,5,7-trimethyl-N-phenylquinolin-2-amine | 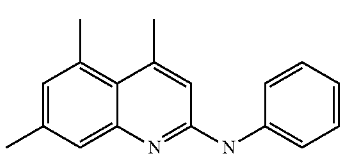 [SMILES: Cc1cc(C)c2c(C)cc(Nc3ccccc3)nc2c1] | Reference #**11:<br>Name: cmpd 5a<br>Potency: EC50 13 microM<br>Solvent: DMSO<br>Hints For Use:<br>M.W.: 262.35 |

TABLE 3-continued

Examples of known drugs for cystic fibrosis

| ID | Chemical Name | Chemical Structure | Comments |
|---|---|---|---|
| C6 | N-(4-bromophenyl)-4-methylquinolin-2-amine | 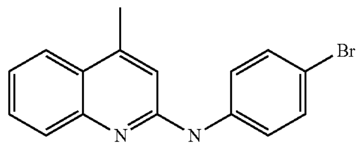 [SMILES: Cc1cc(Nc2ccc(Br)cc2)nc2ccccc12] | Reference #**11: Name: cmpd 5c Potency: EC50 8 microM Solvent: DMSO Hints For Use: M.W.: 313.19 |
| C7 | 2-(4-isopropoxy-picolinoyl)-N-(4-pentylphenyl)-1,2,3,4-tetrahydro-isoquinoline-3-carboxamide | 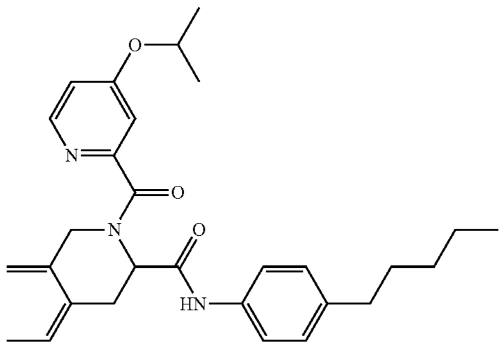 [SMILES: C=C1CN(C(=O)c2cc(OC(C)C)ccn2)C(C(=O)Nc2ccc(CCCCC)cc2)C/C1=C/C] | Reference #**21: Name: Genzyme cmpd 48 only 10 mg will be provided Potency: EC50 300 nM Solvent: DMSO Hints For Use: M.W.: 472.6 |
| C8 | N-(2-fluorophenyl)-2-(1H-indol-3-yl)-2-oxoacetamide | 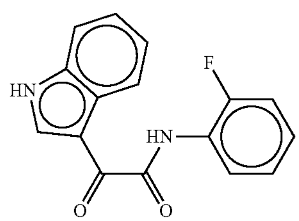 | Reference #** Vertex patent Potency: EC50 Solvent: DMSO Hints For Use: M.W.: 282.27 |
| C9 | 7-chloro-4-(4-(4-chlorophenyl-sulfonyl)piperazin-1-yl)quinoline | 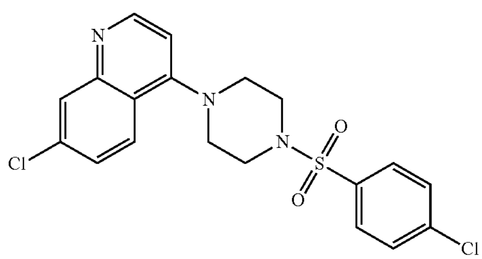 [SMILES: O=S(=O)(c1ccc(Cl)cc1)N1CCN(c2ccnc3cc(Cl)ccc23)CC1] | Reference #**18 Name: KM11060 Potency: EC50 <1 microM Solvent: DMSO Hints For Use: M.W.: 422.33 |
| C10 | 7-chloro-4-(4-(phenylsulfonyl)piperazin-1-yl)quinoline | 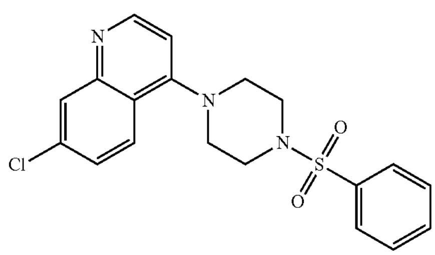 [SMILES: O=S(=O)(c1ccccc1)N1CCN(c2ccnc3cc(Cl)ccc23)CC1] | Reference #18 Name: KM11057 Potency: EC50 >100 microM Solvent: DMSO Hints For Use: Inactive derivative of C9 (KM11060) M.W.: 387.88 |
| C11 | (Z)-N'-(3,4-dihydroxybenzyl-idene)-3-hydroxy-2-naphthohydrazide | 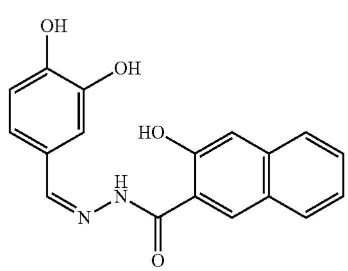 [SMILES: O=C(N/N=C\c1ccc(O)c(O)c1)c1cc2ccccc2cc1O] | Reference #: 19 Name: Dynasore Potency: EC50 10-20 microM Solvent: DMSO Hints For Use: An inhibitor of dynamin, blocks CFTR endocytosis M.W.: 322.31 |

TABLE 3-continued

Examples of known drugs for cystic fibrosis

| ID | Chemical Name | Chemical Structure | Comments |
|---|---|---|---|
| C12 | N-(4-fluorophenyl)-4-p-tolylthiazol-2-amine | 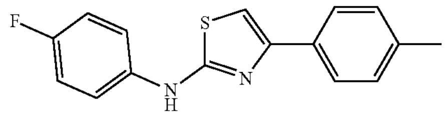 [SMILES: Cc1ccc(-c2csc(Nc3ccc(F)cc3)n2)cc1] | Referenece #: 11<br>Name: 2i<br>Potency: EC50 5 microM<br>Solvent: DMSO<br>Hints For<br>M.W.: 284.35 |
| C13 | N-(2-(3-acetylphenylamino)-4'-methyl-4,5'-bithiazol-2'-yl)benzamide | 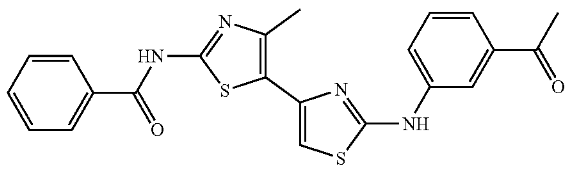 [SMILES: CC(=O)c1cccc(Nc2nc(-c3sc(NC(=O)c4ccccc4)nc3C)cs2)c1] | Reference #: 11<br>Name: 4c<br>Potency: EC50 2 microM<br>Solvent: DMSO<br>Hints For<br>M.W.: 434.53 |
| C14 | N-(2'-(2-methoxyphenyl-amino)-4-methyl-5,5'-bithiazol-2-yl)benzamide | 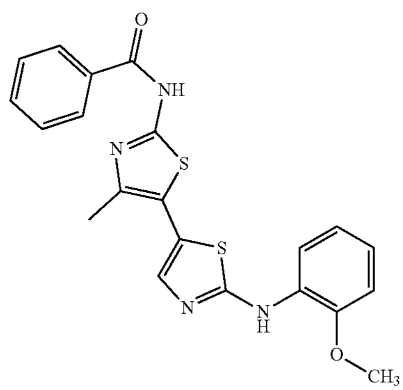 [SMILES: COc1ccccc1Nc1ncc(-c2sc(NC(=O)c3ccccc3)nc2C)s1] | Reference #: 11<br>Name: 4d<br>Potency: EC50 7 microM<br>Solvent: DMSO<br>Hints For Use:<br>M.W. 422.52 |
| C15 | N-phenyl-4-(4-vinylphenyl)thiazol-2-amine | 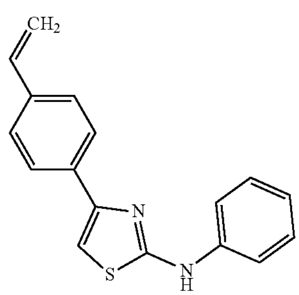 [SMILES: C=Cc1ccc(-c2csc(Nc3ccccc3)n2)cc1] | Reference #: 11<br>Name: 2b<br>Potency: EC50 16 microM<br>Solvent: DMSO<br>Hints<br>M.W. 278.37 |
| C16 | 2-(6-methoxy-4-methylquinazolin-2-ylamino)-5,6-dimethylpyrimidin-4(1H)-one | 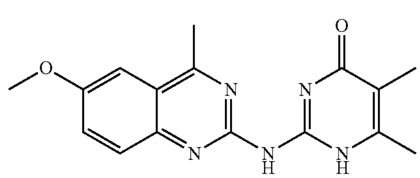 | Reference #: 11<br>Name: 3d<br>Potency: EC50 15 microM<br>Solvent: DMSO<br>Hints<br>M.W.: 311.34 |
| C17 | N-(2-(5-chloro-2-methoxyphenyl-amino)-4'-methyl-4,5'-bithiazol-2'-yl)pivalamide | 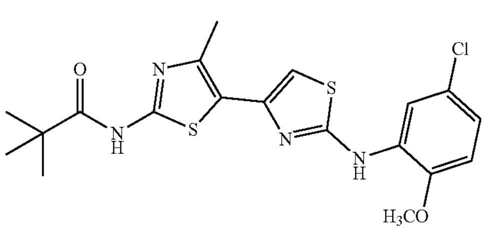 [SMILES: COc1ccc(Cl)cc1Nc1nc(-c2sc(NC(=O)C(C)(C)C)nc2C)cs1] | Reference #: 20<br>Name: 15Jf<br>Potency: EC50 1-2 microM<br>Solvent: DMSO<br>Hints For Use:<br>M.W.: 436.98 |

TABLE 3-continued

Examples of known drugs for cystic fibrosis

| ID | Chemical Name | Chemical Structure | Comments |
|---|---|---|---|
| C18 | 1-(benzo[d][1,3]dioxol-5-yl)-N-(5-((2-chlorophenyl)(3-hydroxypyrrolidin-1-yl)methyl)thiazol-2-yl)cyclopropane carboxamide | 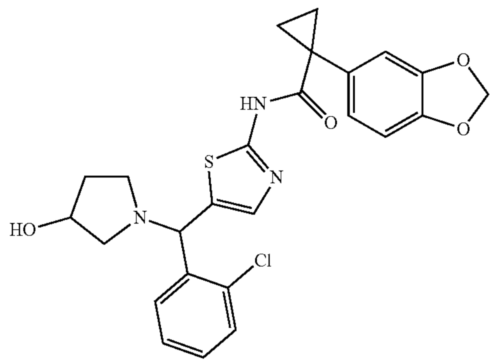 [SMILES: O=C(Nc1ncc(C(c2ccccc2Cl)N2CCC(O)C2)s1)C1(c2ccc3c(c2)OCO3)CC1] | Reference #24<br>Name: CF-106951<br>Potency Ks ~0.6 microM<br>Solvent: DMSO<br>Hints for use: Use at 3 to 6 microM for maximum effect.<br>M.W. 497.99 |

Blocker (B); Potentiator (P); Corrector (C); Trafficking (T)

TABLE 4

Compounds used to treat other diseases characterised in that they impact fluid secretion

| Compound | Mechanism | Human application |
|---|---|---|
| salbutamol | b2-adrenergic receptor stimulation | bronchodilation for asthma* |
| salmeterol | b2-adrenergic receptor stimulation | bronchodilation for asthma* |
| Viagra or related compounds | phosphodiesterase inhibitor | facilitates male erections |
| Bortezimib or other Proteasomal inhibitors | proteasomal inhibition | anti-tumourigenic |
| Trichostatin A | HDAC inhibitor | anti-schizophrenic |
| loperamide | modulation of intestinal fluid secretion | anti-diarrhoea |
| bismuth subsalicylate | modulation of intestinal fluid secretion | anti-diarrhoea |

*Other bronchodilators include: Albuterol (salbutamol), Alupent, Levalbuterol, Pirbuterol, Advair and Symbicort, Serevent (salmeterol), Foradil (formoterol), Perforomist Examples of known CFTR drugs that could be used in an assay for personalised medicine include CFTR correctors and potentiators, such as those listed in Table 3 and/or Table 4 and/or VRT-325, VX809, VX770, 08 (cftrfolding.org) and/or corr-4a. For example, in one embodiment the assay comprises the step of preincubation of cystic fibrosis organoids with CFTR correctors or potentiators, such as VRT-325, VX809, VX770, 08 (cftrfolding.org) and corr-4a. It is to be understood that when this preincubation results in enhanced swelling and/or enhanced forskolin-induced swelling of the organoids, this demonstrates that the correctors have successfully restored CFTR function. Drugs identified by drug screening using the assay of the invention can also be used in an assay for personalised medicine. Such drugs are described in the drug screening section above.

In some embodiments, the invention provides an assay of the invention for use in comparing the activity of drugs between different patients in vitro to assess individual responses to CFTR-restoring drugs for patient-tailored personalized medicine purposes.

In some embodiments, the assay for use in personalised medicine, is used to test individual patient response to drugs wherein the disease of interest is cystic fibrosis, and wherein the assay comprises stimulation of one or more organoids derived from a patient of interest with a compound which is capable of inducing swelling of the organoids;

stimulation of the one or more organoids with a drug known to affect CFTR function or with a drug being tested for its efficacy in affecting CFTR function; and imaging of the one or more organoids, and optionally comparing the swelling of the organoid to the swelling of an organoid which has been stimulated with the compound but has not been stimulated with the drug;

wherein an increase in swelling of the one or more organoids in response to stimulation by a drug indicates that the patient is responsive to treatment with the drug.

Examples 2 and 3 clearly demonstrate that forskolin-induced swelling can be restored by drugs with known CFTR-restoring capacity. Interestingly, it was observed that drug responses of organoids are variable between CF patients, even between F508del-CFTR homozygous organoids. This raises the possibility that this in vitro assay may predict in vivo drug-responsiveness of individual patients. An ideal therapeutic model for CF would be to screen effectiveness of available CFTR-restoring drugs directly after CF diagnosis to optimize treatment at the personal level before disease onset. Personalized medicine approaches may also facilitate the development and approval of drugs to which only subgroups of patients respond, and limit the economic risks associated with drug research. Furthermore, the assay of the invention can be used for approval of drugs in patients that are genotypically mismatched with drugs that have been validated for a specific CFTR-genotype. Interim phase II results of a current trial published on websites of the North American Cystic Fibrosis Foundation (cff.org) and Vertex (vrtx.com) indicate that drug-responses to VX-809 and VX770, or VX-770 monotreatment[14], in CFTR F508del subjects are highly variable between patients.

Thus, the invention also provides the use of one or more organoids for the assessment of the responsiveness to a particular treatment option, wherein the assessment comprises use of an assay according to the invention and wherein organoid swelling is indicative of successful treatment.

The invention also provides a method of treating a disease or affliction, comprising the use of the assay of the invention for identifying a drug for the disease or an affliction that a patient is responsive to, and treating the patient with said drug. In some embodiments, the drug is any known or putative drug for treating a disease or affliction associated with fluid uptake or secretion (see section on diseases or affliction which lists diseases or afflictions that apply equally to this section). In some embodiments, the drug is a known or putative drug for cystic fibrosis, bacterially induced diarrhoea (e.g. enterohemorrhagic *E. coli* or caused by cholera toxins or other bacterial toxins); rotavirus infection; adrenoleukodystrophy; asthma, Tangier disease; multi-drug resistance (many cancers, as well as some antibiotic resistant bacteria); obstetric cholestasis, COPD, smoking, sinusitis, pancreatic insufficiency, pancreatitis, infertility, malnutrition, inflammatory diseases, renal disease including polycystic kidney disease, allergic disease, osteoporosis, diabetics, hypertension, hypotension, pathogen-induced diarrhoea (cholera, *E. coli*), 'drying out', liver cirrhosis, malfunction of liver, tumorigenesis. In some embodiments, the drug is any drug listed in Table 3 and/or Table 4.

In some embodiments, computer- or robot-assisted culturing and data collection methods are employed to increase the throughput of the screen.

In some embodiments, the organoid is obtained from a patient biopsy. In some embodiments, the candidate molecule that causes a desired effect on the organoid is administered to said patient.

FIGURES

FIG. 1 shows rapid volumetric expansion and return to baseline morphology was observed when organoids were stimulated with forskolin for 30 min and upon forskolin removal by washing (two representative examples). This indicates that rapid volumetric expansion or decrease can be a measure for fluid (or electrolyte) secretion or absorption, respectively, via the apical membrane. Forskolin was used as CFTR activator, suggestive for a role for this channel in fluid secretion.

FIG. 2 shows RNA was prepared from human organoids and CFTR expression was assessed by quantitative RT-PCR. A cycle threshold for CFTR of 23 indicates high expression of CFTR. b2m and GAPDH were positive controls for the procedure.

FIG. 3 shows volumetric expansion in murine organoids is CFTR dependent. Volumetric growth of organoids is measured by measurement of total organoid surface area upon incubation with forskolin for indicated time points. Preincubation of organoids with CFTR inhibitors CFTRinh172, GIyH-101 or combined was performed for 1 hour.

FIGS. 4A and 4B show volumetric expansion in organoids is CFTR dependent. FIG. 4A shows volumetric growth of human organoids upon incubation with forskolin for indicated time points. Differential interference contrast and calcein-green fluorescent images of a representative example are shown. FIG. 4B shows relative increase of volumetric expansion upon forskolin incubation is inhibited by preincubation of organoids with CFTR inhibitors CFTRinh172, GIyH-101 or combined. Volumetric expansion is monitored by measurement of surface area of the organoid in time by live confocal microscopy.

FIG. 5A shows forskolin-induced expansion of organoid surface area is absent in a cystic fibrosis (CF) patient but present in a healthy control (HC). FIG. 5B shows 24 hours preincubation of CFTR correctors that help to fold the CFTR protein (VRT-325+corr-4a) increase forskolin-inducing swelling of organoids a CF patient.

FIG. 6A shows murine organoids from CFTR-F508del mice show some CFTR-dependent forskolin-induced swelling (FIS) that can be increased with CFTR-restoring compounds (VRT-325). CFTR inhibition as previously described reduces FIS in murine CFTR-F508del before or after CFTR restoration. FIG. 6B shows increased FIS in murine CFTR F508del organoids by compounds VRT-325, Corr 4a or their combination. FIG. 6C shows increased FIS in murine CFTR F508del organoids by incubation of cells at low temperature (27C, 24 hours). FIG. 6D shows strong Forskolin-induced swelling in murine wild type organoids is absent in murine organoids deficient for CFTR.

Figure 10A:
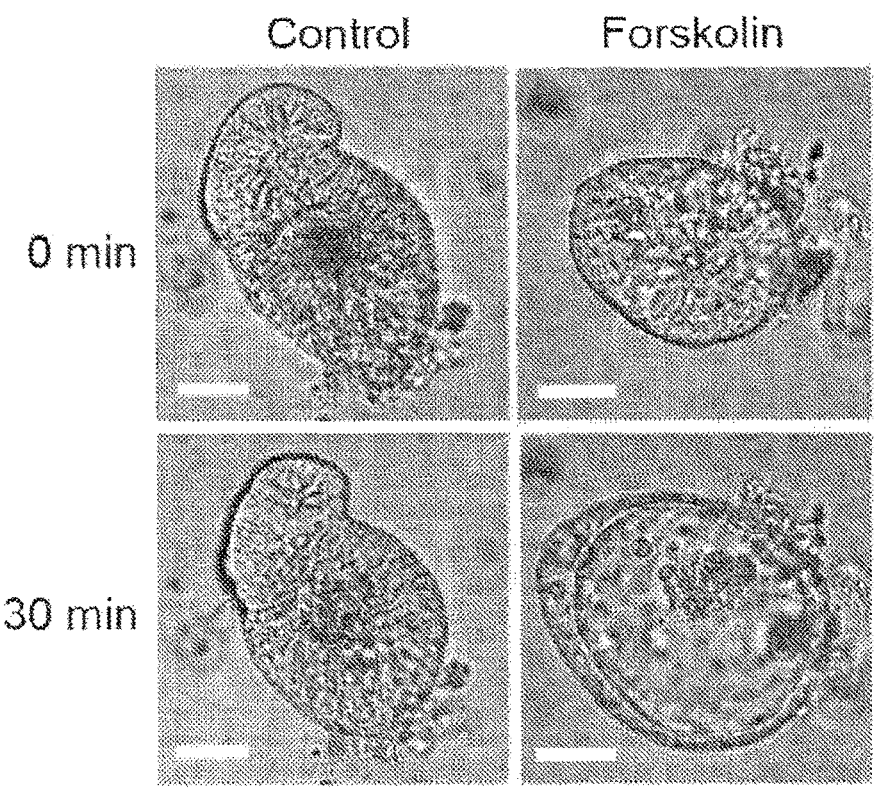
Figure 10B:
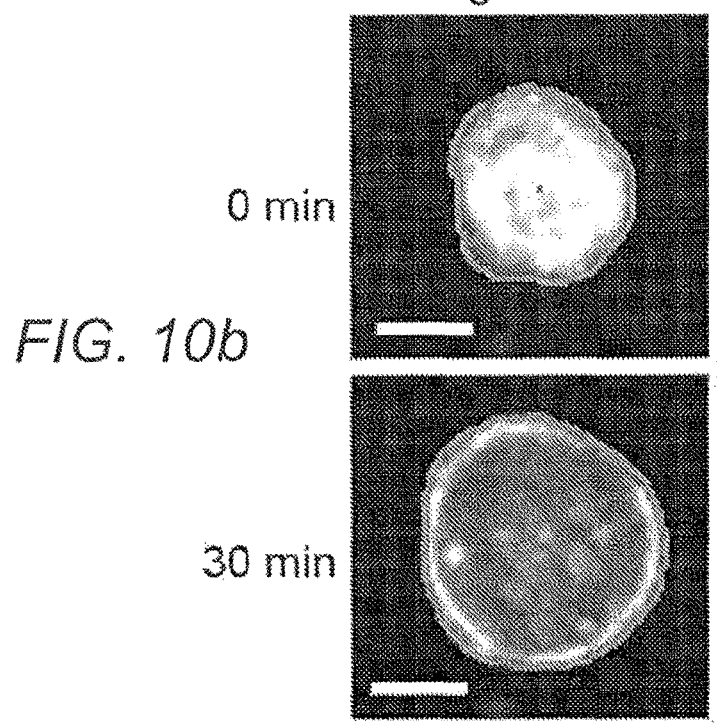
Figure 10C:
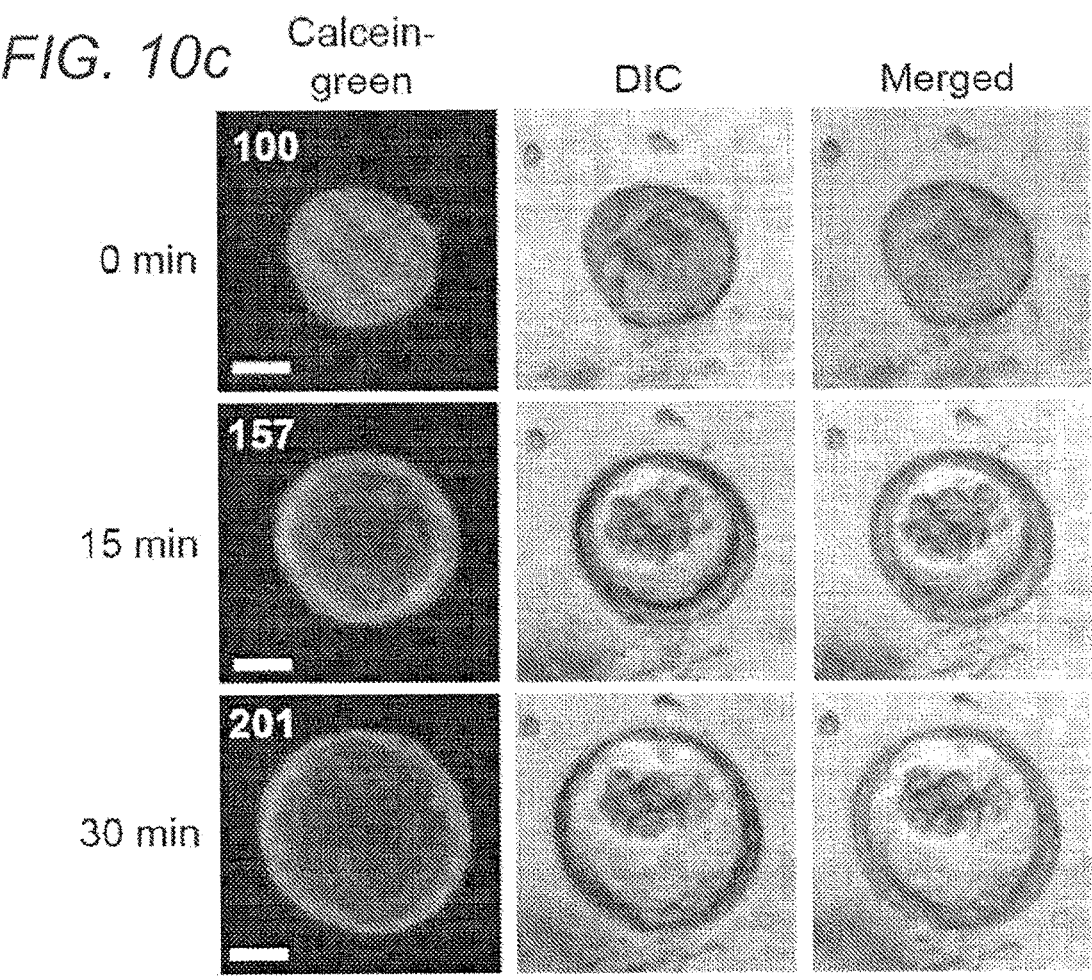
Figure 10D:
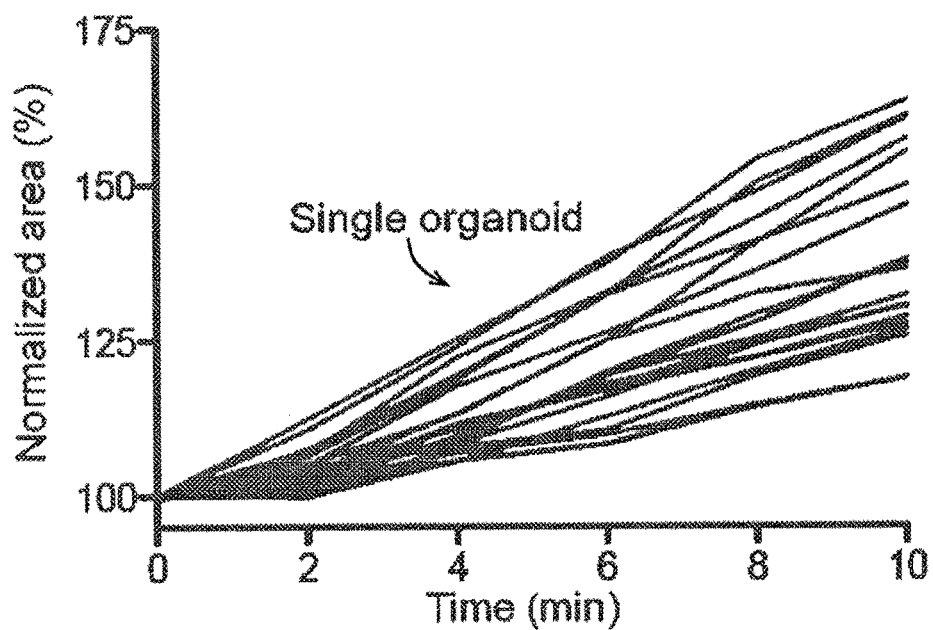
Figure 10E:
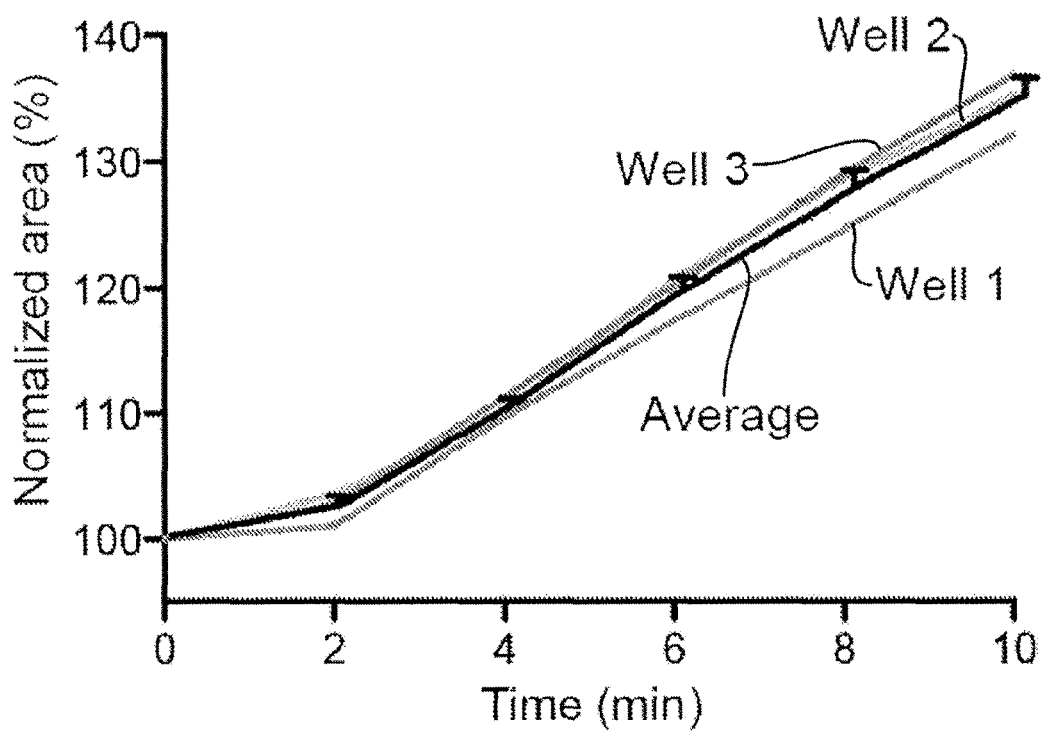
Figure 10F:
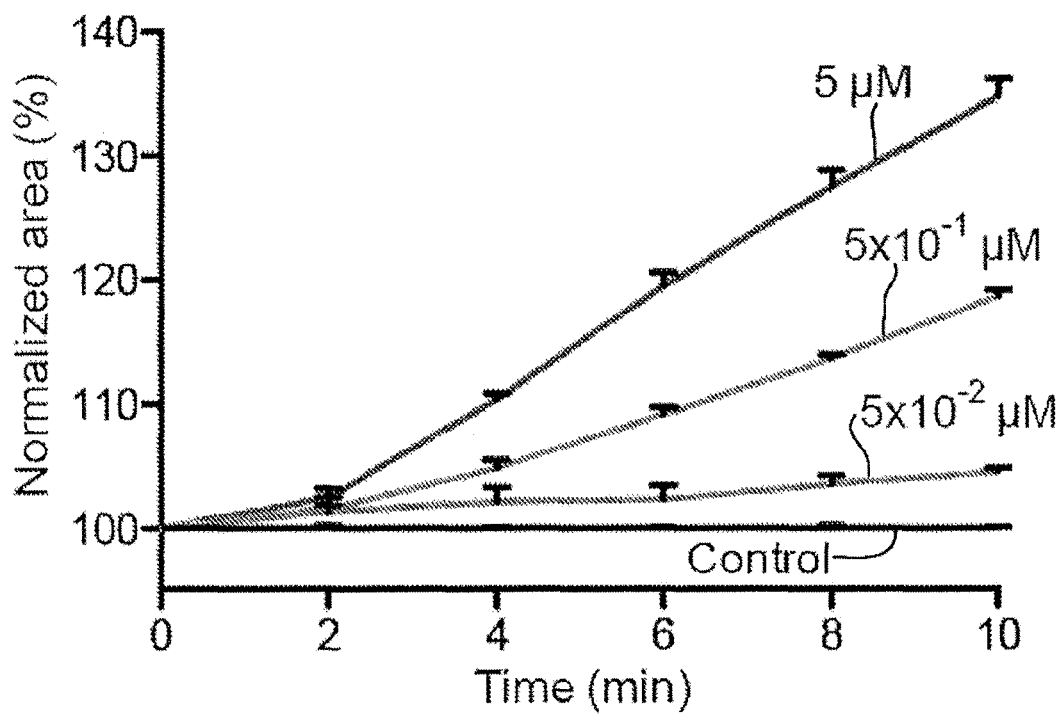

FIGS. 10A to 10F show quantification of forskolin-induced murine organoid swelling. FIG. 10A shows light microscopy analysis of organoids stimulated with forskolin or DMSO. Representative examples for the indicated time points after start of stimulation are shown. FIG. 10B shows fluorescence confocal image of a calcein-green-labeled organoid with object recognition (green line) by image analysis software. FIG. 10C shows representative example of a forskolin-stimulated calcein-green-labeled organoid. Differential interference contrast (DIC) and fluorescence was imaged using live cell confocal microscopy. Surface area relative to t=0 is indicated in the top-left corner. FIG. 10D shows the surface area relative to t=0 (normalized area) of all responding individual organoids from a single well. FIG. 10E shows the total organoid surface area normalized to T=0 from three independent wells. The average response of the individual wells is indicated in black (mean±s.e.m). FIG. 10F shows dose-dependent increase of surface area by forskolin. Each line represents the average response from three individual wells as illustrated in FIG. 10E (mean±s.e.m). Scale bars in FIGS. 10A to 10C are 30 µm. All results are representative for at least three independent experiments.

Figure 11A:
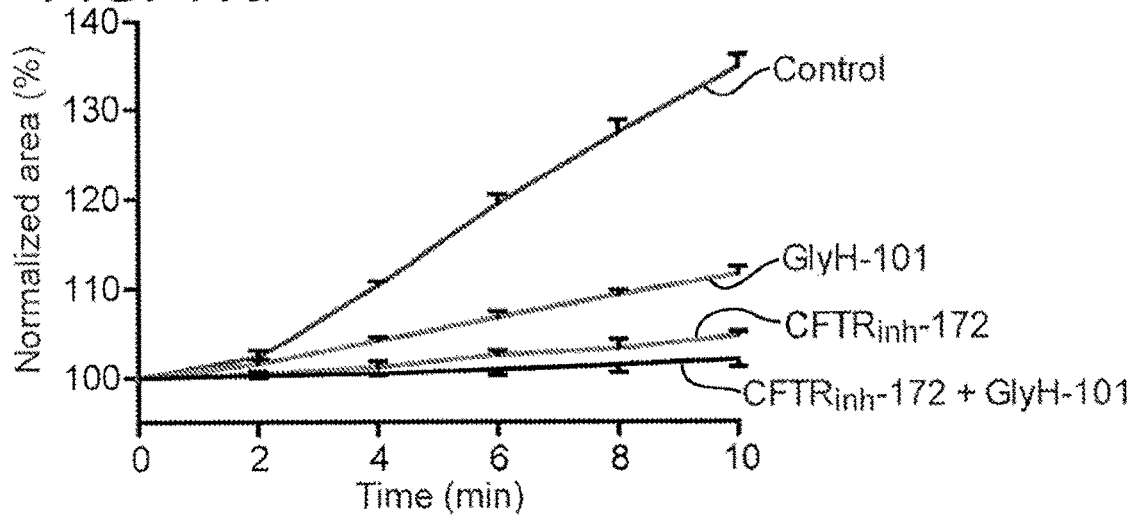
Figure 11B:
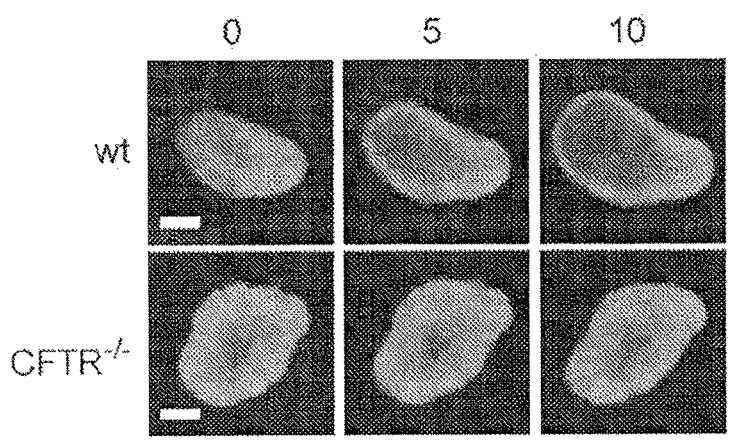
Figure 11C:
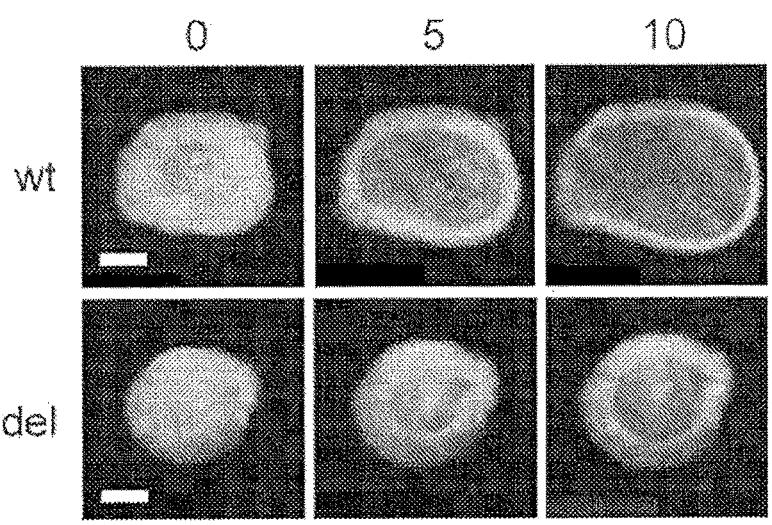
Figure 11D:
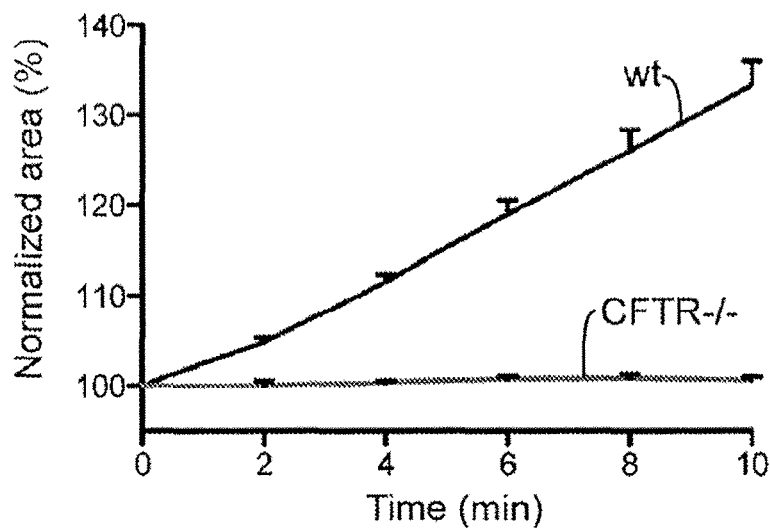
Figure 11E:
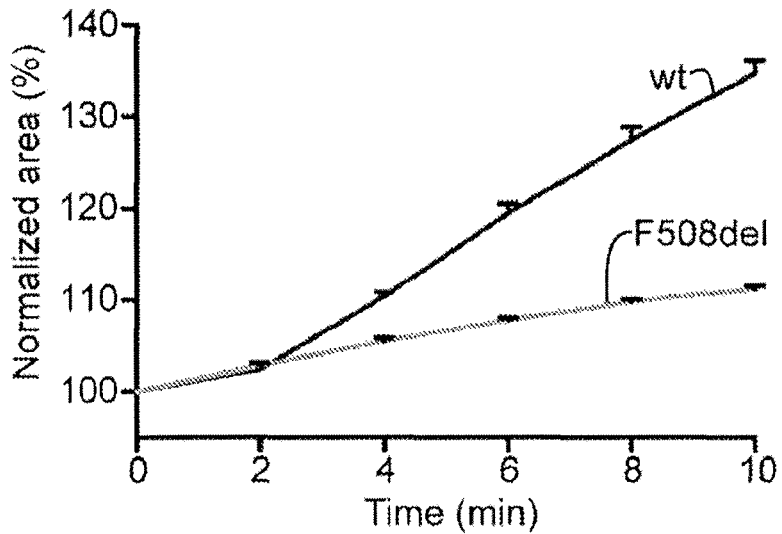
Figure 11F:
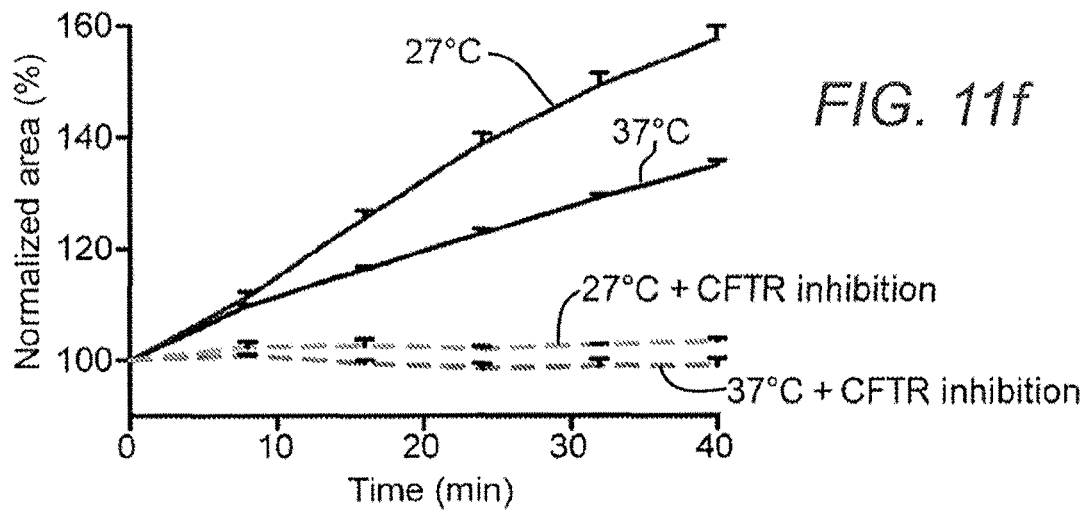

FIGS. 11A to 11G show forskolin-induced swelling of murine organoids is CFTR dependent. FIG. 11A shows normalized swelling curves of forskolin-stimulated calcein-green-labeled organoids pre-incubated with DMSO, CFTR-$_{inh}$172, GIyH-101 or both CFTR-$_{inh}$172 and GIyH-101 (mean±s.e.m.). FIGS. 11B and 11C show representative confocal microscopy images of calcein-green labeled CFTR-deficient (FIG. 11B) or F508del-CFTR (FIG. 11C) organoids and their corresponding wild-types in response to forskolin. Scale bars 50 µm. FIGS. 11D and 11E show quantification of forskolin-induced swelling in CFTR-deficient (FIG. 11D) or F508del-CFTR (FIG. 11E) organoids and their corresponding wild-types (mean±s.e.m.) FIG. 11F shows forskolin-induced swelling of calcein-green labeled F508del-CFTR organoids cultured for 24 hours at 37° C. or 27° C. with or without CFTR inhibition (mean±s.e.m.). Note that the timescale in f+g is larger.

Figure 11G:
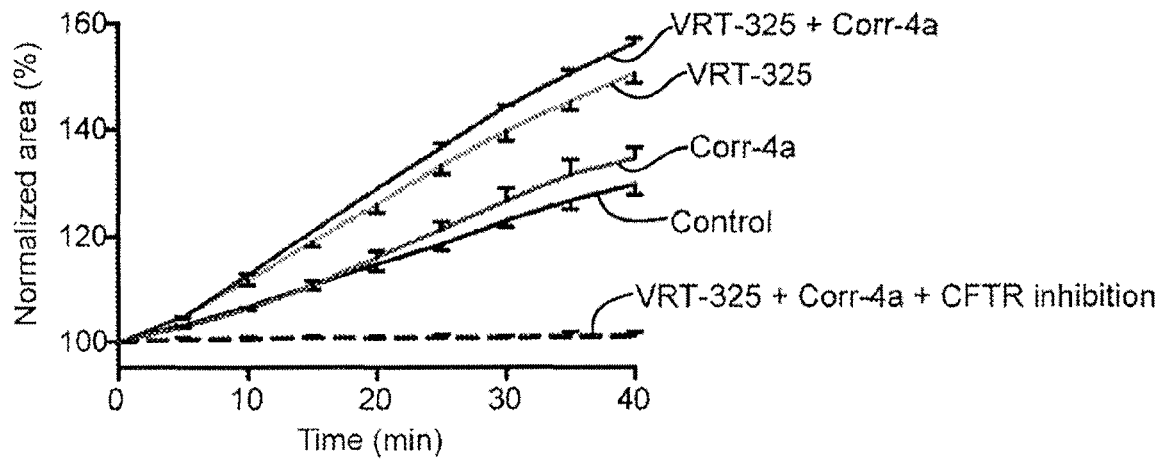

FIG. 11G shows formalized forskolin-induced swelling of F508del-CFTR organoids pre-treated for 24 hours with DMSO, VRT-325, Corr-4a or both correctors with or without CFTR inhibition (mean±s.e.m.). All results are representative for at least three independent experiments.

Figure 12A:
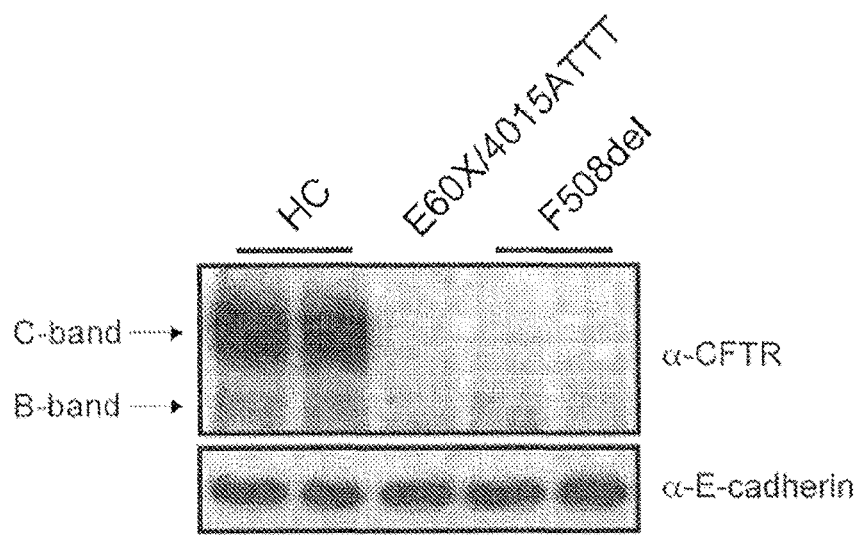
Figure 12A:
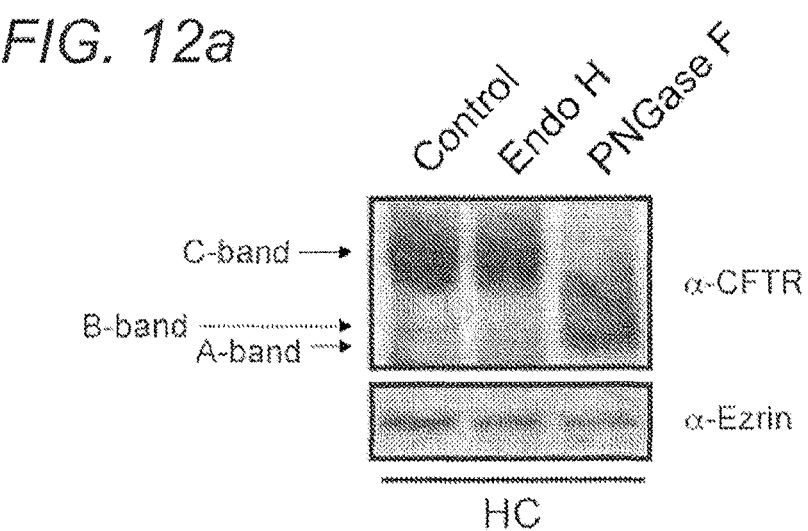
Figure 12B:
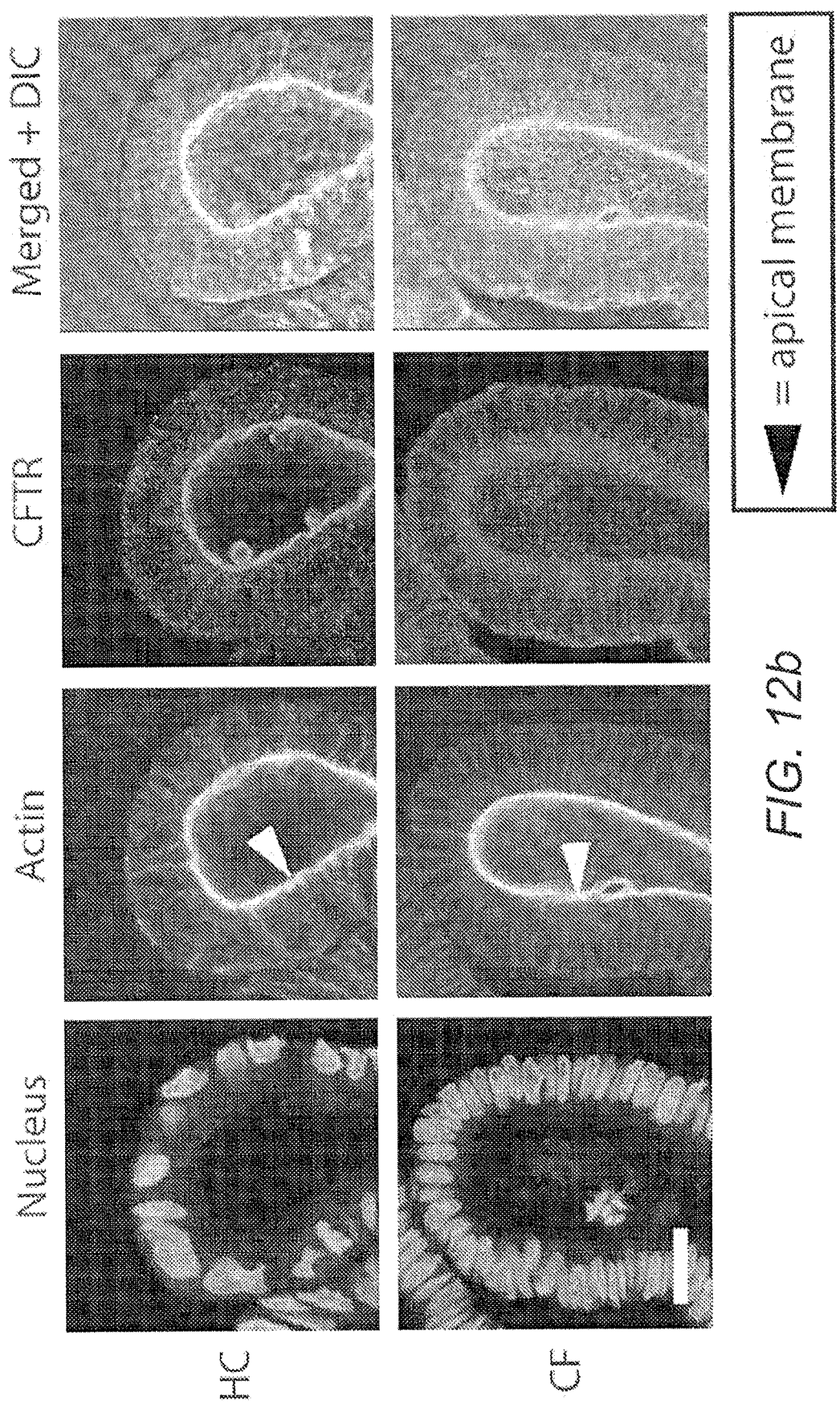
Figure 12C:
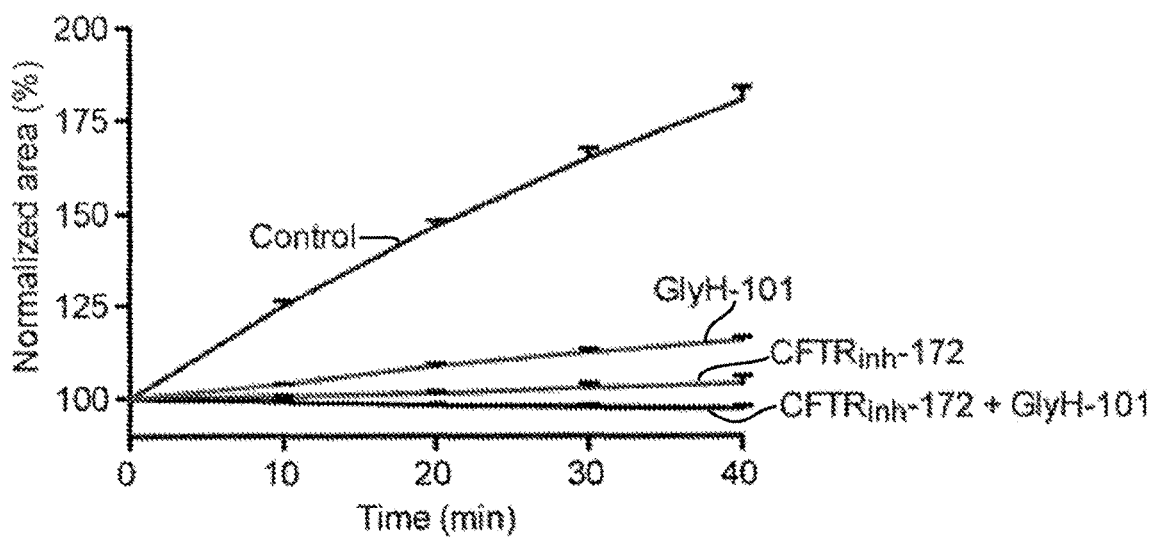
Figure 12D:
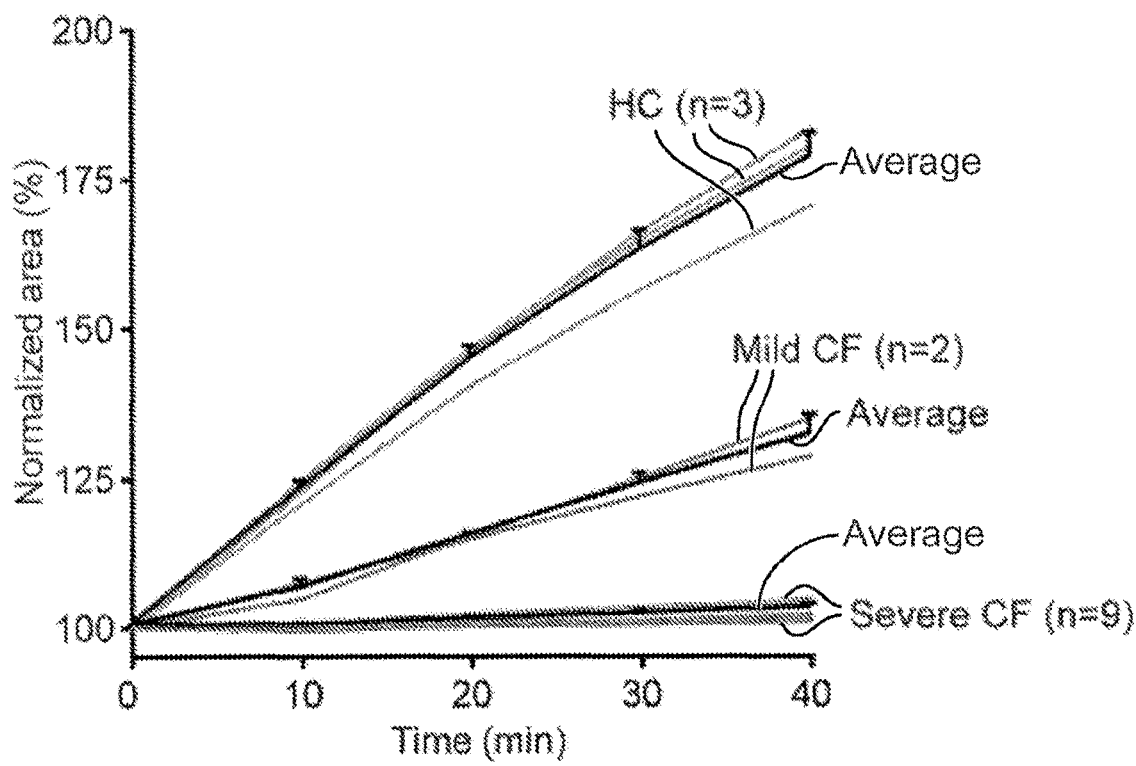

FIGS. 12A to 12F show forskolin-induced swelling in human organoids is CFTR dependent. FIG. 12A shows Western blot analysis of CFTR and E-cadherin (loading control) expression in human rectal HC (n=2), E60X/4015delATTT (n=1), or homozygous F508del-CFTR organoids (n=2; upper panel) and CFTR and ezrin (loading control) expression in whole cell lysates of human rectal organoids that were either not treated (control) or treated with the deglycosylation enzymes Endo H or PNGase F (lower panel). FIG. 12B shows CFTR detection by M3A7 in a rectal HC or F508del-CFTR organoid, costained with phalloidin-FITC (actin) and DAPI (nucleus). Differential interference contrast (DIC) and fluorescence was imaged using live cell confocal microscopy. Scale bars: 20 µm. FIG. 12C shows quantification of forskolin-induced healthy control organoid swelling pre-incubated with DMSO, $CFTR_{inh}$-172, GlyH-101 or both $CFTR_{inh}$-172 and GlyH-101 (mean±s.e.m.). FIG. 12D shows forskolin-induced swelling of rectal organoids derived from 3 individual healthy controls, 2 patients with a mild CF genotype (F508del/A455E) and 9 patients with a severe CF genotype (1× E60X/4015ATTTdel; 1× F508del/G542X; 1× F508del/L927P; 6× F508del/F508del). Average swelling of the different groups is indicated in black (mean±s.e.m.).

Figure 12E:
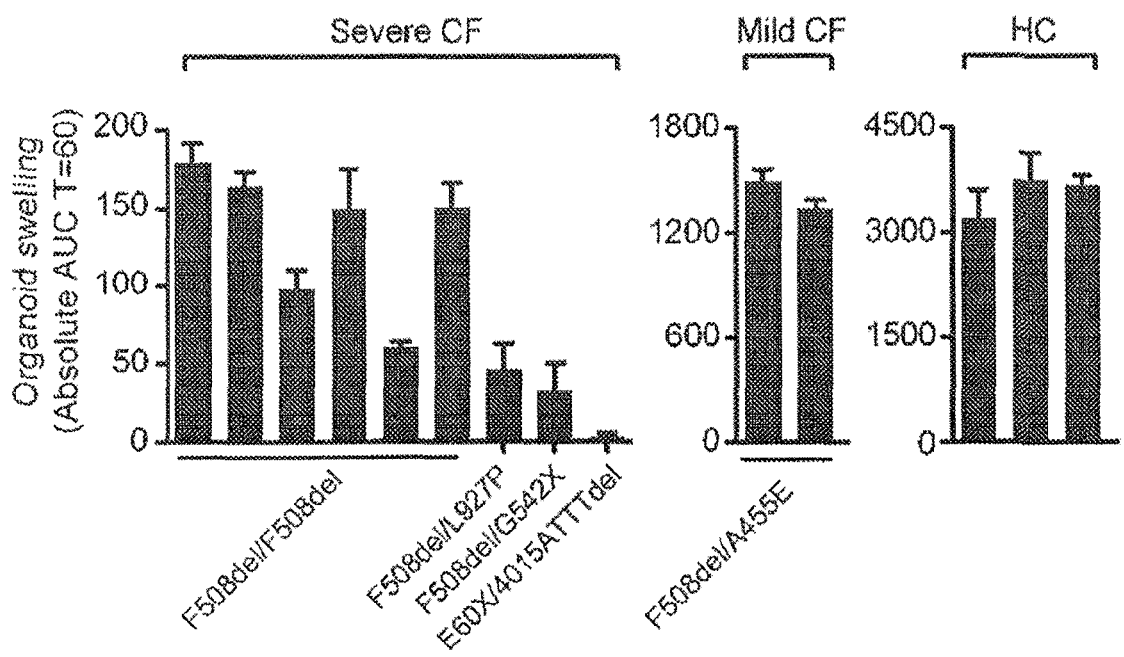
Figure 12F:
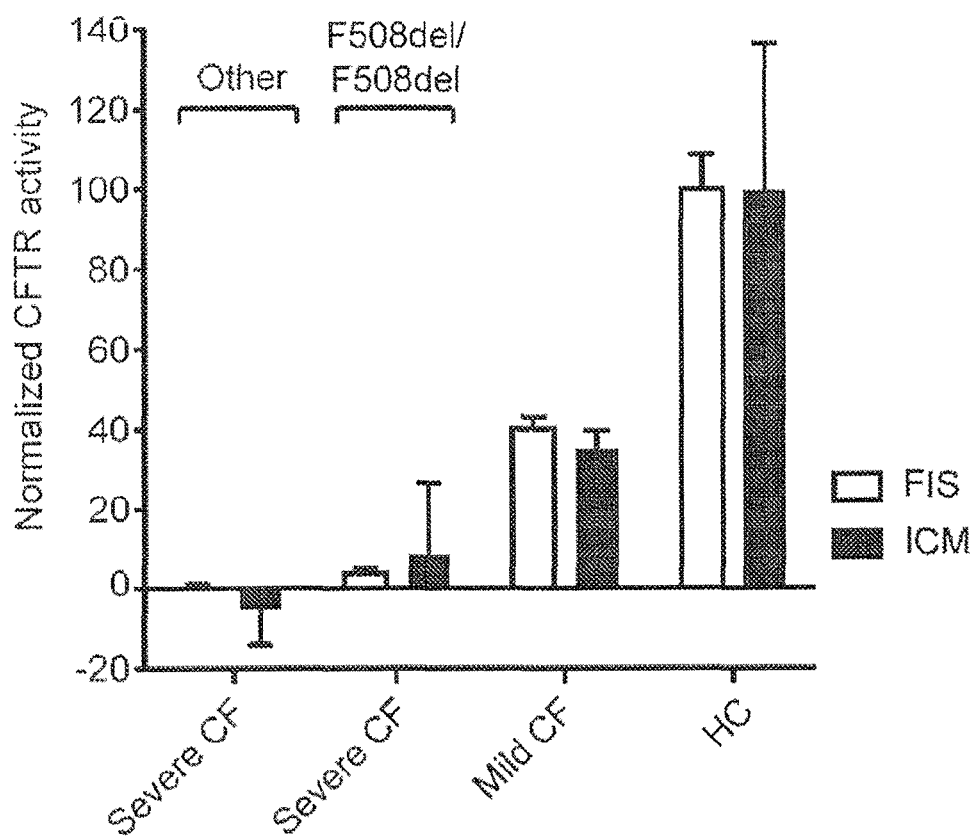

FIG. 12E shows FIS responses of HC or CF organoids expressed as absolute area under the curve (AUC) calculated from time lapses as illustrated in FIG. 12D (baseline=100%, T=60 min). Each bar represents AUC values averaged from at least three independent experiments per individual (mean±s.e.m.). FIG. 12F shows comparison of CFTR activity measured by FIS of HC or CF organoids or by intestinal current measurements (ICM) of the corresponding rectal biopsies. The ICM bars of the different indicated groups represent forskolin-induced CFTR-dependent cumulative chloride secretion ($\rho Amp/cm^2$) relative to the average HC response (set at 100%) and the FIS bars represent forskolin-induced swelling expressed as area under the curve (AUC) averaged from at least three independent experiments per individual as illustrated in FIG. 12F relative to the average HC response (100%). (HC n=3; mild CF n=2; severe CF (F508del/F508del) n=5; severe CF (Other; E60X/4015AT-TTdel and F508del/G542X) n=2; mean±s.d.). All results are representative for at least three independent experiments. ICMs were performed on 4 rectal biopsies.

Figure 13A:
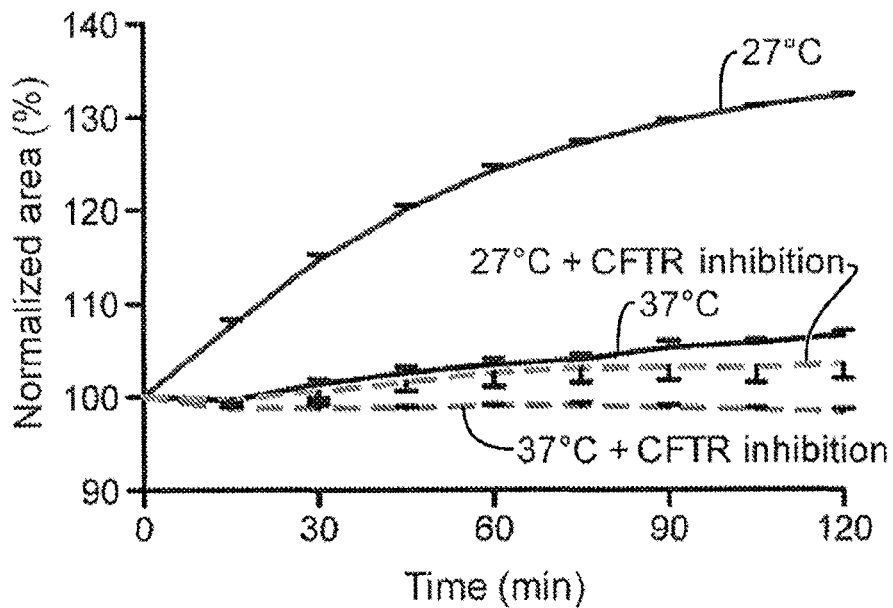
Figure 13B:
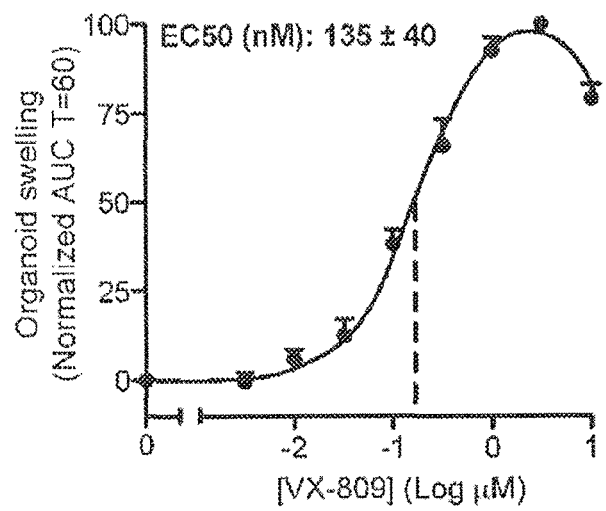
Figure 13B:
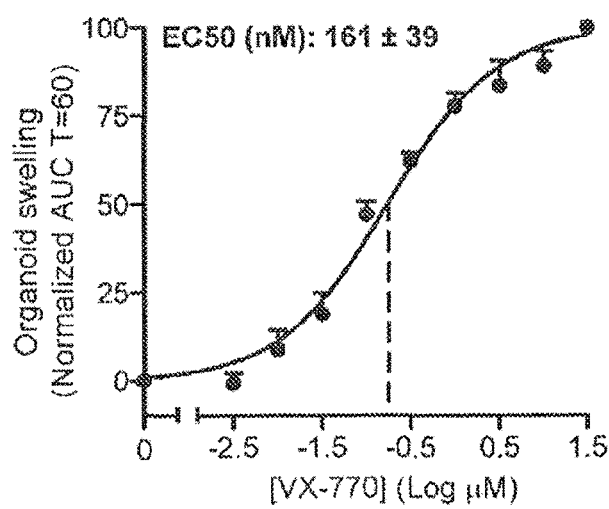
Figure 13D:
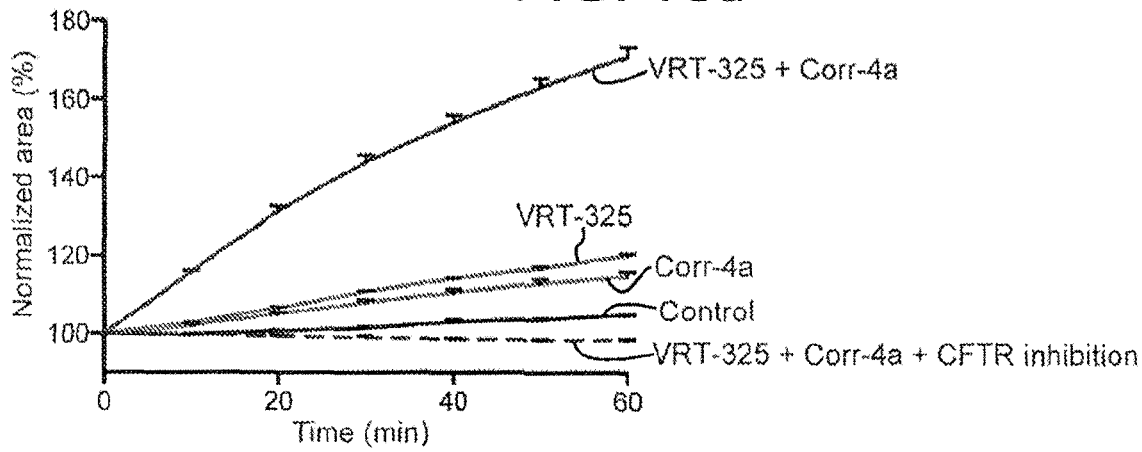
Figure 13E:
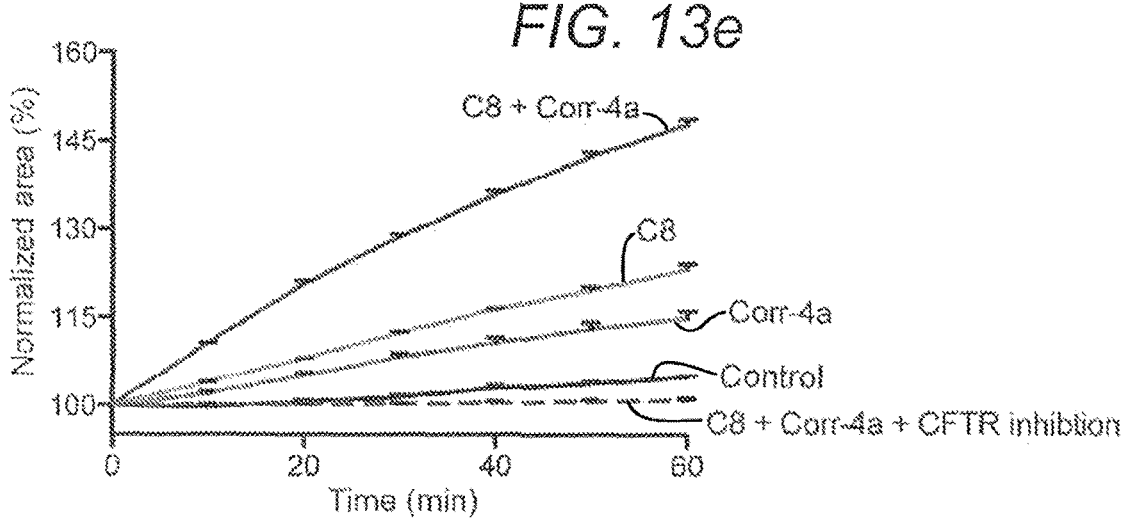
Figure 13F:
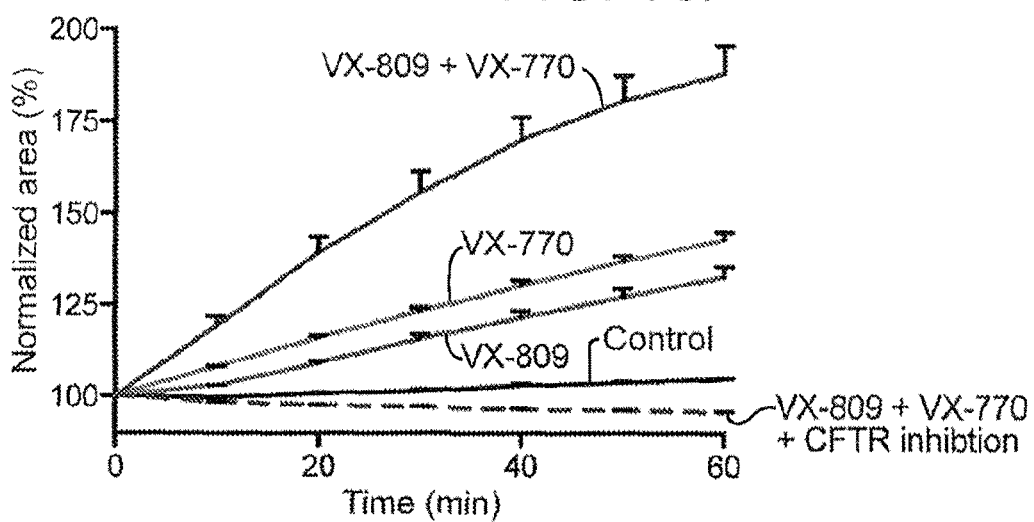

FIGS. 13A to 13F show chemical CFTR correction in human rectal CF organoids. FIG. 13A shows normalized swelling of forskolin-induced calcein-green labeled F508del-CFTR organoids cultured for 24 hours at 37° C. or 27° C. with or without CFTR inhibition (mean±s.e.m.). FIG. 13B shows EC50 of F508del organoids for VX-809 or VX-770. The lines represent FIS expressed as area under the curve (AUC; baseline 100%, T=60 min) calculated from time lapses as presented in FIG. 13F relative to DMSO (0%) treated and VX-809 log(0.5) µM or VX-770 log(1.5) µM (100%) treated organoids. (n=6 F508del homozygous organoids; mean±s.e.m.) FIG. 13C shows representative confocal microscopy images of calcein-green labeled healthy control (HC) or F508del-CFTR organoids in response to forskolin upon pharmacological restoration of CFTR. Scale bars 100 µm. FIGS. 13D to 13F show time lapses of normalized forskolin-induced swelling of F508del-CFTR organoids pre-treated for 24 hours with DMSO, VRT-325 (10 µM), Corr-4a (10 µM), or both correctors with or without CFTR inhibition (FIG. 13D), with DMSO, C8 (10 µM), Corr-4a (10 µM), or both correctors with or without CFTR inhibition (FIG. 13E) or stimulated with the corrector VX-809 (24 h pre-treatment, 3 µM), the potentiator VX-770 (simultaneous with forskolin, 3 µM) or combined compound treatment with or without CFTR inhibition (FIG. 13F) (mean±s.e.m.).

Figure 14A:
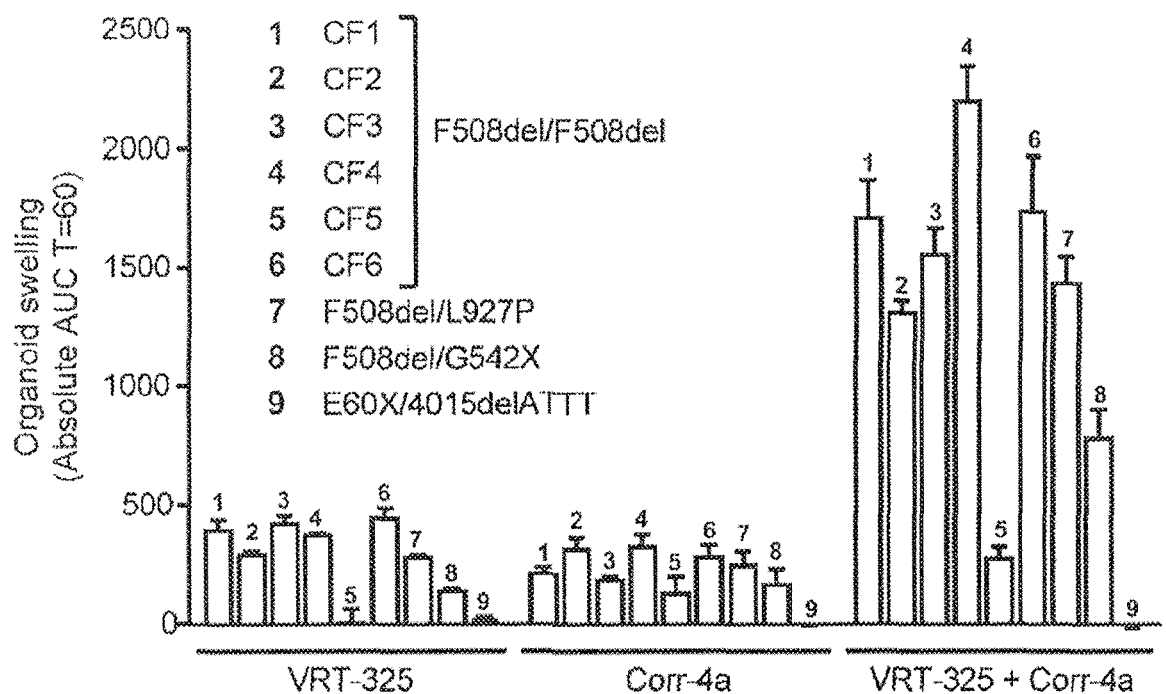
Figure 14B:
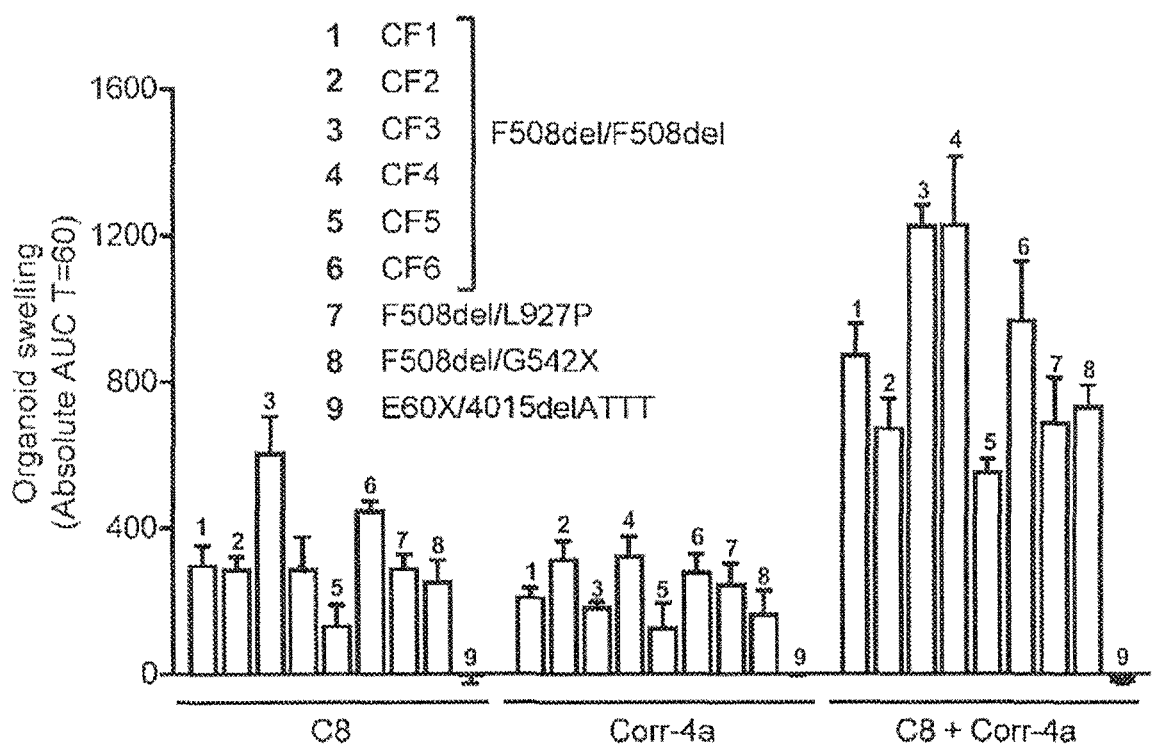

FIGS. 14A to 14D show differential FIS of CF organoids upon chemical CFTR restoration. FIGS. 14A to 14C show quantification of FIS in organoids derived from 9 individual CF patients pre-treated for 24 hours with VRT-325 (10 µM), Corr-4a (10 µM), or both correctors (FIG. 14A), with $C_8$ (10 µM), Corr-4a (10 µM), or both correctors (FIG. 14B) or stimulated with VX-809 (24 h pre-treatment, 3 µM), VX-770 (simultaneous with forskolin, 3 µM) or both compounds (FIG. 14C). The bars correspond to the bars depicted in FIG. 12E of the 'Severe CF' panel. Each bar represents FIS expressed as absolute area under the curve (AUC) calculated from time lapses as presented in FIGS. 13D to 13F (baseline=100/o, T=60 min) corrected for FIS of DMSO-treated organoids and averaged from at least three independent experiments performed with weekly intervals (mean±s.e.m.). FIG. 14D shows average FIS responses of compound-treated F508del/F508del organoids (n=6 from a-c) and DMSO-treated F508del/A455E organoids (n=2) relative to average FIS of DMSO-treated HC organoids (n=3) expressed in AUC calculated from time lapses as illustrated in FIGS. 13D to 13F (baseline=100%; T=60 min; mean±s.e.m.).

FIG. 15 shows light microscopy analysis of wild-type murine organoids stimulated with forskolin or DMSO. Representative examples for the indicated time points after start of stimulation are shown. The forskolin-induced swelling (FIS) of organoids was reversed upon removal of forskolin by washing. Scale bar 30 µm.

Figure 16A:
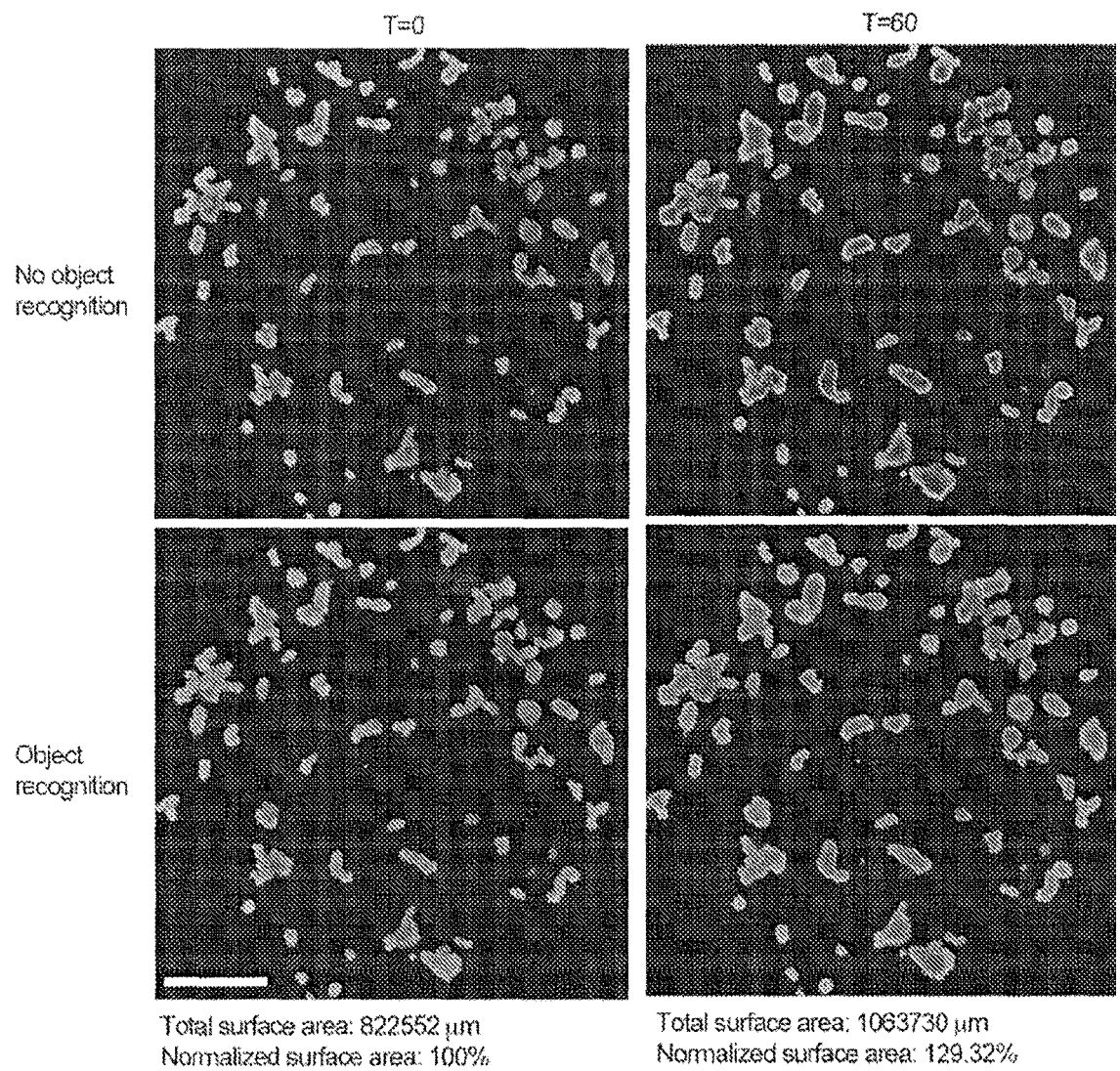
Figure 16C:
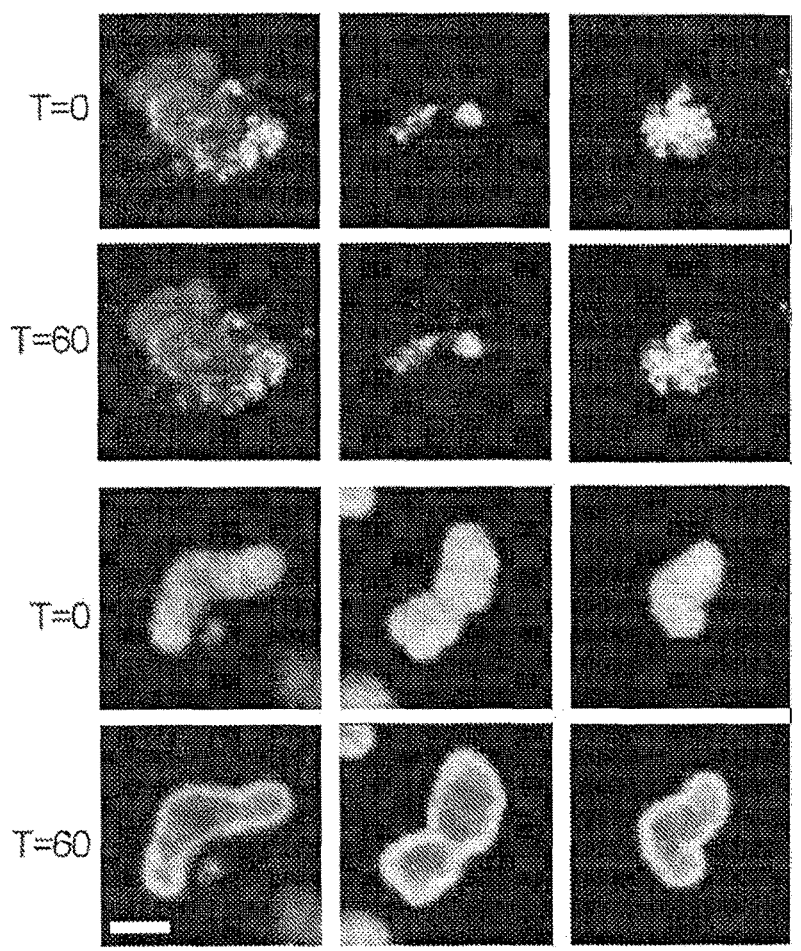
Figure 16D:
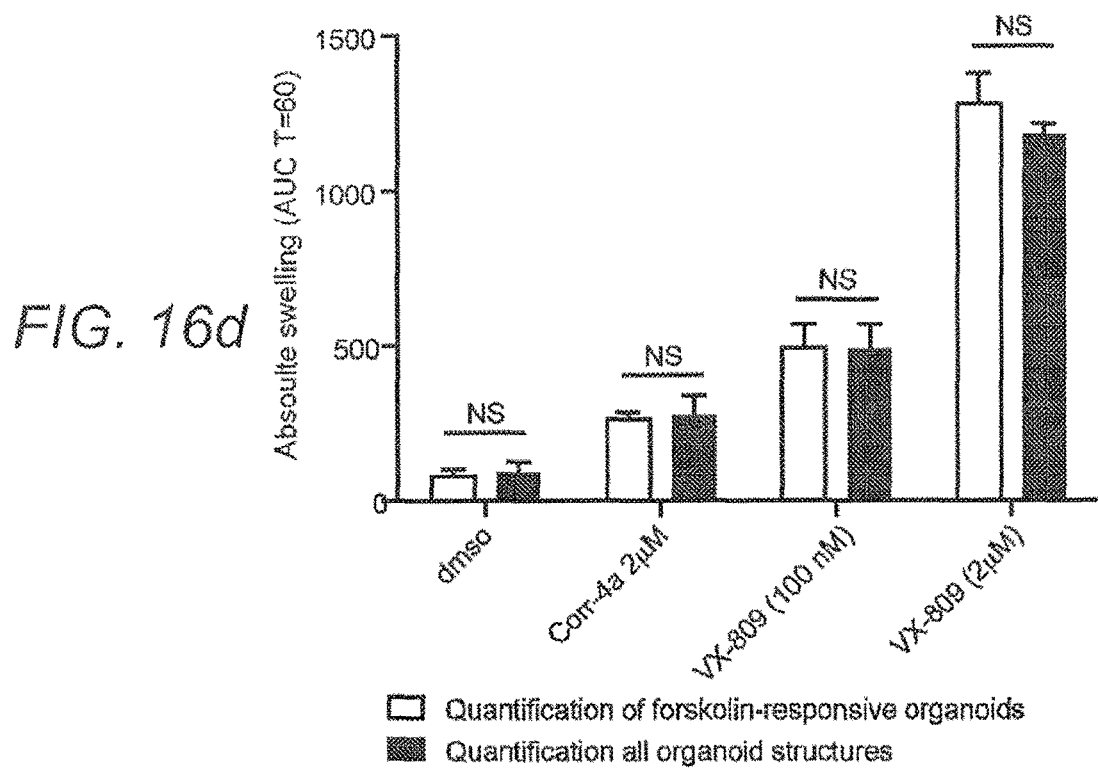

FIGS. 16A to 16D show organoid swelling in response to forskolin. FIG. 16A shows examples of quantification of total organoid surface area using Volocity imaging software. A representative confocal image is shown of calcein-green-labeled rectal F508del-CFTR organoids pre-treated for 24 h with VX-809 in a well of a 96-well plate at the indicated time points of forskolin treatment. Scale bar 520 µm. FIG. 16B shows percentages of forskolin responding and non-responding objects from different origin with or without drug treatment calculated from three independent experiments. FIG. 16C shows representative confocal images of irregularly shaped (non-responding) or normally shaped (responding) organoids at the indicated time points of forskolin simulation. FIG. 16D shows quantification of FIS expressed in absolute area under the curve (AUC) calculated from time lapses as illustrated in FIGS. 13D to 13F (baseline-100%, T=60 min) with or without pre-selection of responding structures. NS=not significant.

Figure 17A:
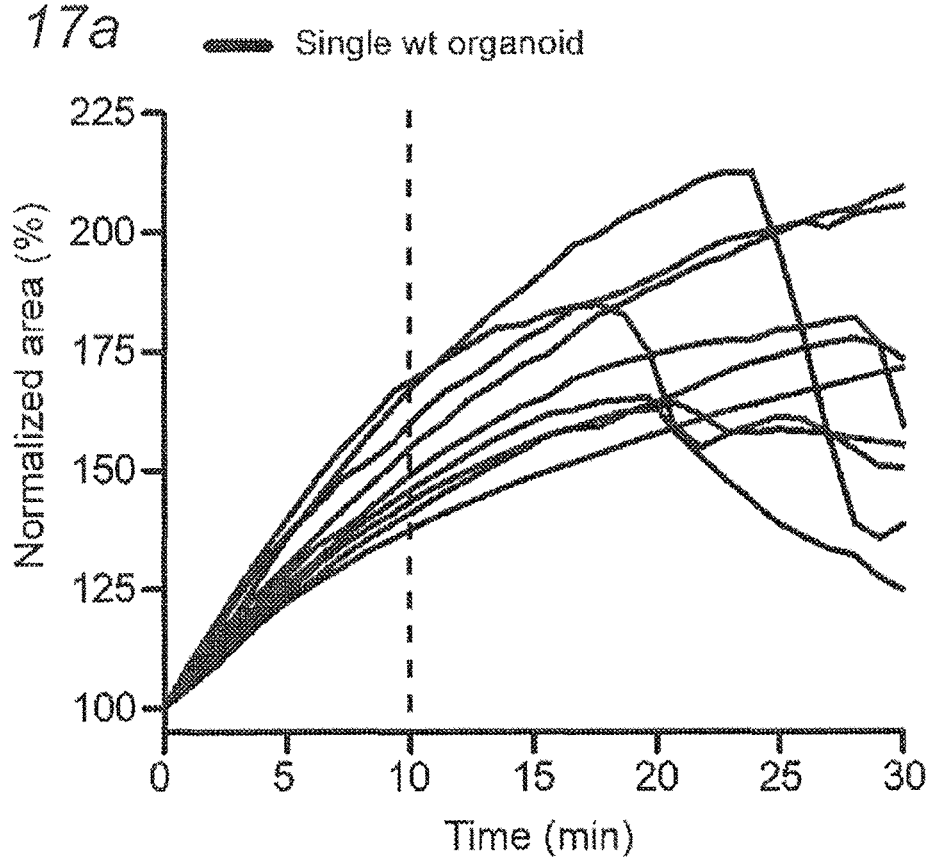
Figure 17B:
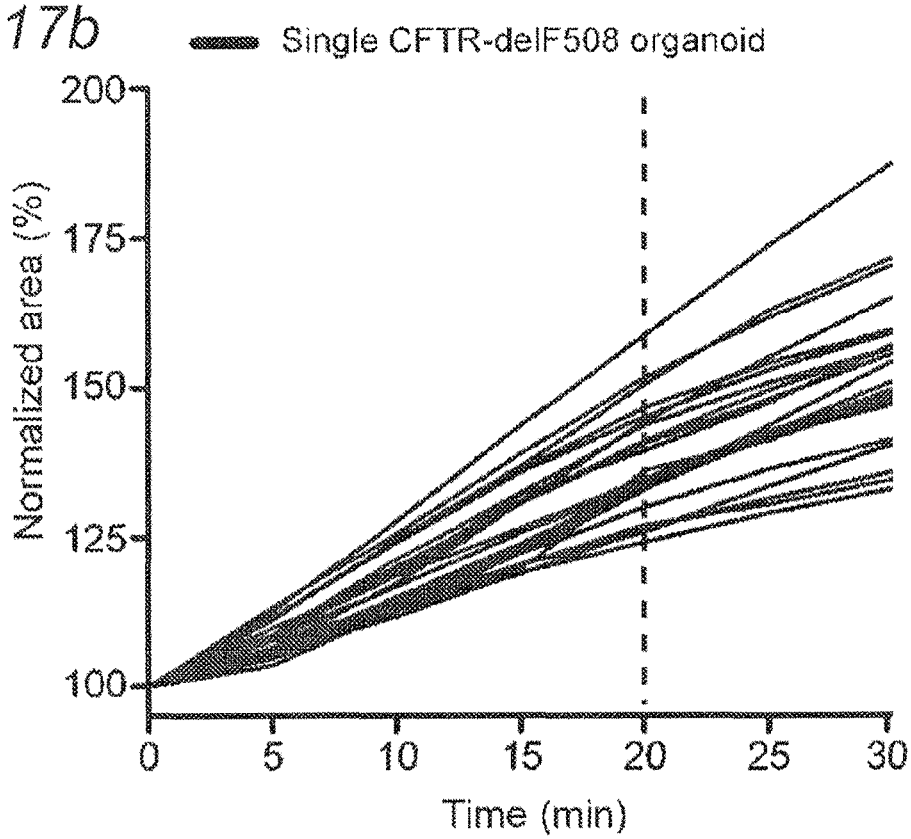
Figure 17C:
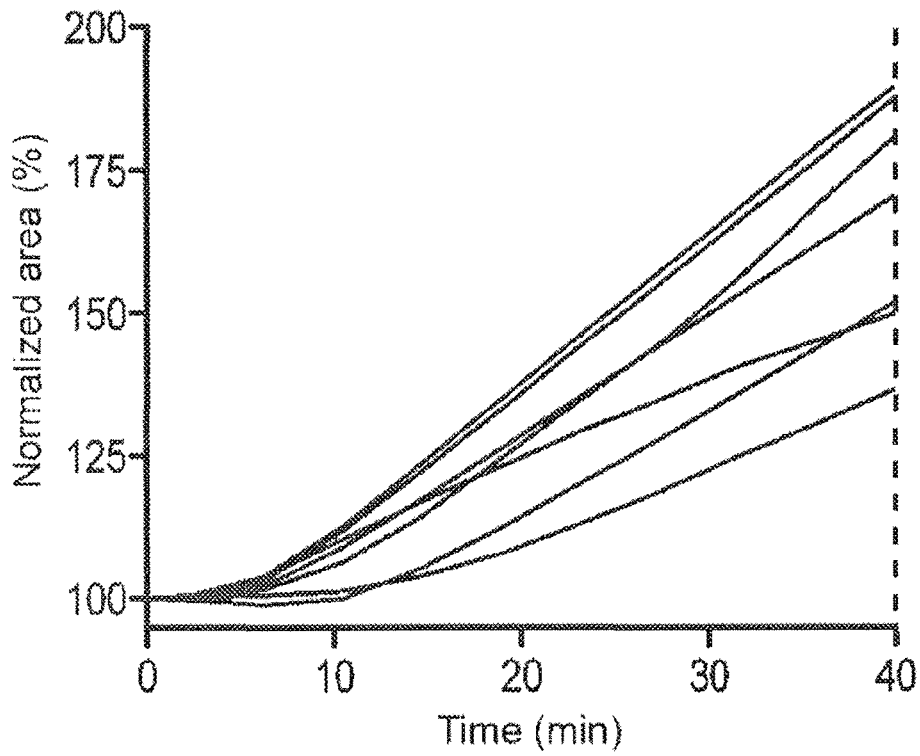

FIGS. 17A to 17C show time lapses of forskolin-induced swelling in murine and human organoids. Normalized surface area increase of individual forskolin-stimulated (FIG. 17A) wild-type, (FIG. 17B) F508del-CFTR (temperature-rescued) and (FIG. 17C) human small intestinal HC organoids. The averaged forskolin-induced swelling of different organoid types was analyzed for different time points to prevent measurement of collapsing organoids (dashed lines).

Figure 18:
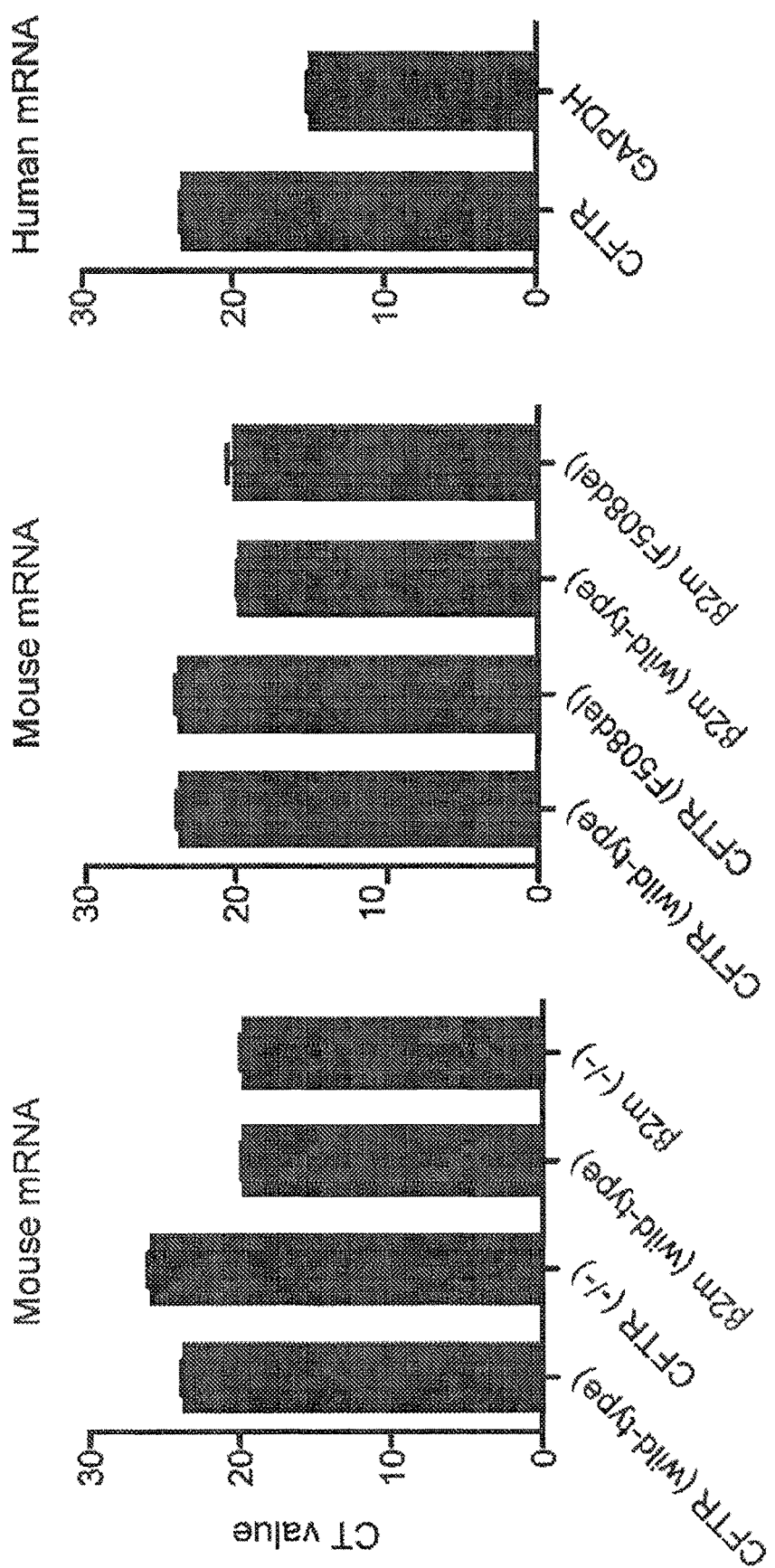

FIG. 18 shows CFTR mRNA expression in murine and human organoids. The bars show real-time PCR cycle threshold (CT) values representing mRNA levels of CFTR, 82m or GAPDH isolated from small intestinal F508del-CFTR (left graph) or $Cftr^{1-}$ (middle graph) organoids and their corresponding wild-types, or human HC small intestinal organoids.

Figure 19A:
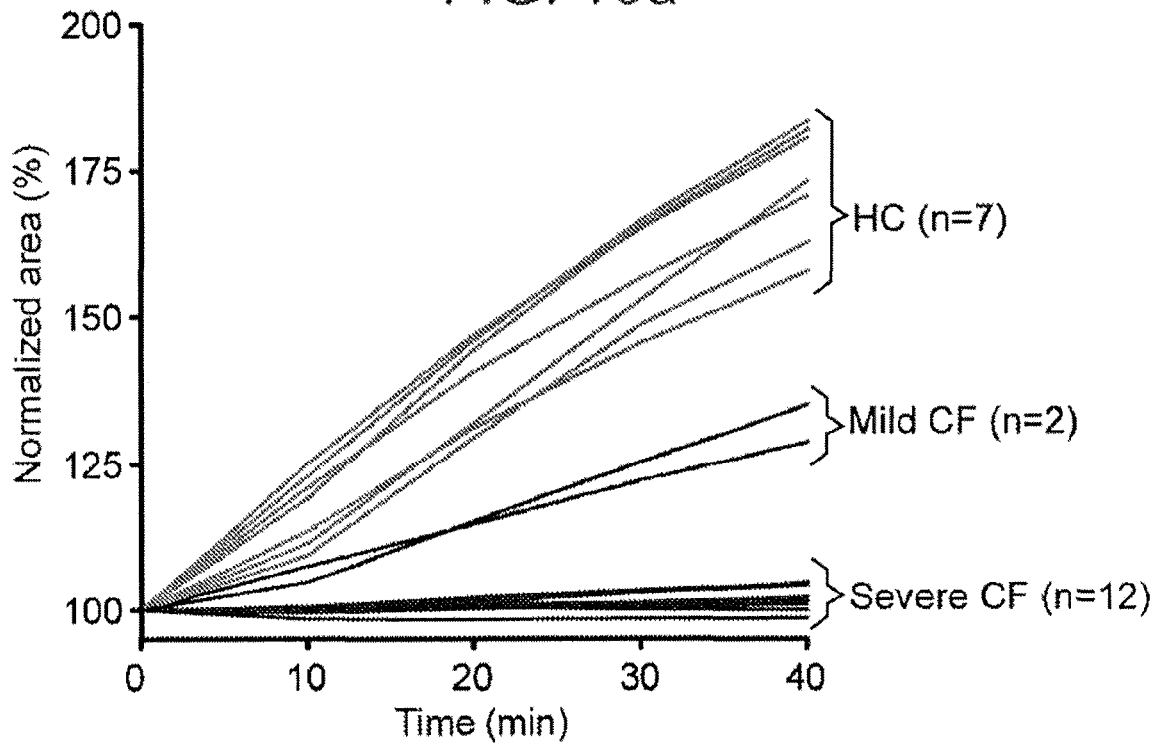

FIGS. 19A to 19C show forskolin-induced swelling in HC and CF organoids. FIG. 19A shows forskolin-stimulated swelling of intestinal organoids derived from 7 individual healthy controls (2× duodenum, 1× ileum, 1× colon, 3× rectum), 2 patients with a mild CF genotype (F508del/A455E; rectum) and 12 patients with a severe CF genotype (duodenum: F508del/F508del and F508del/Exon17del; Ileum: F508del/F508del; rectum: 1× E60X/4015delATTT; 1× F508del/G542X; 1× F508del/L927P; 6× F508del/F508del). FIGS. 19B and 19C show forskolin-induced swelling expressed in AUC calculated from time lapses of organoids area increase (baseline=100%, T=60) of rectal organoids with a mild or severe CF genotype with or without CFTR inhibition. (Severe CF: F508del/G542X, F508del/L927P and F508del/F508del (6×); Mild CF: F508del/A455E n=2); mean±s.e.m.).

Figure 20A:
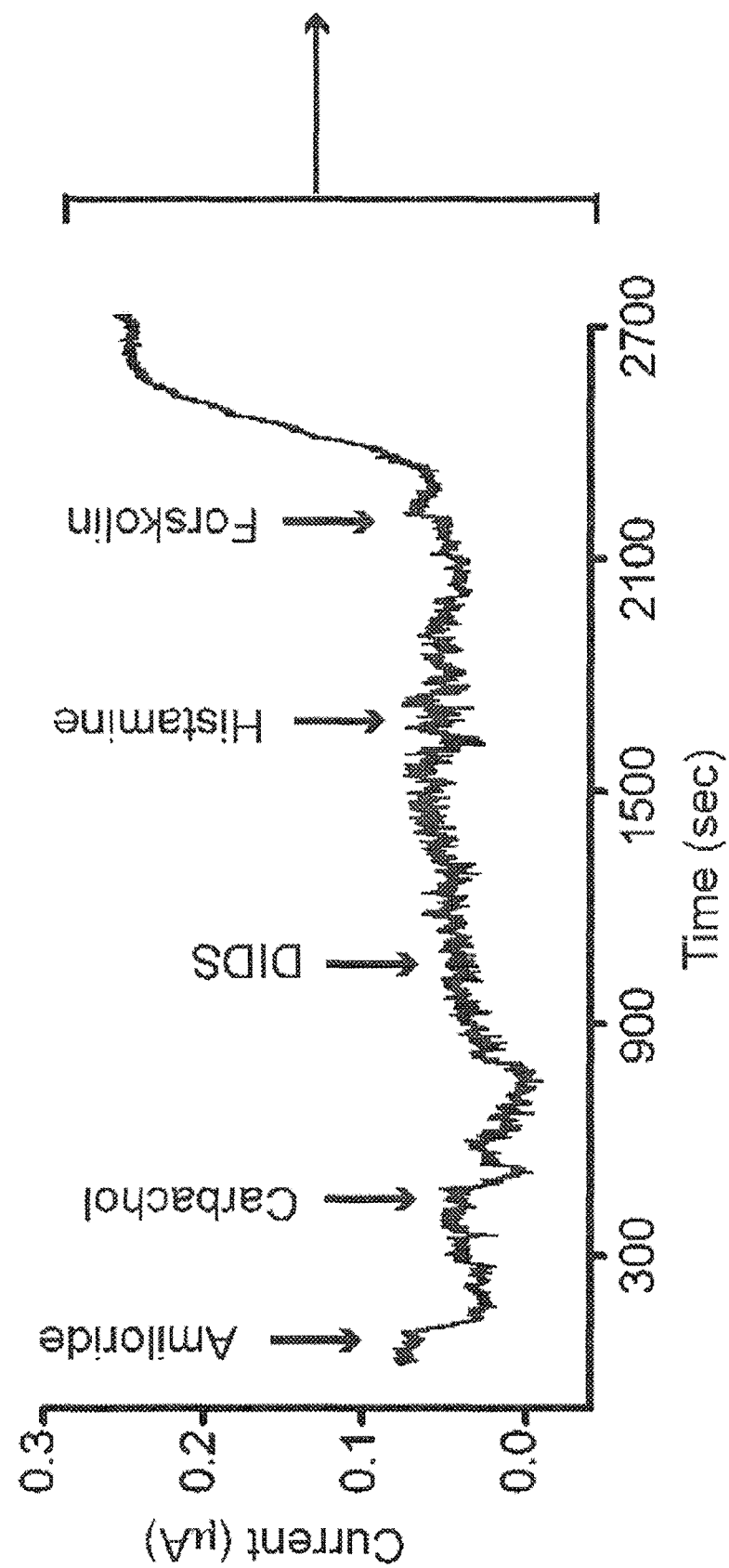
Figures 20B, 20C:
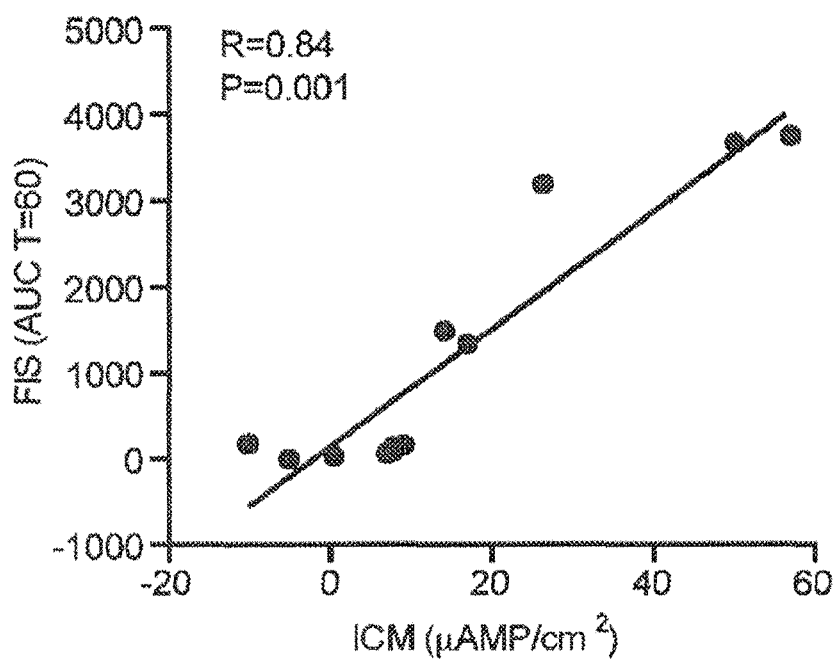

FIGS. 20A to 20C show paired measurement of CFTR function by FIS or ICM. FIG. 20A shows representative intestinal current measurement (ICM) tracing of F508del-CFTR rectal biopsies.

FIG. 20B shows overview of paired FIS and ICM responses of different individuals. FIS is expressed as absolute area under the curve (AUC) calculated from time lapses as illustrated in FIGS. 13D to 13F (baseline-100%, T=60 min) and is averaged from at least three independent experiments performed with weekly interval. The ICM values represent average forskolin-induced current responses from 4 rectal biopsies of the same individual. FIG. 20C shows a correlation plot of FIS and ICM values from FIG. 20B. R (=correlation coefficient) and p-value were calculated by SPSS using a Spearman's rank correlation test.

Figure 21A:
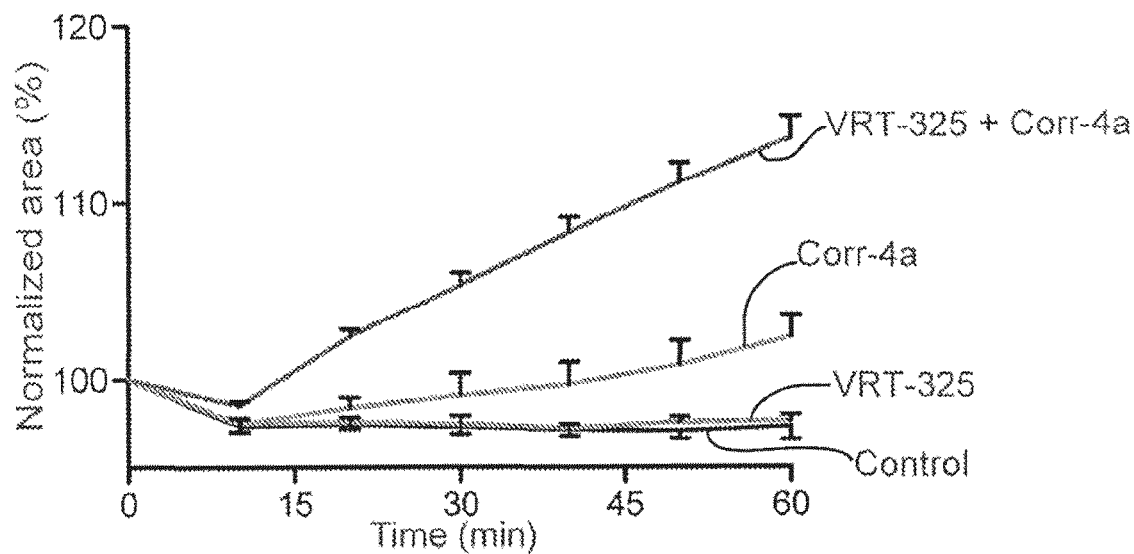
Figure 21B:
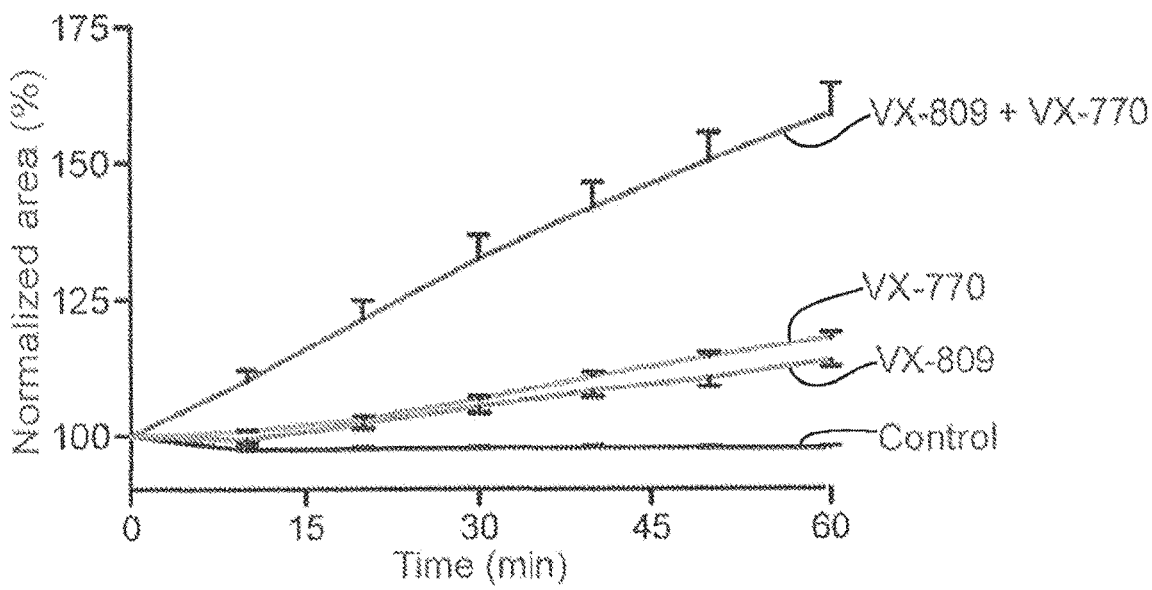
Figure 21C:
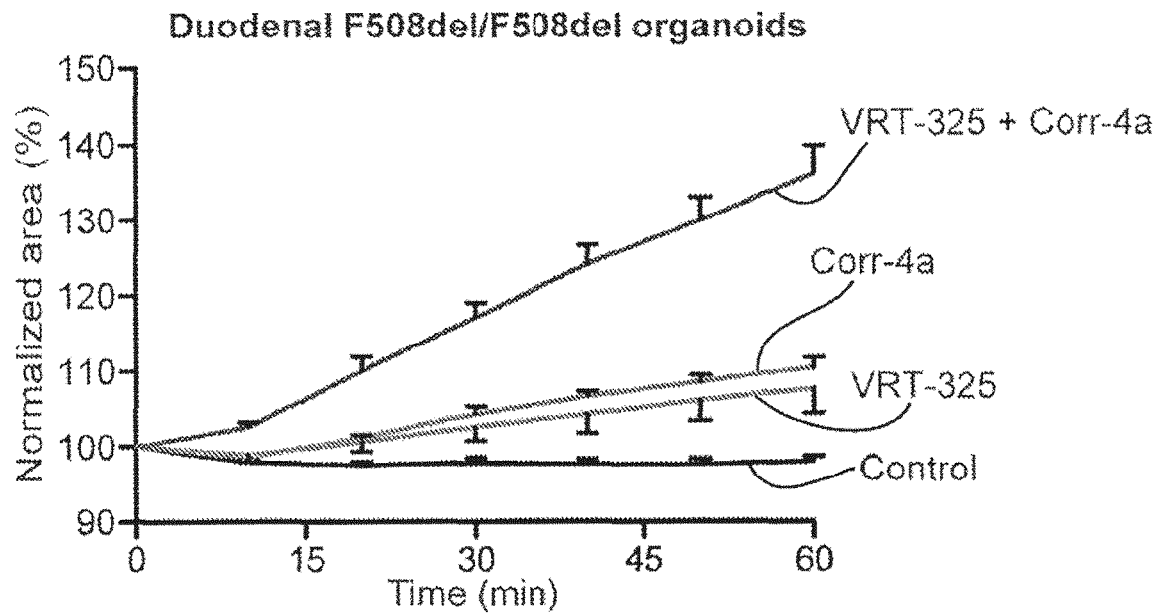
Figure 21D:
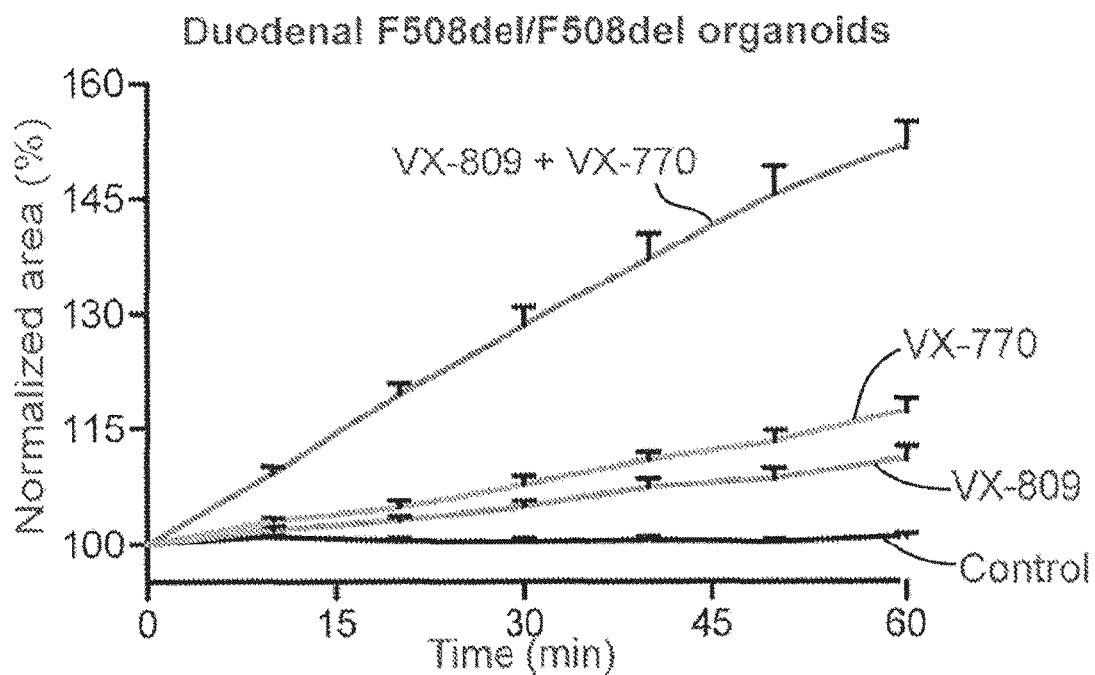
Figure 21E:
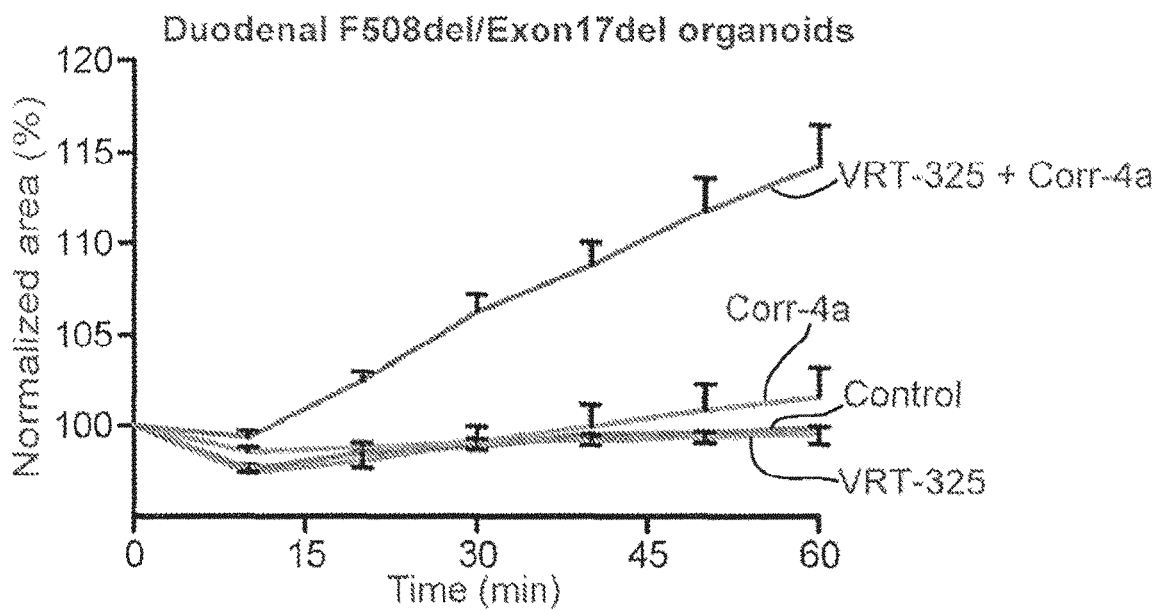
Figure 21F:
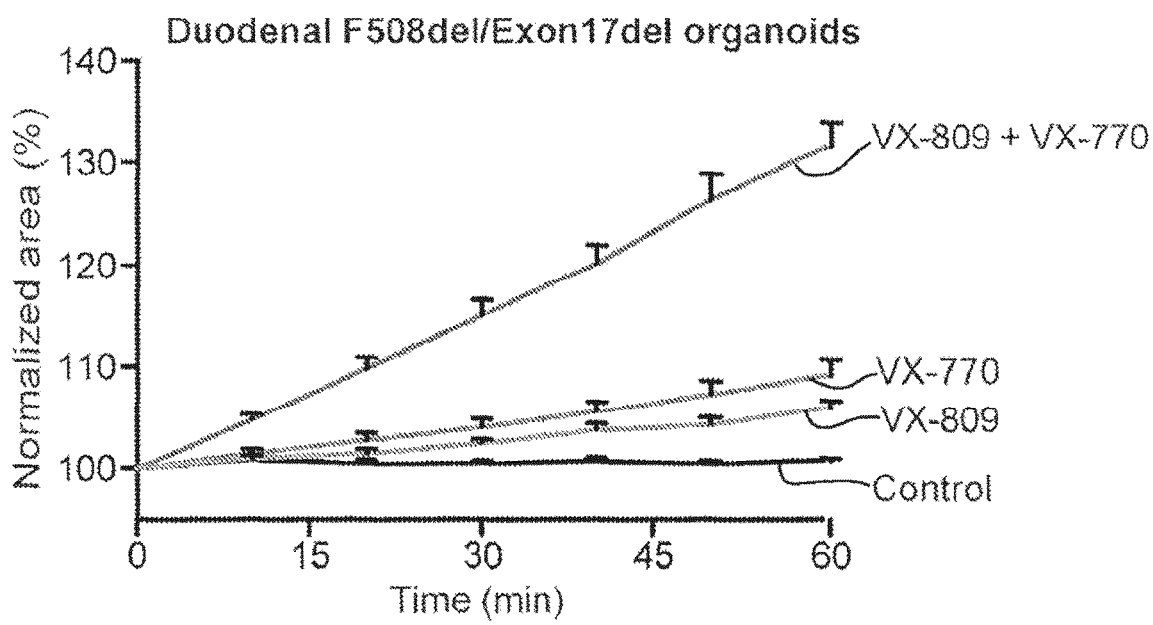

FIGS. 21A to 21F show chemical CFTR correction of non-rectal intestinal CF organoids. FIGS. 21A and 21B show time lapses of normalized forskolin-induced swelling of small intestinal organoids pre-treated for 24 hours with DMSO, VRT-325, Corr-4a, or both correctors (FIG. 21A) or stimulated with VX-809 (24 h pre-treatment), VX-770 (simultaneous with forskolin) or their combined treatment (FIG. 21B) (mean±s.e.m.).

Figure 22A:
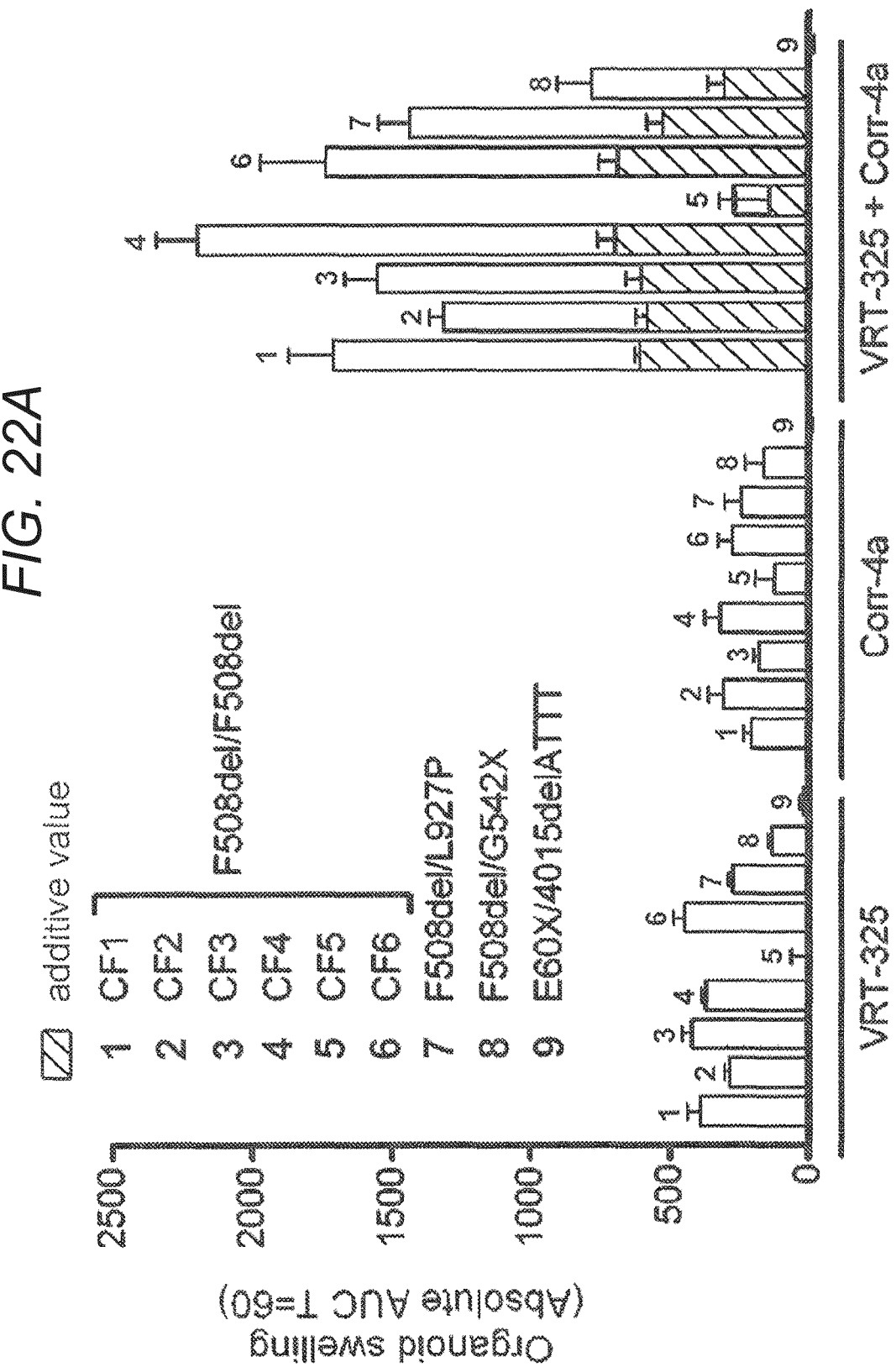
Figure 22C:
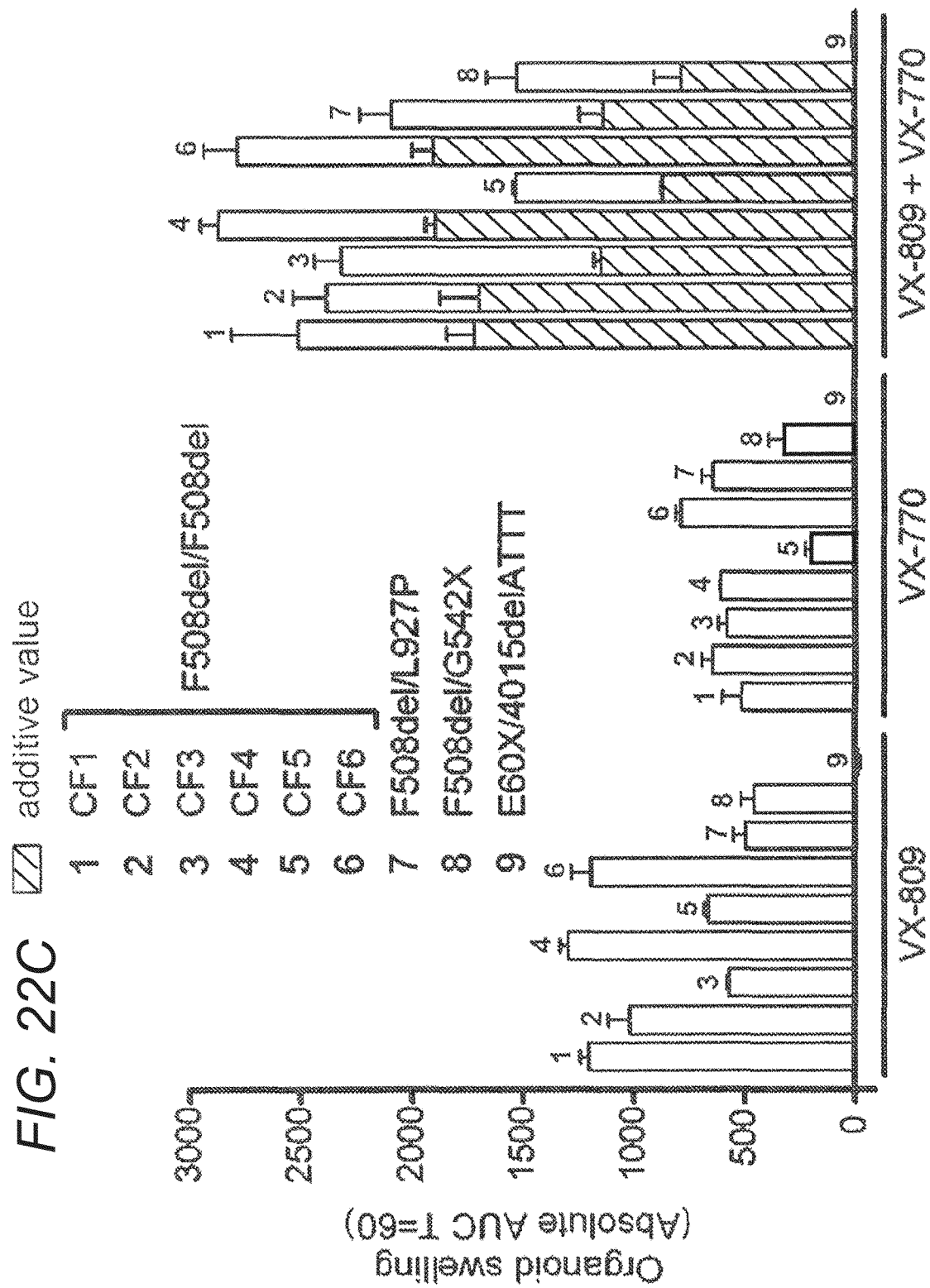

FIGS. 22A to 22C show a comparison of measured responses (total bars) and additive (internal bars) responses in rectal organoids upon single or combined drug treatment as indicated in FIG. 14.

Figure 23:
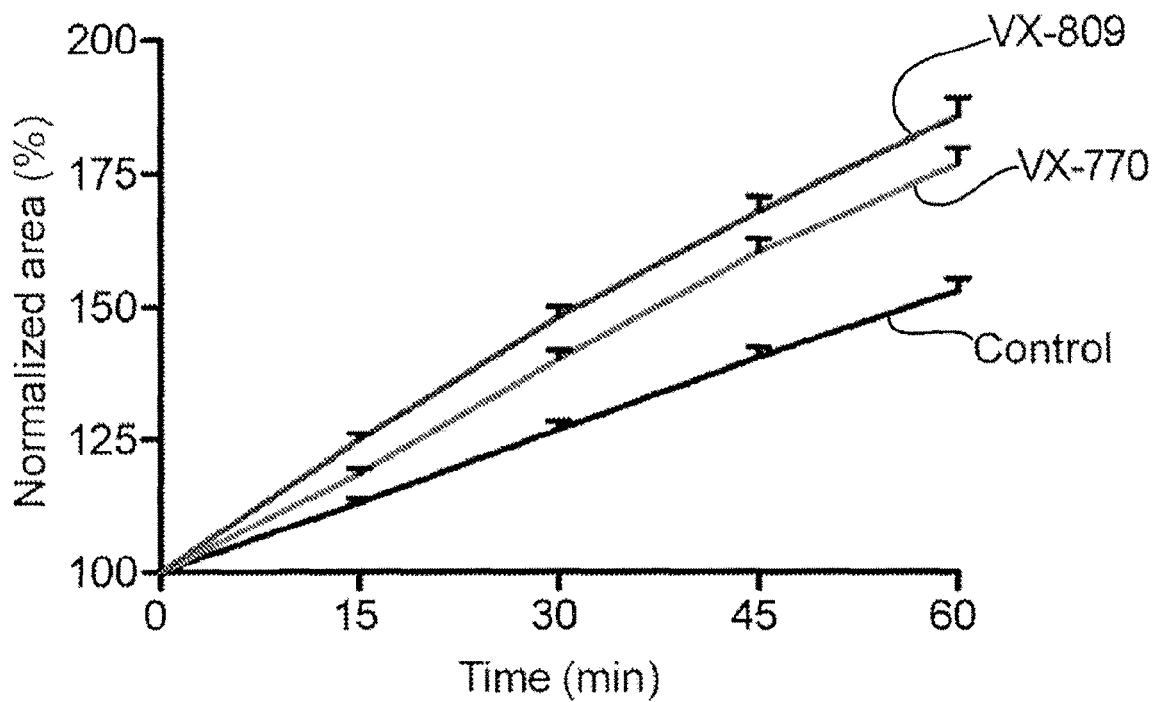

FIG. 23 shows the chemical correction of rectal F508del/A455E organoids. Normalized forskolin-induced swelling of rectal F508del/A455E organoids stimulated with VX-809 (24 h pre-treatment) or VX-770 (simultaneous with forskolin) (mean±s.e.m.).

Figure 24:
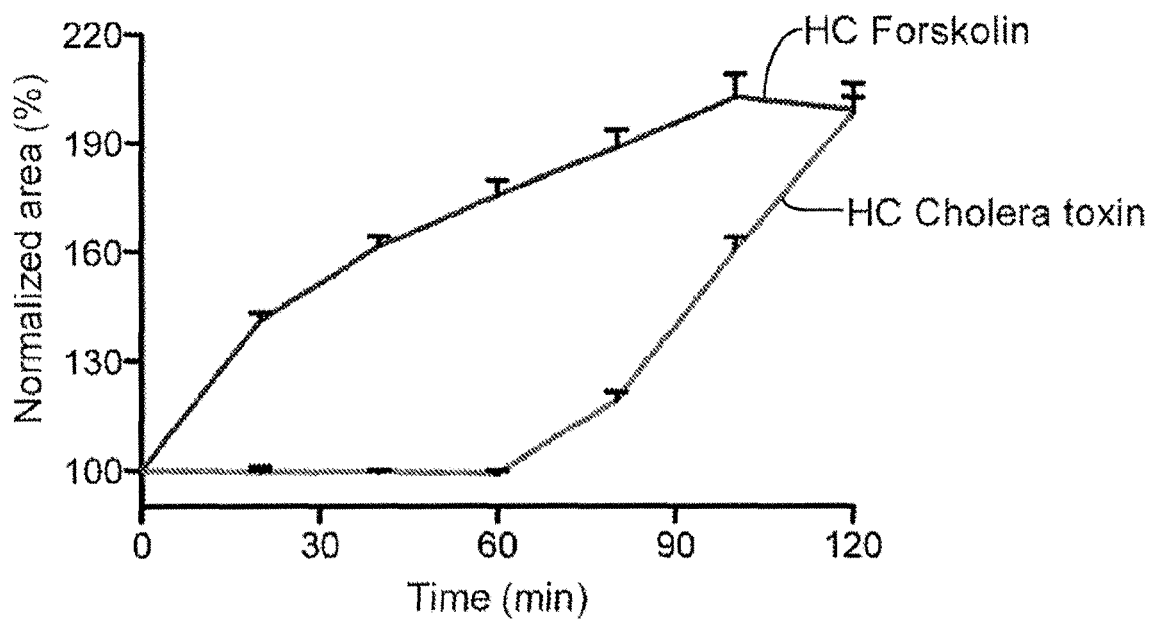

FIG. 24 shows cholera toxin-induced organoid swelling in human rectal organoids is CFTR dependent. Forskolin and cholera toxin induce swelling of HC-derived organoids. The cholera toxin response is delayed compared to forskolin (mean±s.e.m.). Results are representative for three different experiments.

Figure 25A:
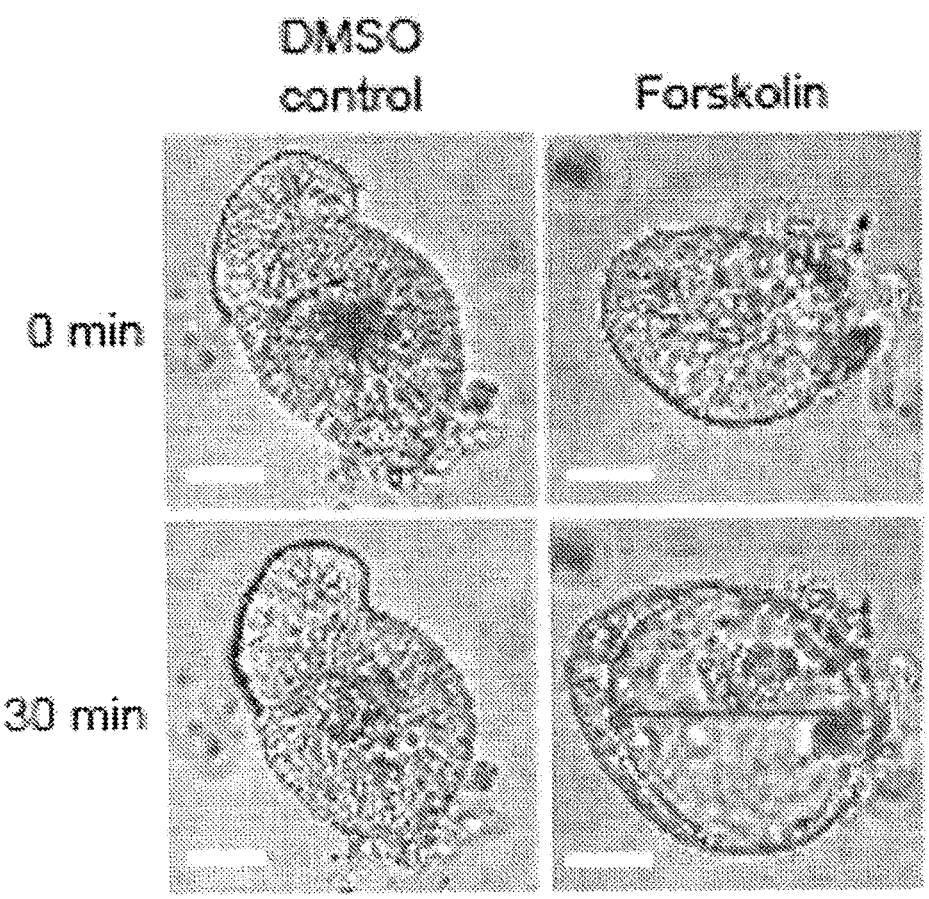
Figure 25B:
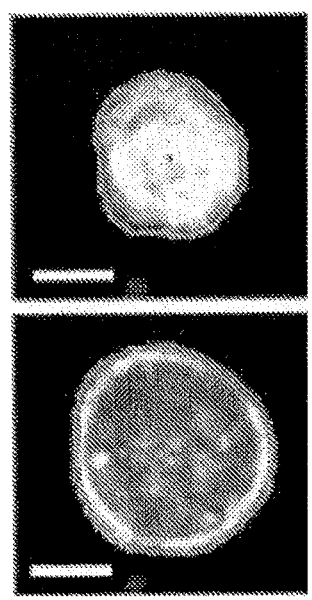
Figure 25C:
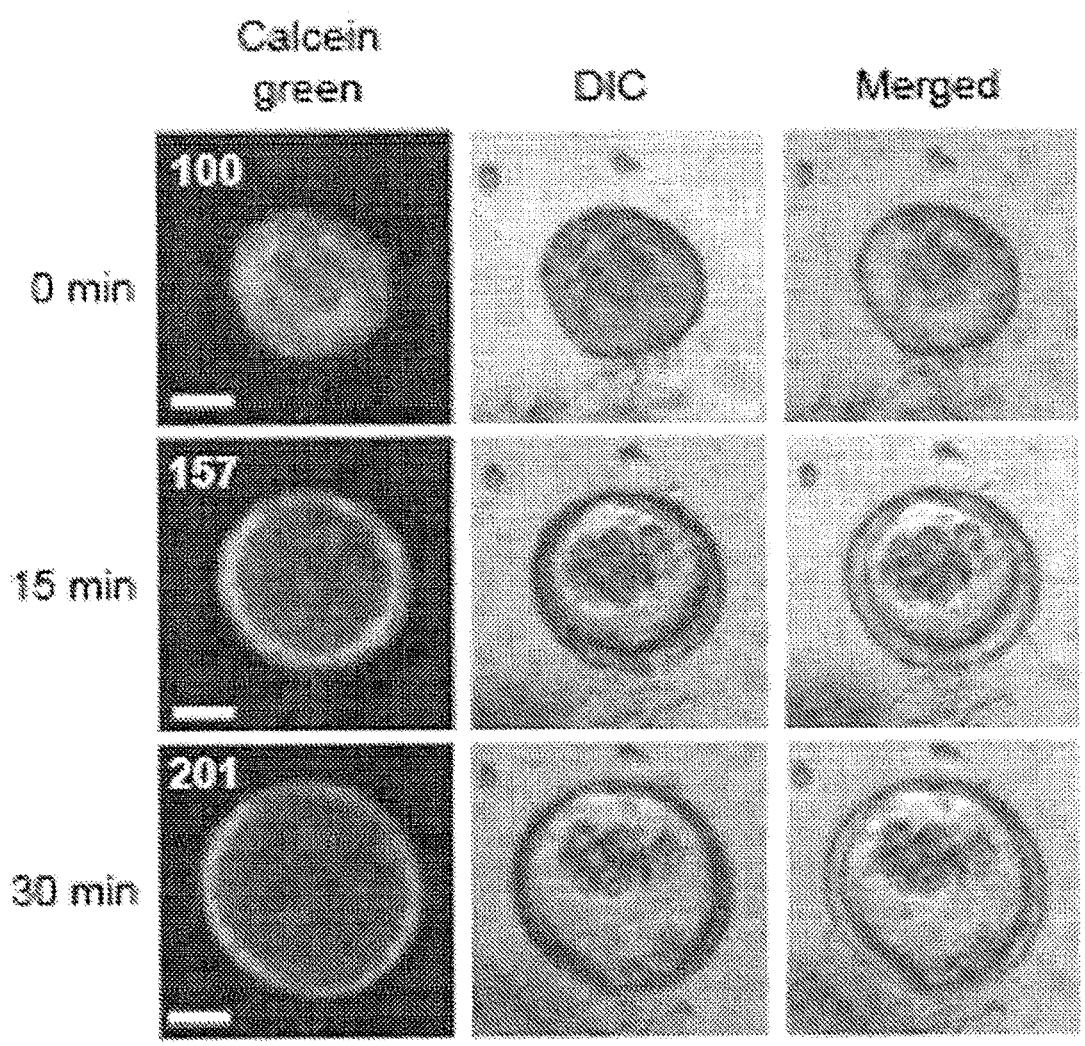
Figure 25D:
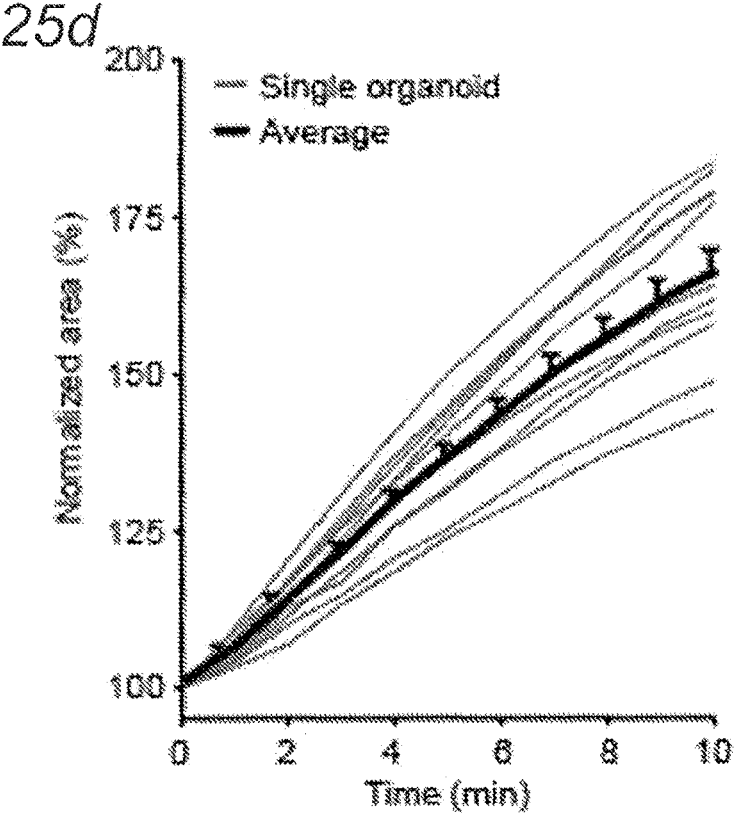
Figure 25E:
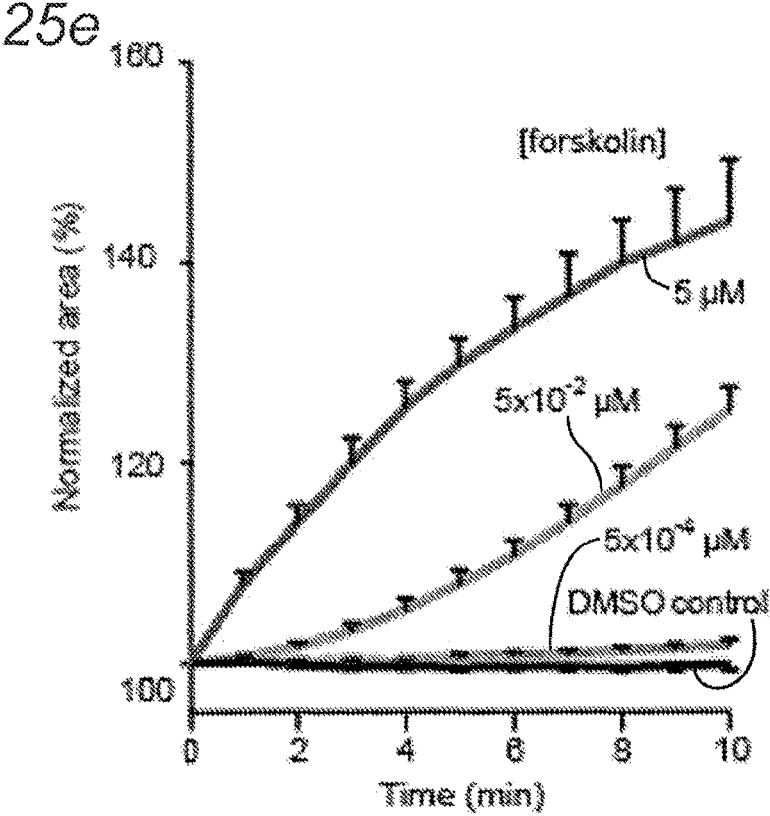

FIGS. 25A to 25E show quantification of forskolin-induced murine organoid swelling. FIG. 25A shows light microscopy analysis of organoids stimulated with forskolin or DMSO. Representative examples for the indicated timepoints after start of stimulation are shown. The red line indicates the internal organoid lumen. FIG. 25B shows a fluorescence confocal image of a calcein-green-labeled organoid with object recognition (green line) by image analysis software. FIG. 25C shows a representative example of a forskolin-stimulated calcein-green-labeled organoid. Differential interference contrast (DIC) and fluorescence was imaged using live cell confocal microscopy. Surface area relative to t=0 is indicated in the top-left corner. FIG. 25D shows normalized surface area increase of 11 individual organoids in a single well. The average is indicated in black (mean±s.e.m.). FIG. 25E shows dose-dependent increase of surface area by forskolin (5 µM (n=4 number of organoids analyzed), $5\times10^{-2}$ µM (n=11), $5\times10^{4}$ µM (n=10), DMSO n=9)). Scale bars in FIGS. 25A to 25C are 30 µm. All data is representative of at least three independent experiments.

Figure 26A:
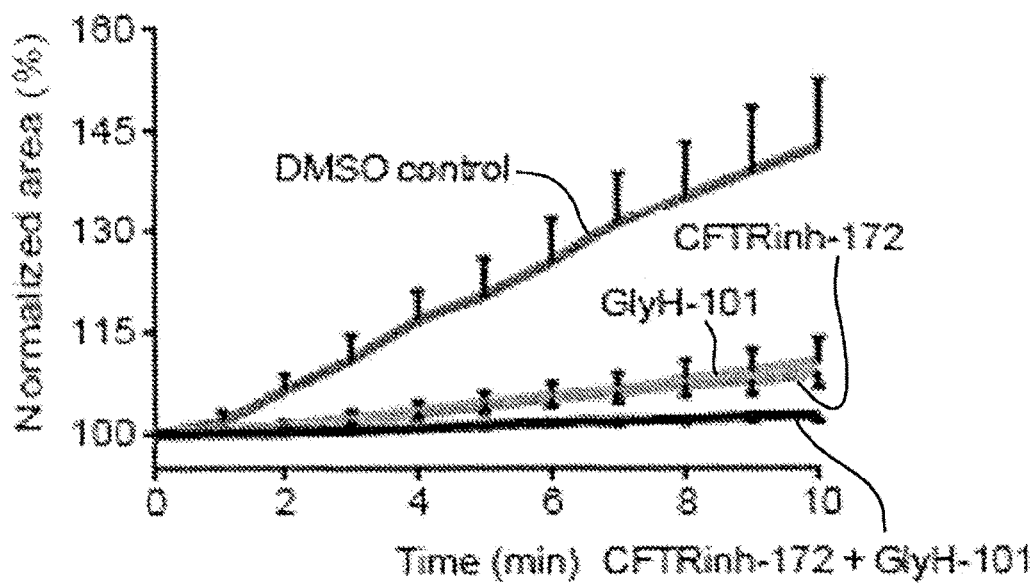
Figure 26B:
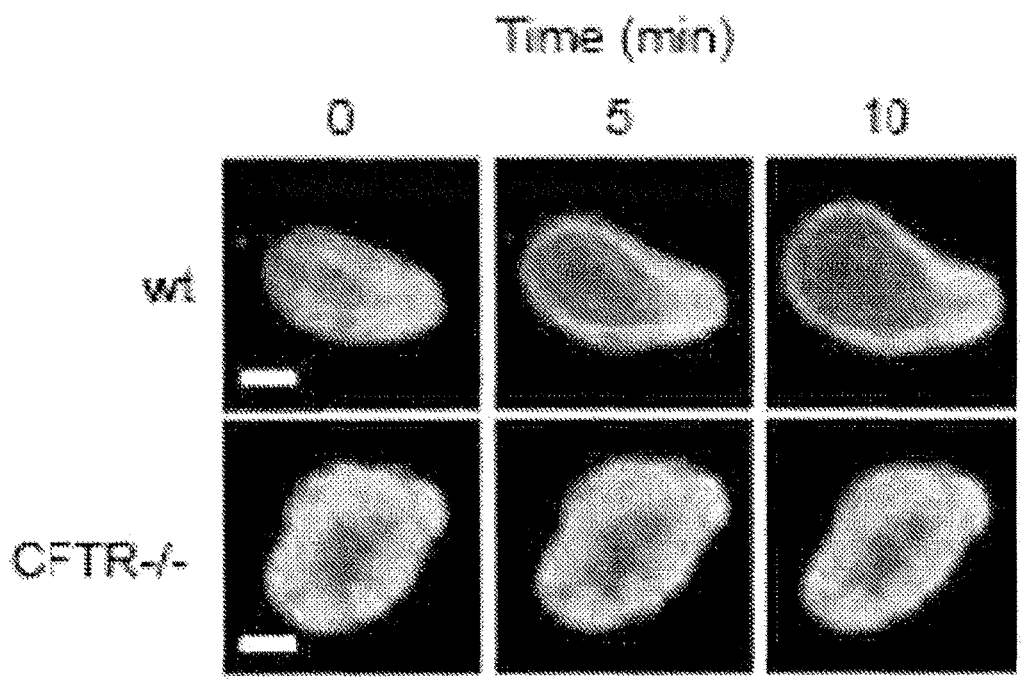
Figure 26C:
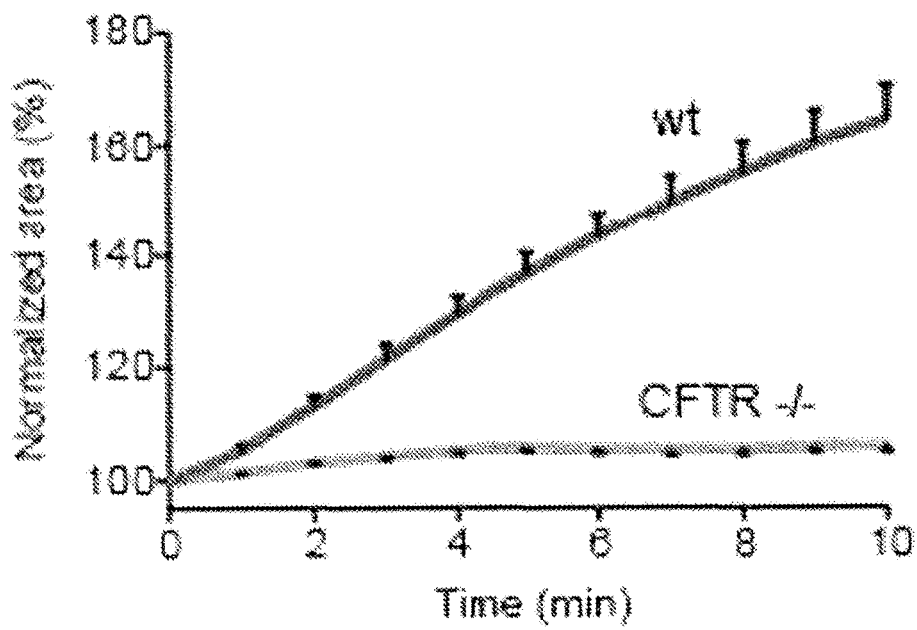
Figure 26D:
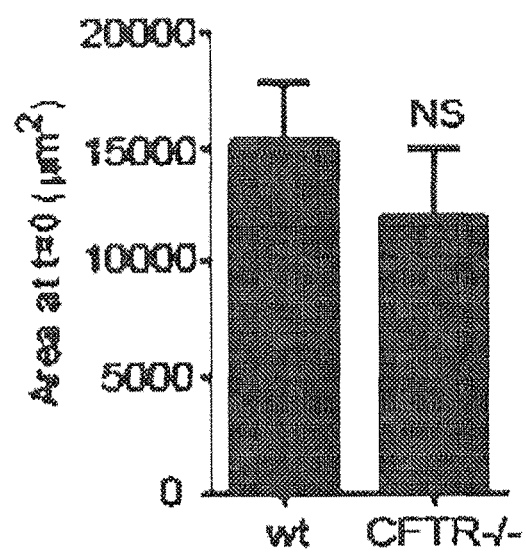
Figure 26E:
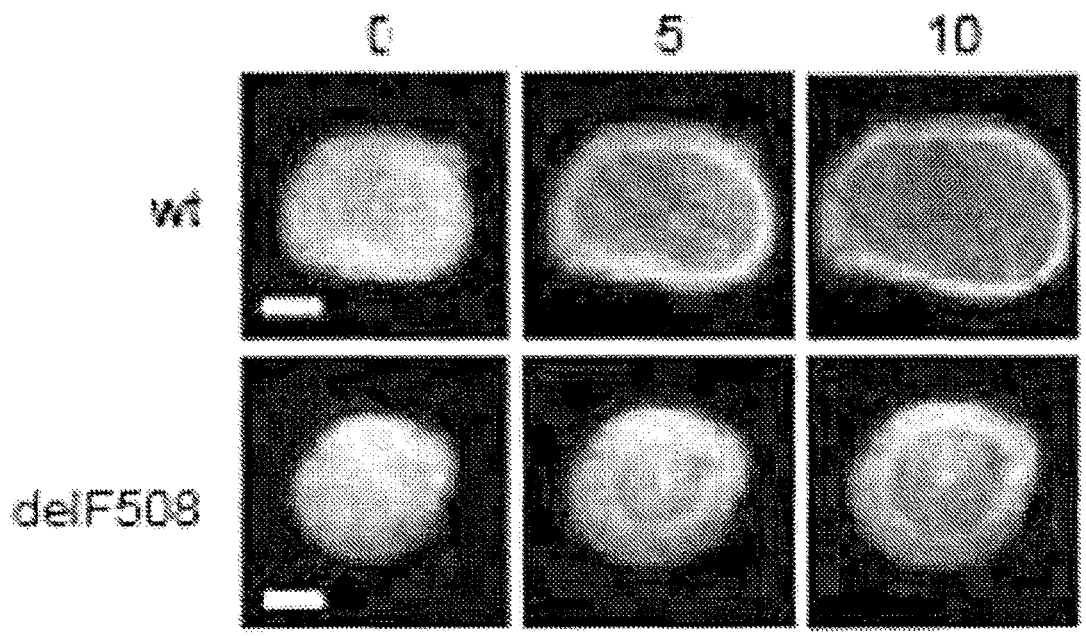
Figure 26F:
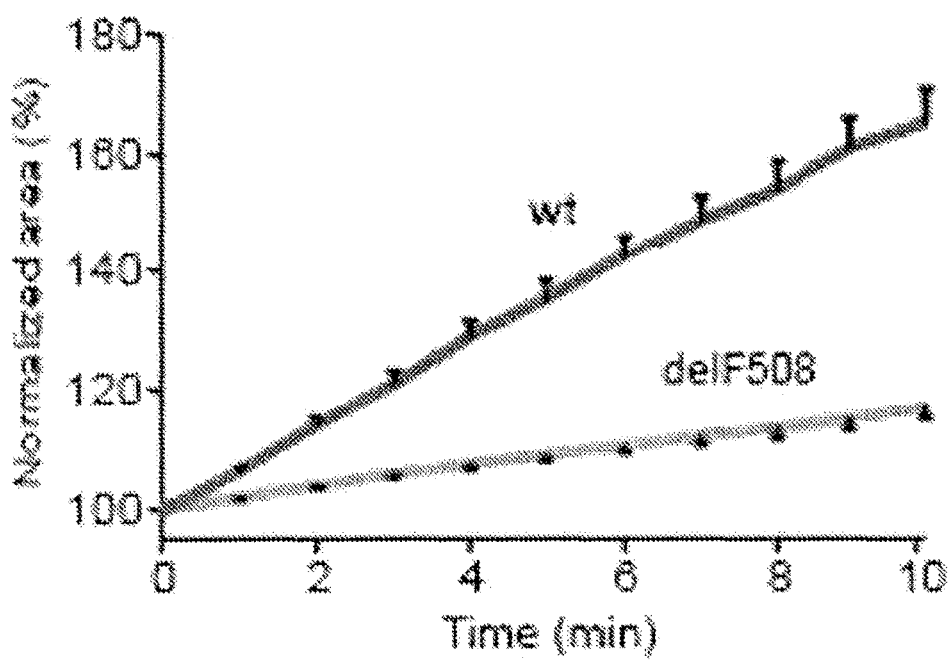
Figure 26G:
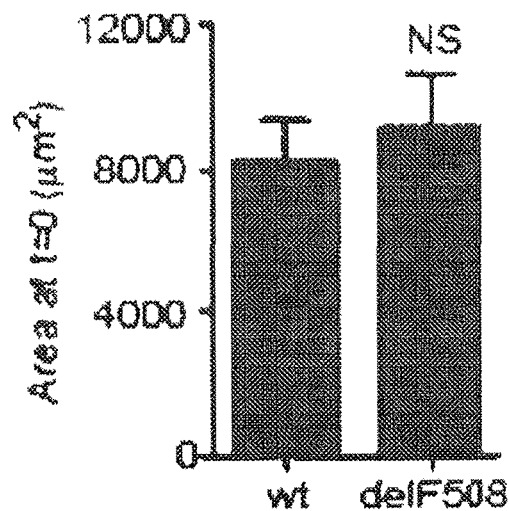
Figure 26H:
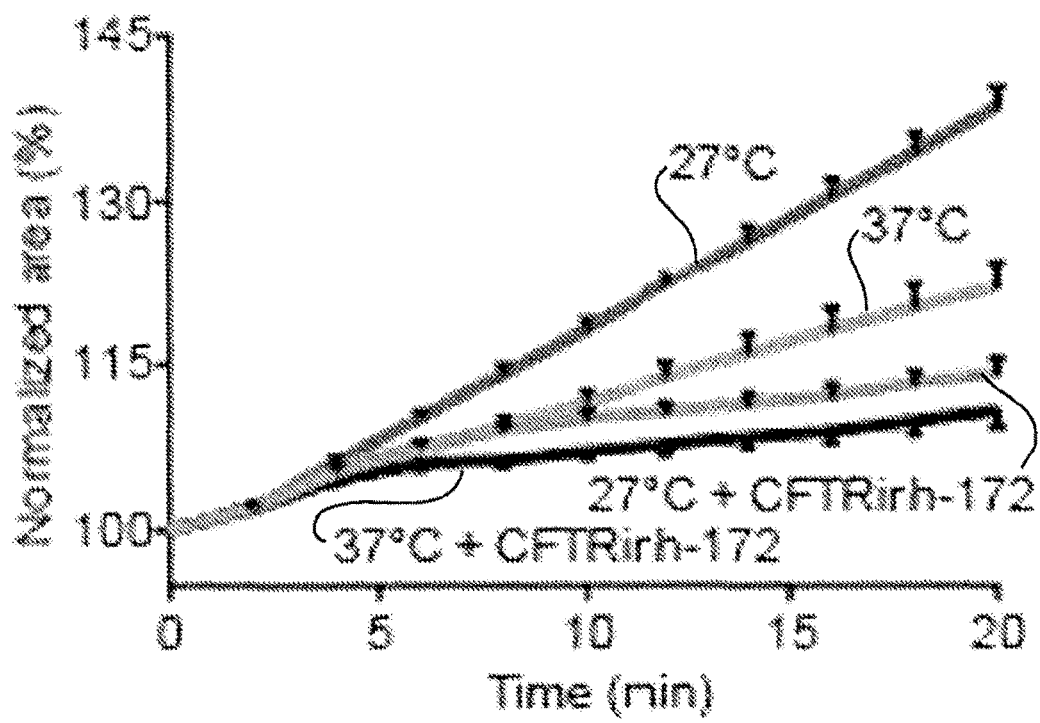

FIGS. 26A to 26H show forskolin-induced swelling of murine organoids is CFTR dependent. FIG. 26A shows normalized swelling curves of forskolin-stimulated calcein-green-labeled organoids pre-incubated with DMSO (n=8), CFTR-inh172 (n=7), GIyH-101 (n=9) or both CFTR-inh172 and GIyH-101 (n=11) (mean±s.e.m.). FIG. 26B shows representative confocal microscopy images of calcein-green labeled wild type or CFTR-deficient organoids in response to forskolin. Scale bars 50 µm. FIG. 26C shows quantification of forskolin-induced swelling in wild type (n=6) or CFTR-deficient (n=11) organoids (mean±s.e.m.) FIG. 26D shows absolute size of wild type or CFTR-deficient organoids quantified in FIG. 26C at t=0 (mean t s.e.m.). FIGS. 26E to 26G are similar to FIGS. 26B to 26D but for wild type (n=8) and CFTR-delF508 (n=12) organoids. Scale bars 30 µm. FIG. 26H shows forskolin-stimulated swelling of calcein-green labeled CFTR-delF508 organoids cultured at 37° C. with (n=20) or without (n=15) CFTR inhibition or cultured at 27° C. for 24 hours with (n=31) or without (n=27) CFTR inhibition (mean±s.e.m.). All data is representative of at least three independent experiments.

Figure 27A:
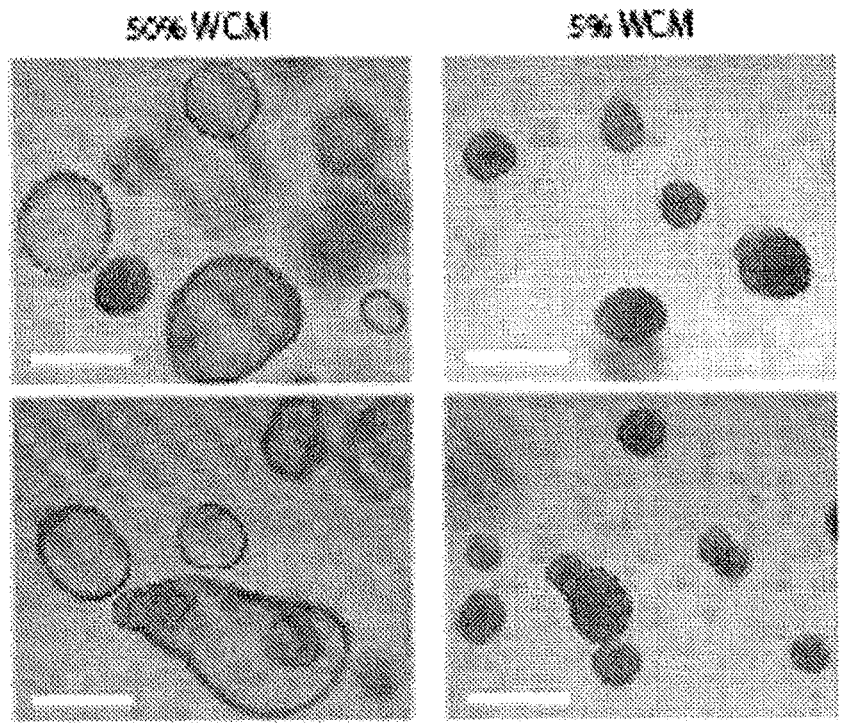

FIGS. 27A to 27D show forskolin-induced swelling of human organoids is CFTR-dependent. FIG. 27A shows light microscopy images human organoids cultured at normal (50%, left panel) or reduced (5%, right panel) Wnt3a conditioned medium (WCM) concentrations. Scale bars 400 µm.

Figure 27B:
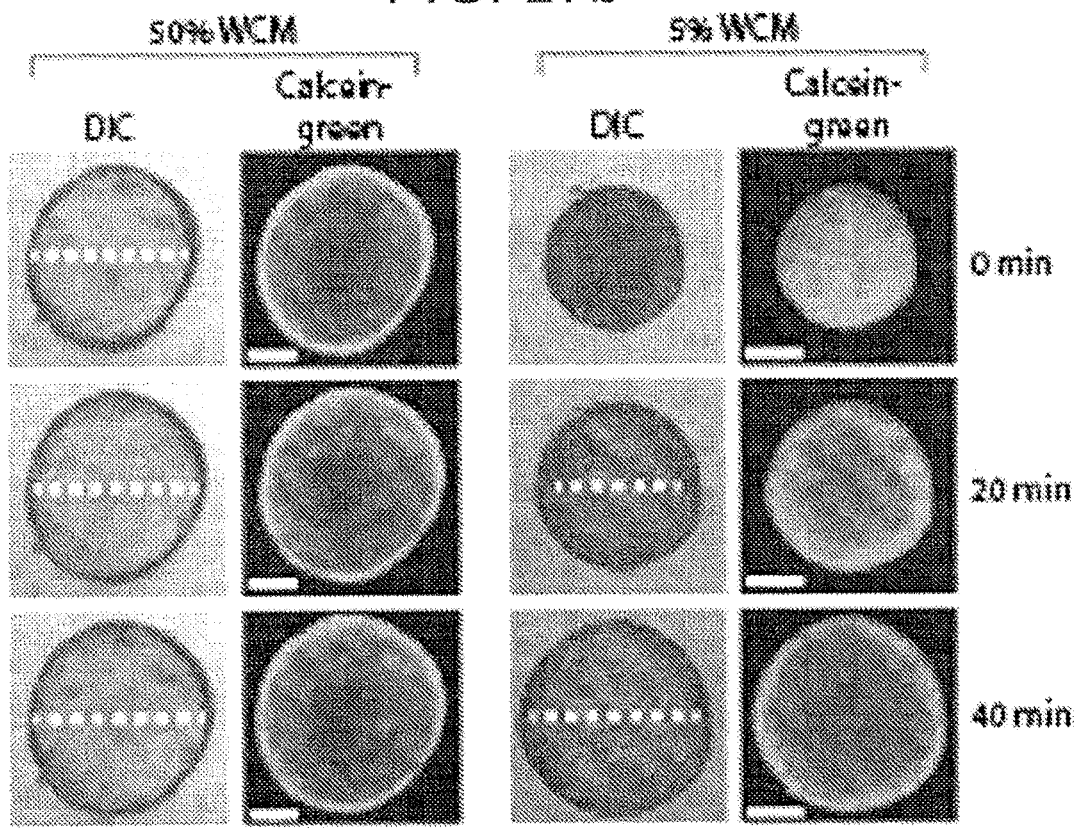
Figure 27C:
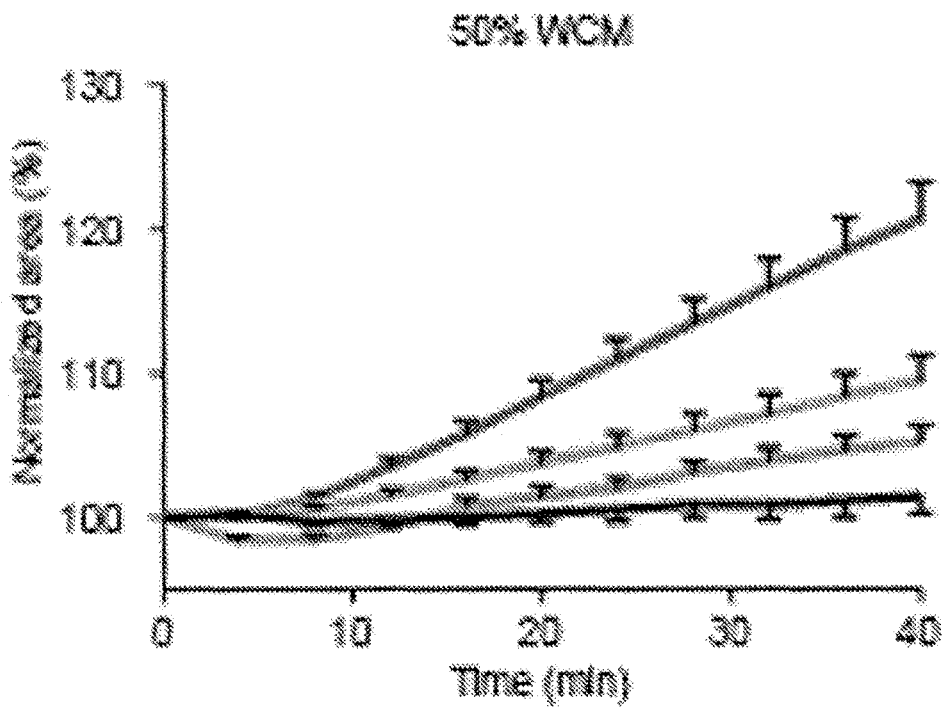
Figure 27D:
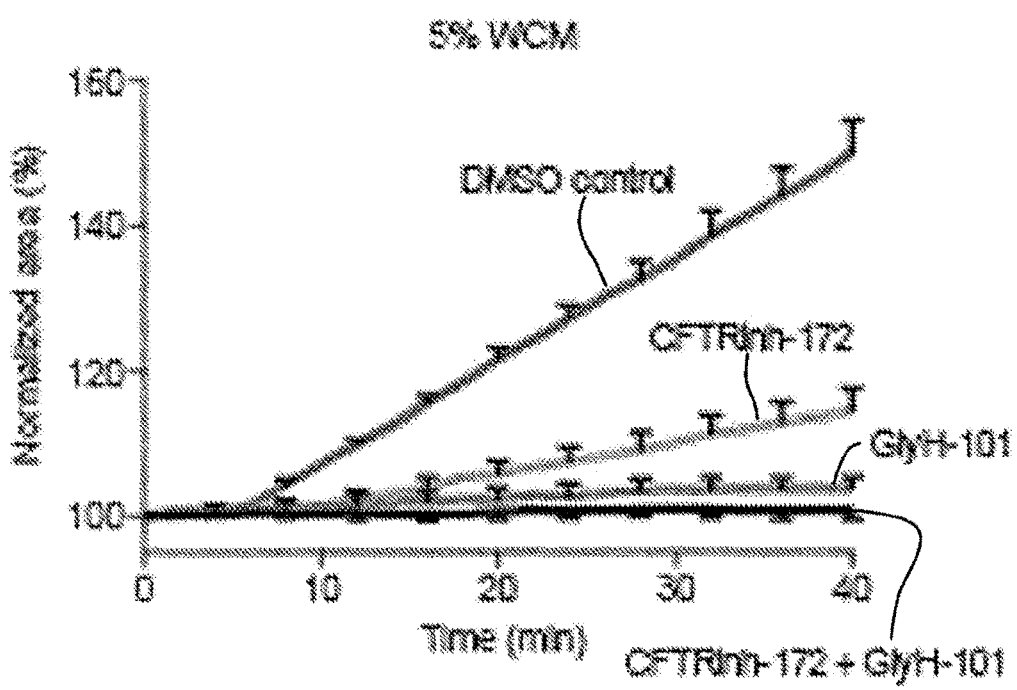

FIG. 27B shows representative examples of forskolin-induced swelling at normal or reduced Wnt3a conditions. Surface areas relative to t=0 are indicated. Scale bars 50 µm. The dashed line depicts the internal lumen (FIGS. 27C and 27D). Quantification of forskolin-induced organoid swelling at normal (FIG. 27C) or reduced (FIG. 27D) Wnt3a levels pre-incubated with DMSO, CFTR-inh172, GIyH-101 or both CFTR-inh172 and GIyH-101 (normal wnt3a: n=29, n=41, n=26, n=15; reduced Wnt3a: n=5, n=7, n=8, n=10) (mean±s.e.m.). All data is representative of at least three independent experiments.

Figure 28A:
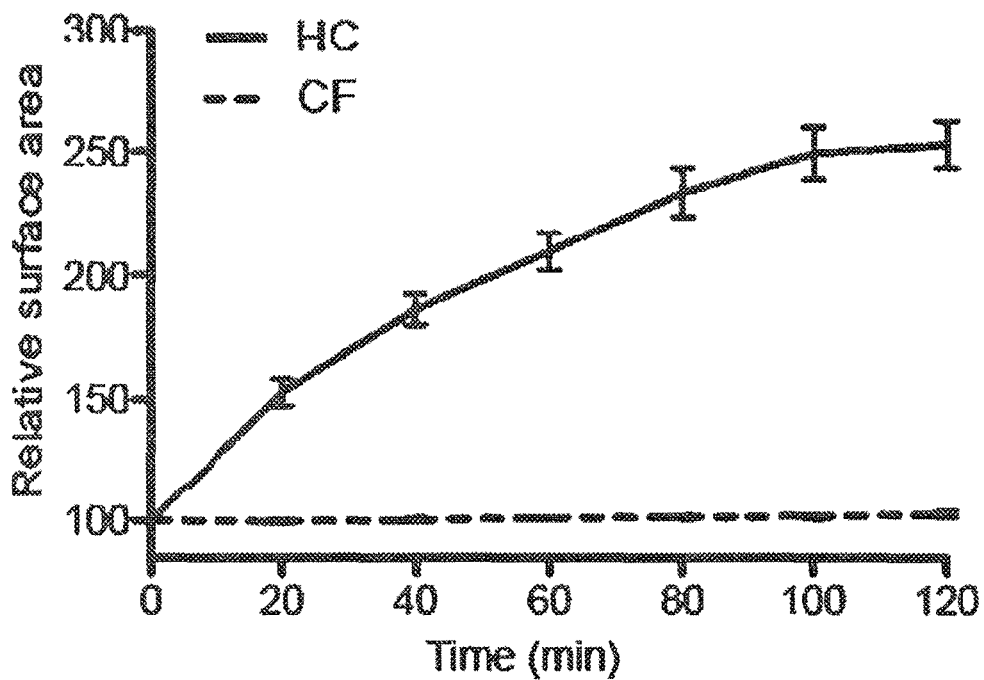
Figure 28B:
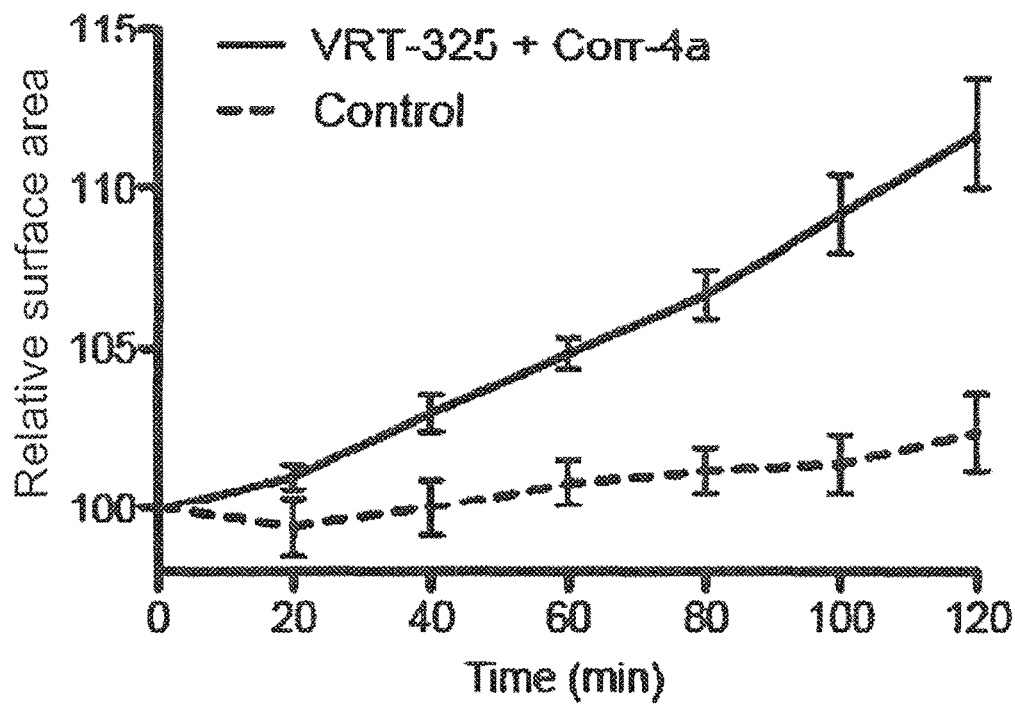

FIGS. 28A and 28B show absence of forskolin-induced swelling in organoids from a CF patient can be rescued by CFTR-correcting drugs. FIG. 28A shows forskolin-induced swelling in organoids from a CF patient containing homozygous CFTR-F508del is absent. HC is healthy control. FIG. 28B shows FIS increases in CF organoids upon incubation for 24 h with correctors VRT-325 and corr 4a.

Figure 29:
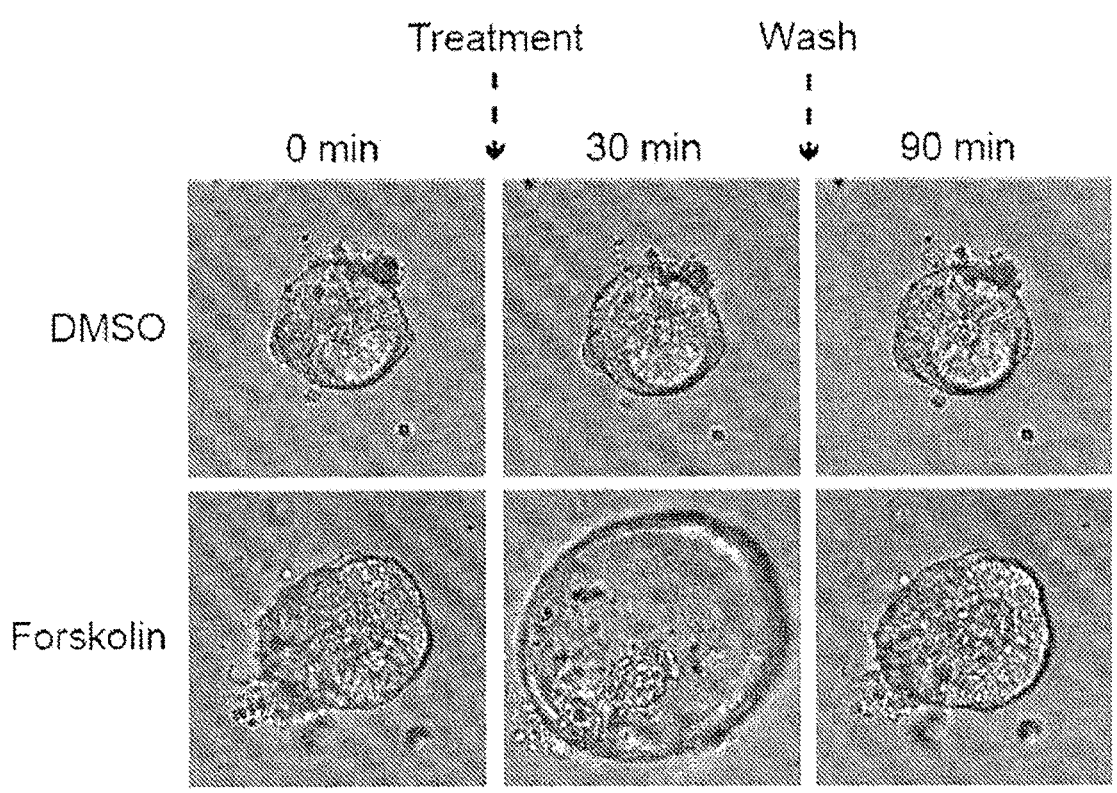

FIG. 29 shows light microscopy analysis of wild type murine organoids stimulated with forskolin or DMSO. Representative examples for the indicated timepoints after start of stimulation are shown. The forskolin-induced swelling (FIS) of organoids was reversed upon removal of forskolin by washing.

Figure 30:
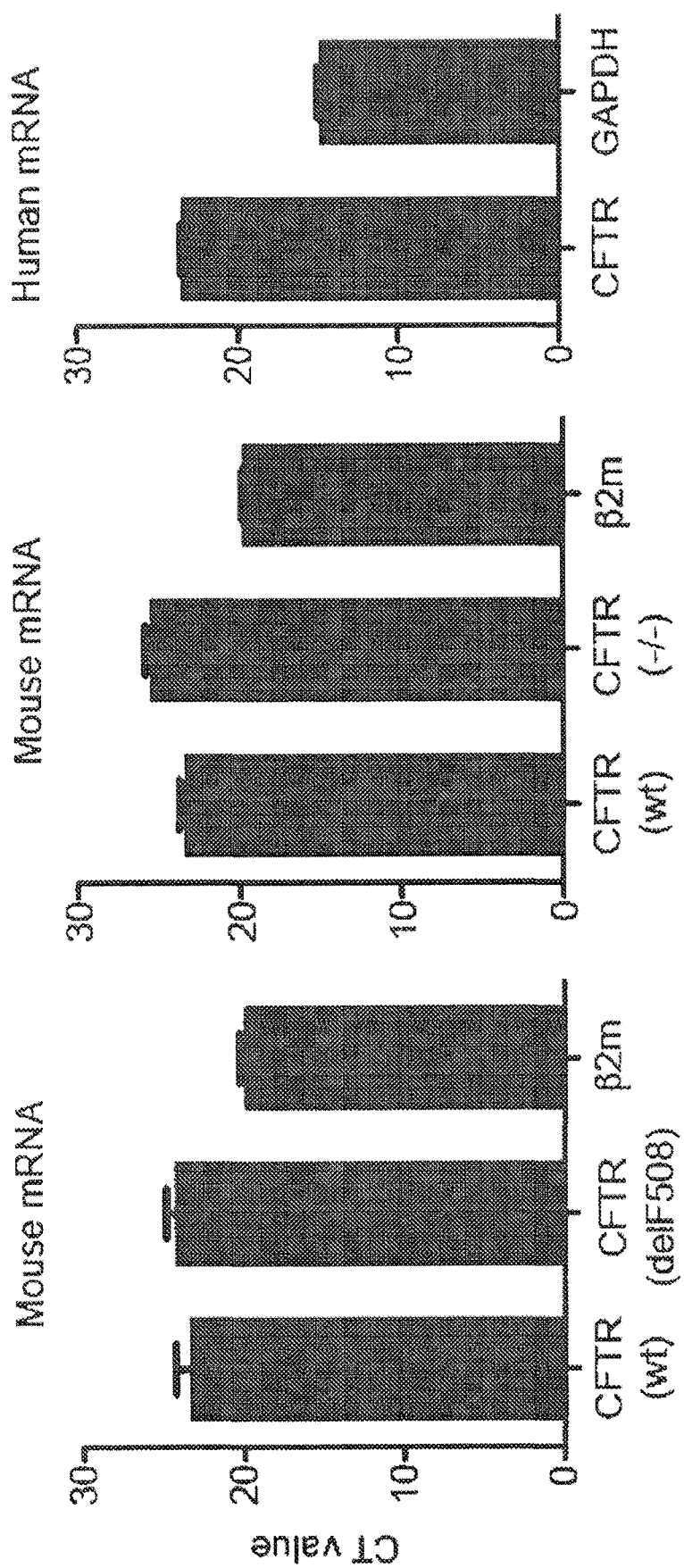

FIG. 30 shows CFTR mRNA is expressed in mouse and human organoids. The bars show real-time PCR CT values representing mRNA levels of CFTR, p2m or GAPDH isolated from CFTR-delF508 (left graph) or CFTR-/- (middle graph) organoids and their corresponding wild types, or human organoids.

Figure 31A:
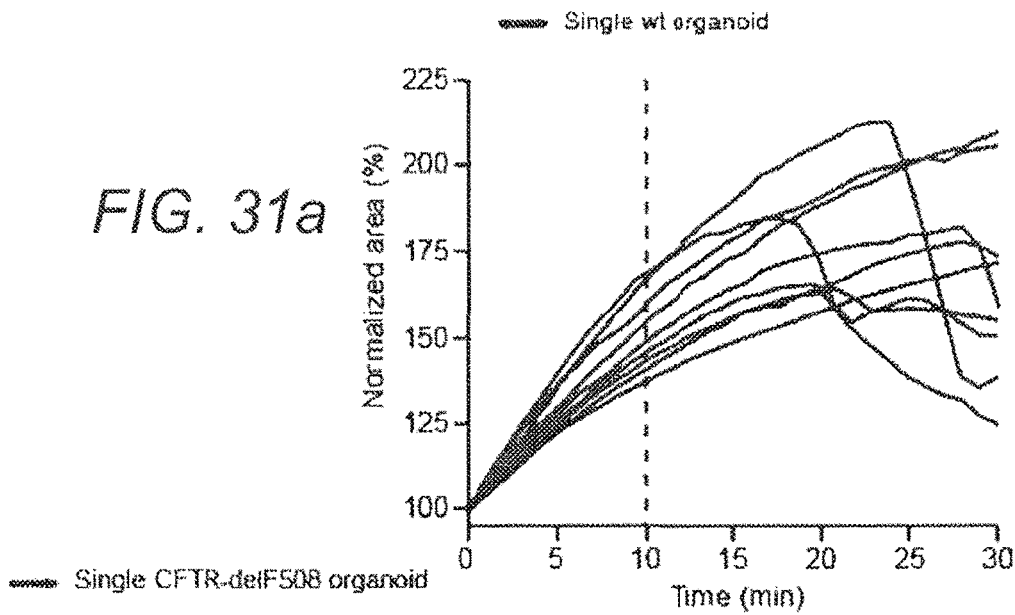
Figure 31B:
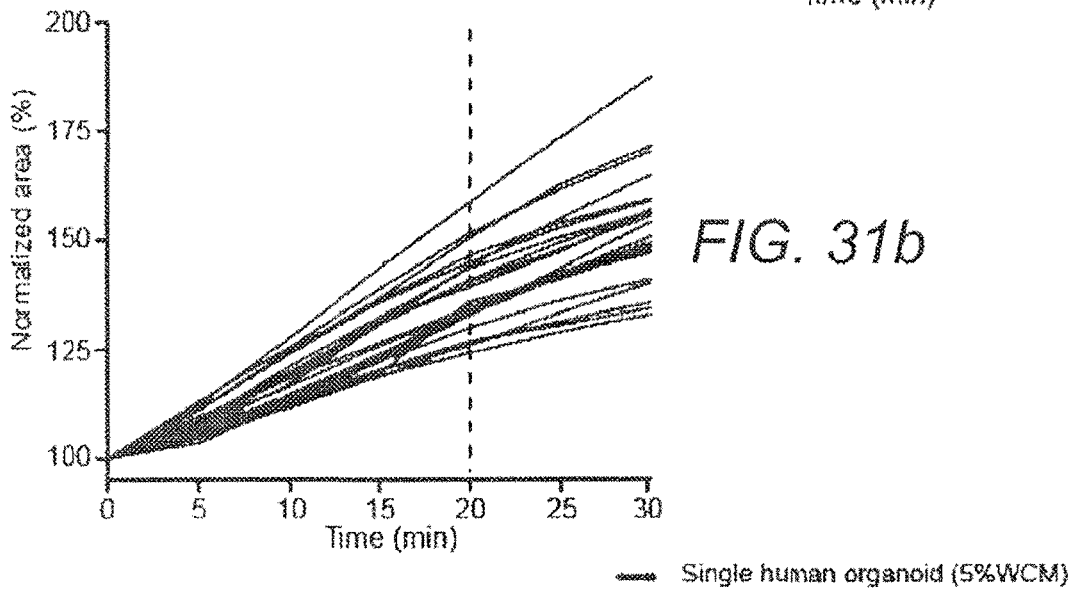
Figure 31C:
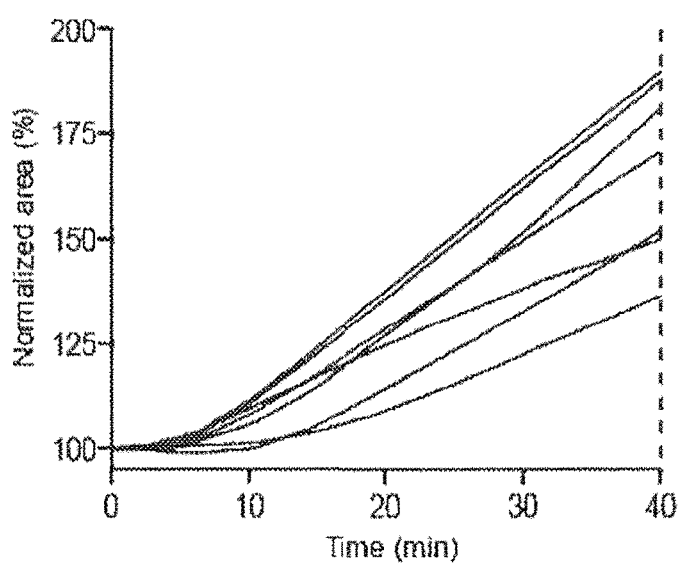

FIGS. 31A to 31C show gradual forskolin-induced swelling prevents organoid collision. Normalized surface area increase of individual forskolin-stimulated (FIG. 31A) wild type, (FIG. 31B) CFTR-delF508 (temperature-rescued) and (FIG. 31C) human (5% Wnt3a-conditioned medium, WCM)

organoids. The averaged forskolin-induced swelling of per organoids type was analysed up to different time points (dashed line).

Figure 32:
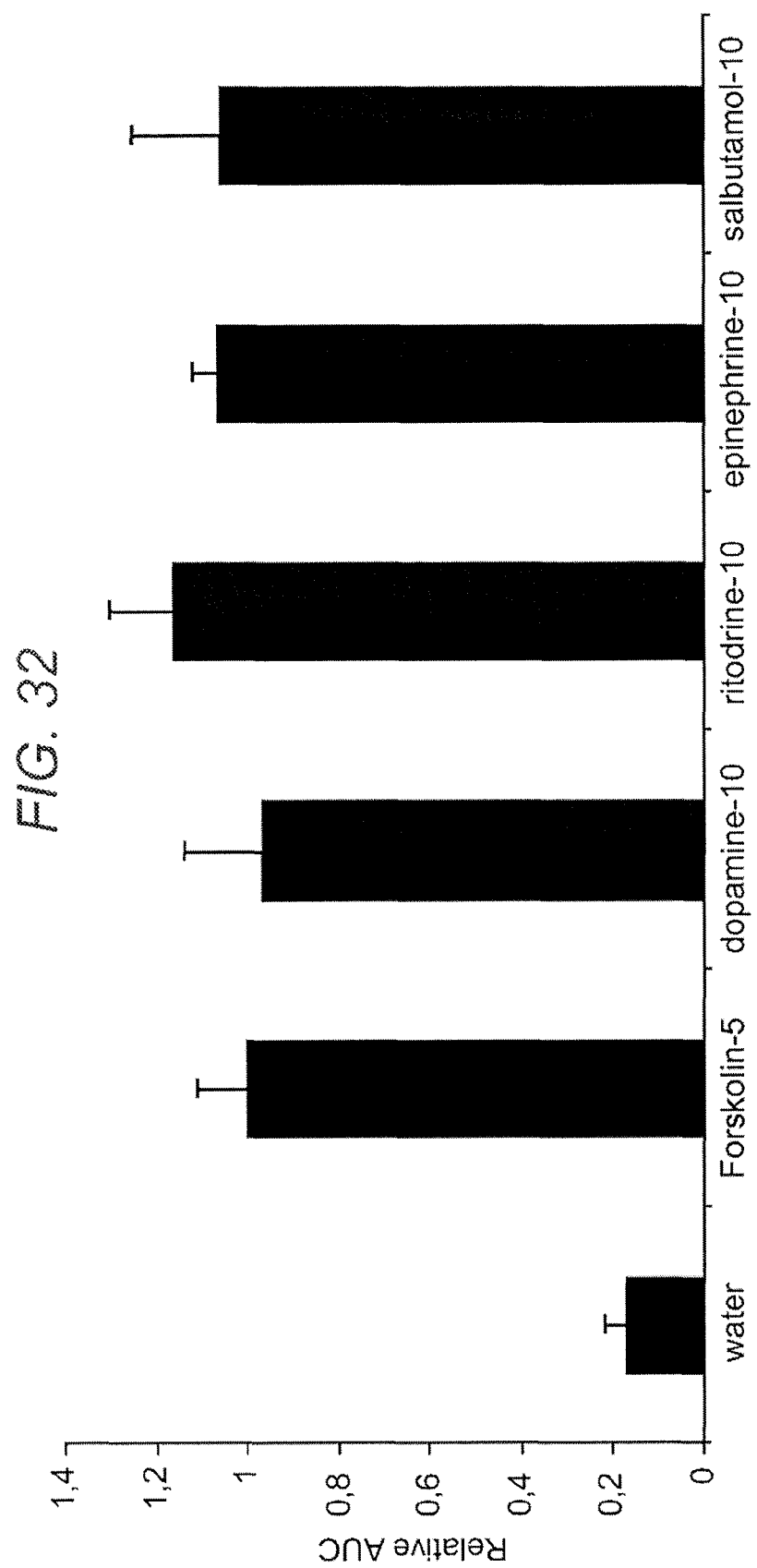

FIG. 32 shows forskolin-like swelling also occurs in response to dopamine, ritodrine, epinephrine and salbutamol. The figure shows the relative AUC for each of these compounds relative to forskolin.

EXAMPLES

Example 1

Figure 1:
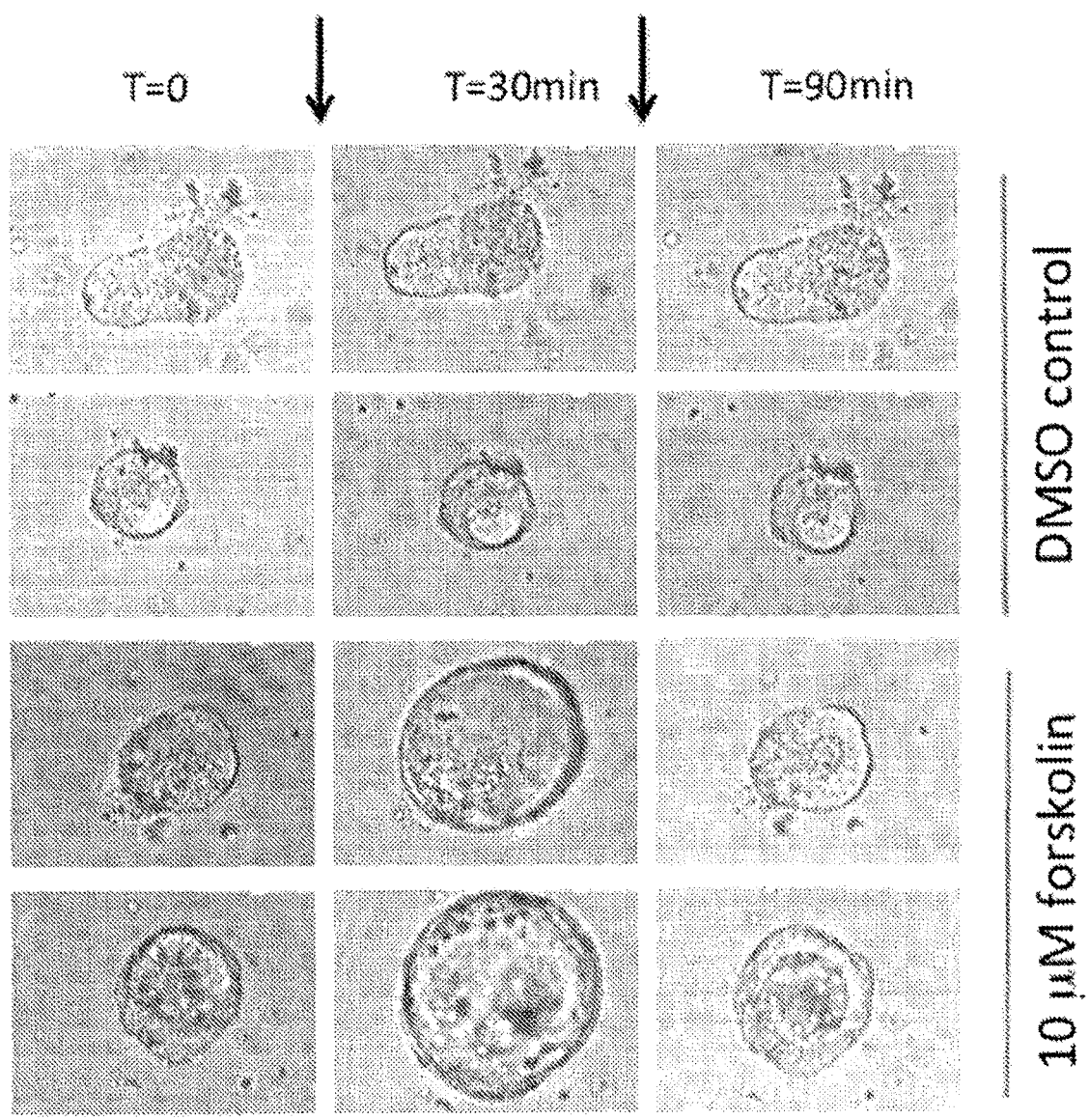
Figure 2:
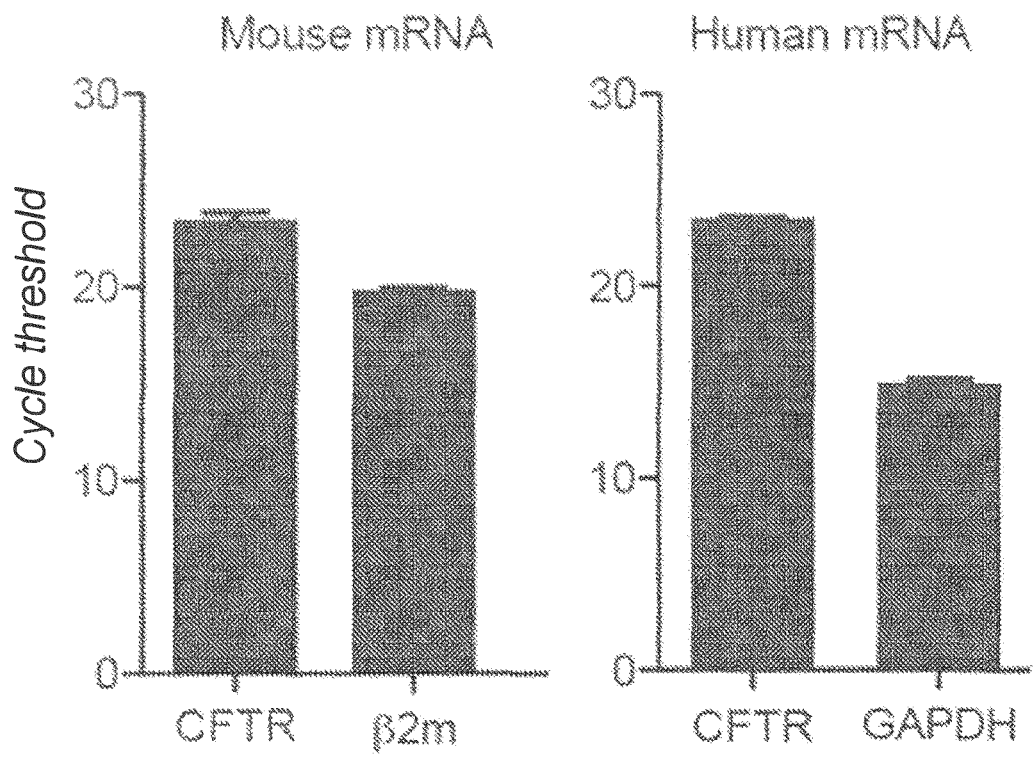
Figure 3:
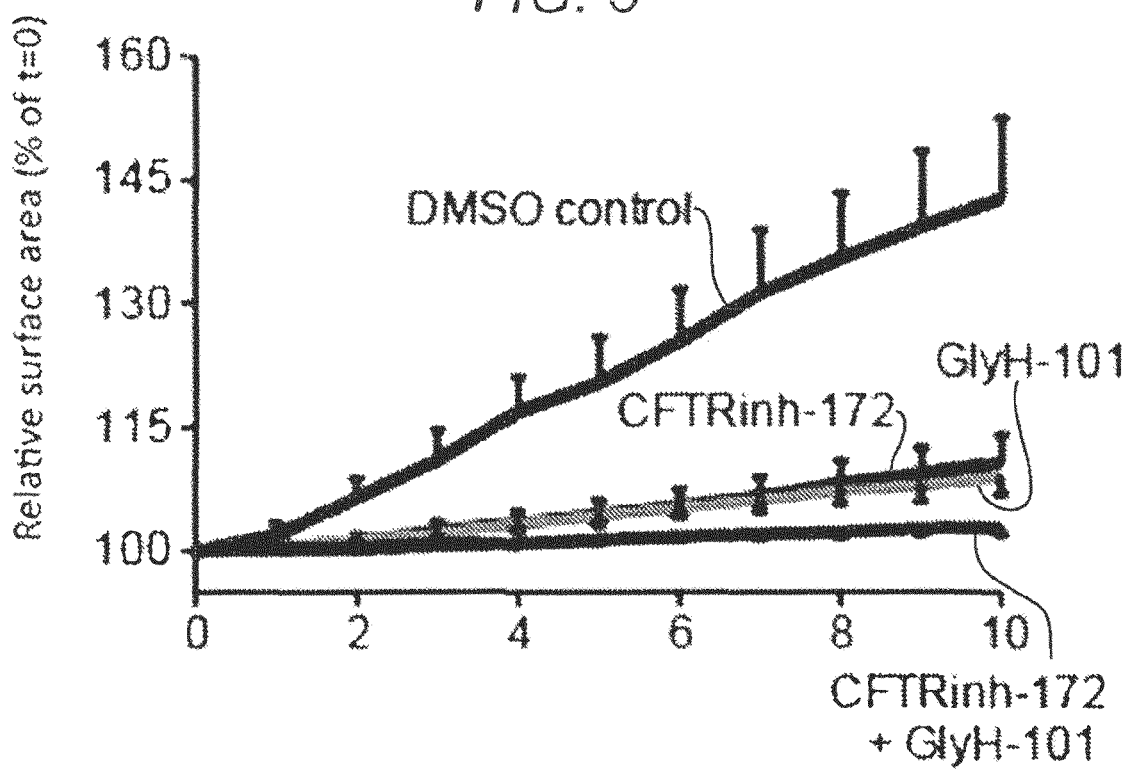
Figure 4A:
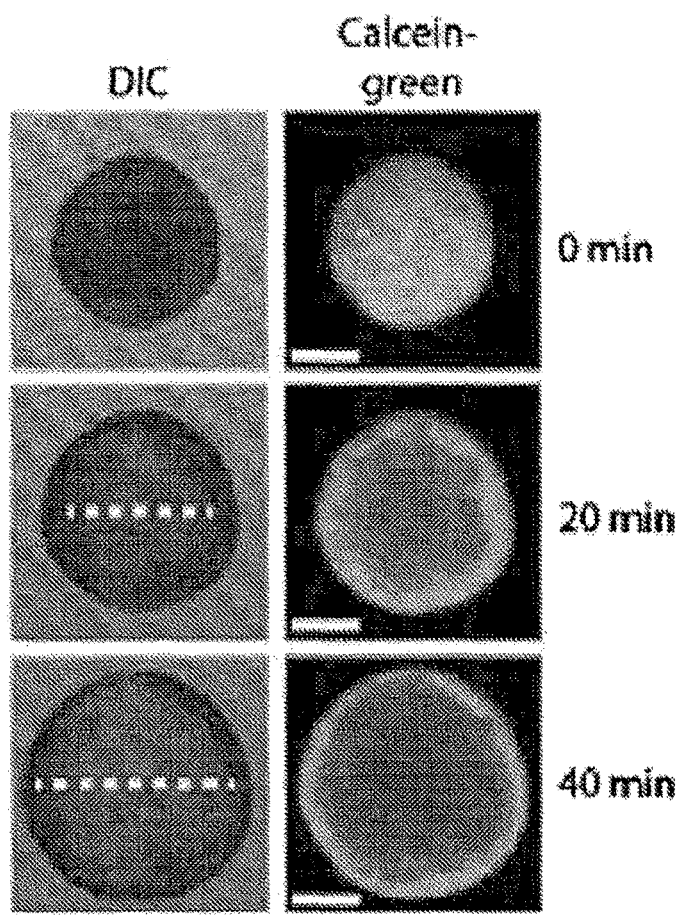
Figure 4B:
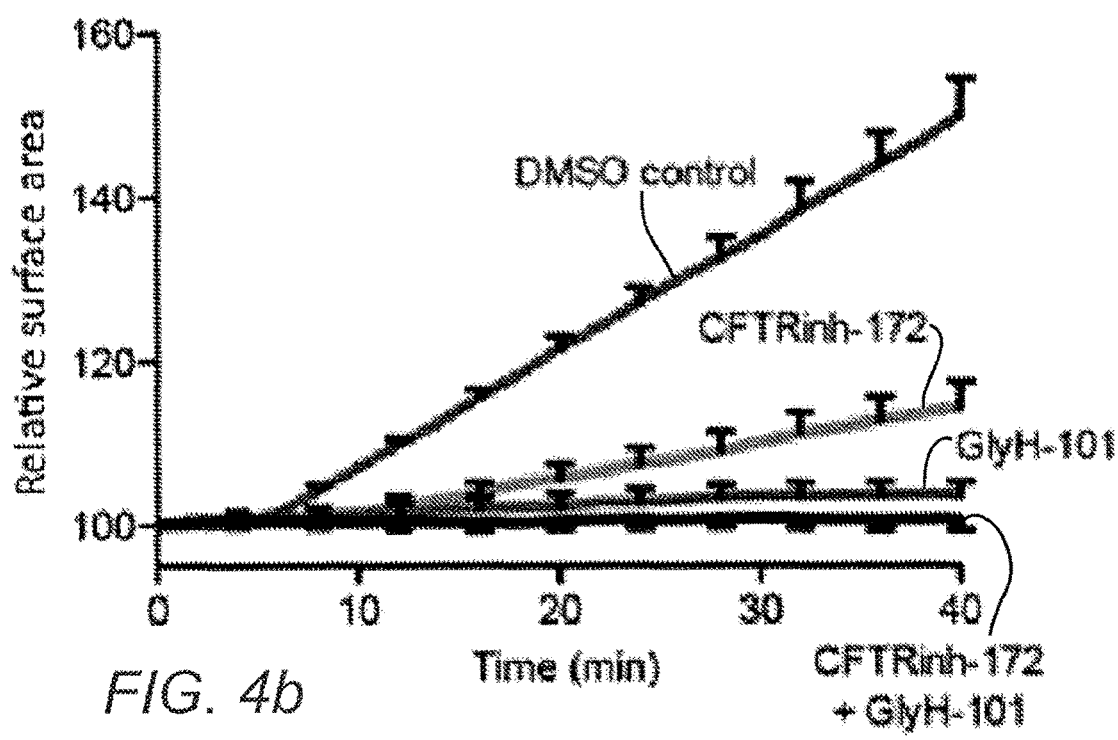

We here demonstrate a rapid, quantitative assay for CFTR function in a murine and human primary intestinal crypt-based culture method. This culture method enables intestinal stem cells to expand into closed organoids which mimic the structure of the intestine in vivo including a closed lumen on the apical membrane of the cells. Intestinal CFTR is predominantly expressed at the apical membrane of the crypt cells where its activation drives secretion of electrolytes and fluids. We have shown that forskolin, which raises intracellular cAMP and thereby activates CFTR, could mediate fluid-transport into the organoid lumen. Using live cell microscopy, we observed a rapid expansion of the lumen, and total organoid surface area when forskolin was added, while DMSO-treated murine organoids were unaffected (FIG. 1). The forskolin-induced swelling of organoids was reversed upon removal of forskolin by washing (FIG. 1). CFTR mRNA is expressed in murine and human organoids (FIG. 2) and forskolin-induced swelling was found CFTR-dependent by use of chemical inhibitors (mouse FIG. 3; human FIG. 4).

The above part of our invention describes the use of intestinal (small intestine and colon) organoids for measuring fluid uptake and secretion resulting in an increased or decreased size of the organoid. This size change is measured by imaging of the organoid and manual or automated measurement of the surface area, diameter, or content. The quantification of change in size can be used to demonstrate the disease and its severity. This is exemplified by comparison of forskolin-induced swelling in organoids grown from a healthy control or a CF patient carrying homozygous F508del mutations (FIG. 5A). This holds important implications for the use of this assay as diagnostic test to demonstrate cystic fibrosis.

Figure 5B:
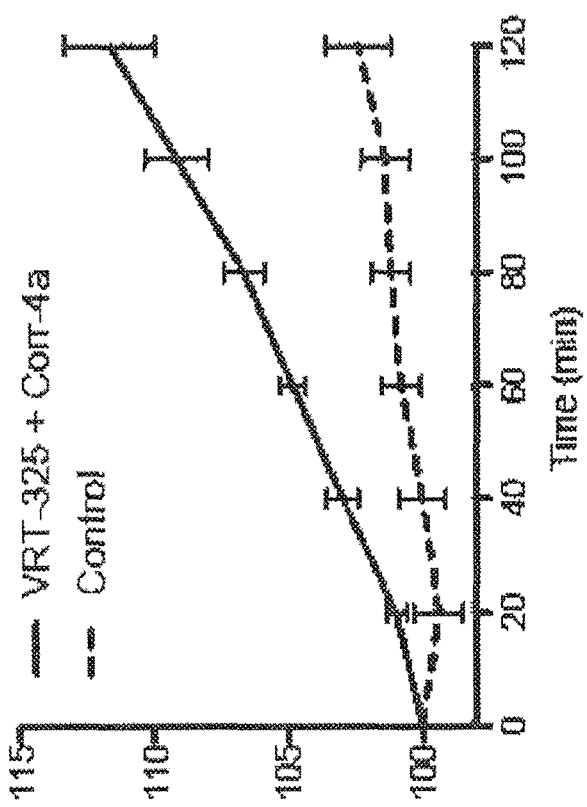
Figure 5A:
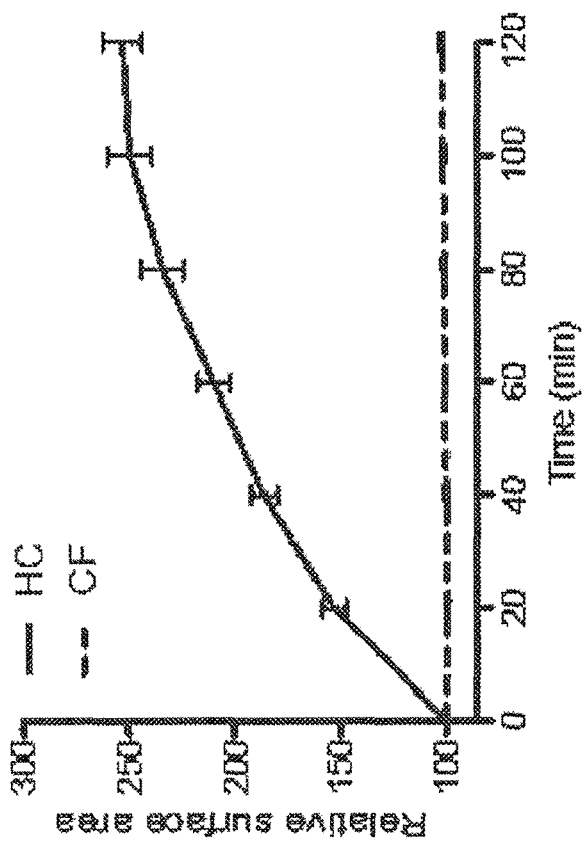

Our assay can also be used to measure the effect of existing or novel treatments, as we observed forskolin-induced swelling in CF organoids upon addition of drugs that are known to correct CFTR function in vitro (FIG. 5B). This suggests that our assay can be used to compare the activity of drugs between different patients in vitro to assess individual responses to CFTR-restoring drugs for patient-tailored personalized medicine purposes.

Mouse CFTR-delF508 organoids have higher residual CFTR activity than human counterparts (but is absent in mice deficient for CFTR) (FIGS. 6A to 6D), and respond to CFTR correction by temperature and compounds by increased forskolin-induced swelling. This shows that our assay can also be applied for CFTR-F508del restoring drugs in organoids derived from non-human species.

Figure 7:
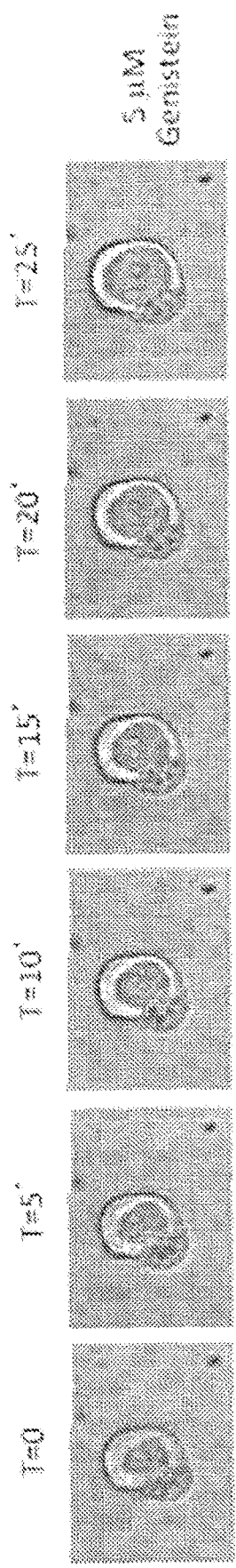
FIG. 7 shows genistein was added to organoid culture and rapid expansion was imaged for indicated timepoints (min).

We also observed that genistein, a known CFTR potentiator, can induce rapid organoid swelling, further indicating that compounds with CFTR potentiator activity can be identified using this assay (FIG. 7).

The method can be used to screen compound libraries for novel compounds that affect the fluid uptake and/or secretion of epithelial cells.

The method described above can also be used for other organs such as stomach or lung epithelium.

Figure 8:
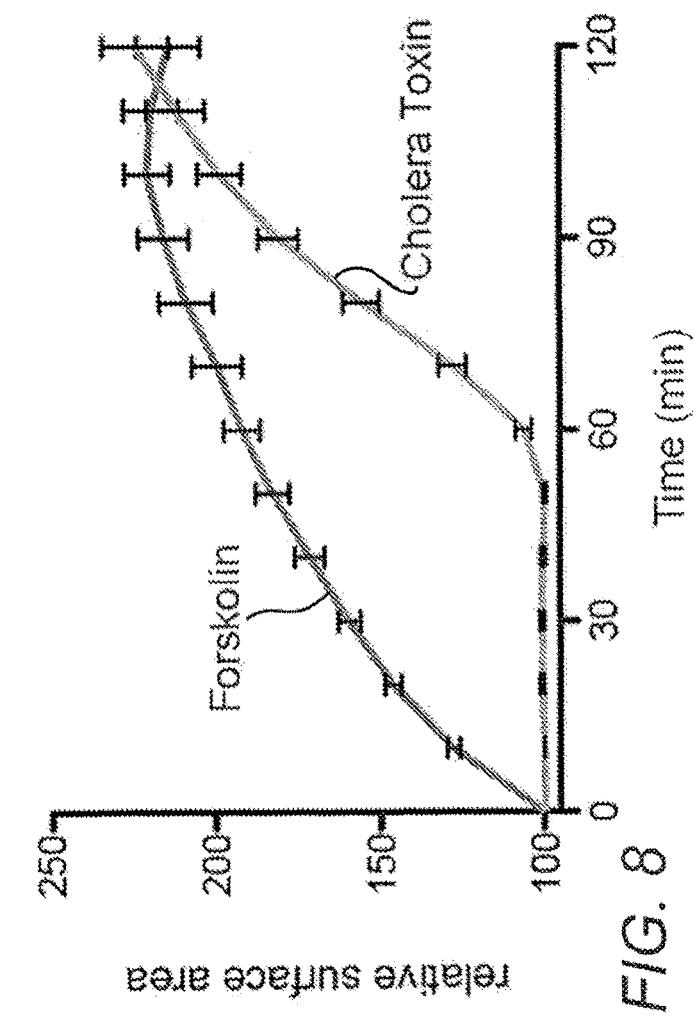
FIG. 8 shows human organoids were stimulated with forskolin or cholera toxin to stimulate fluid secretion. Both stimuli induce rapid organoid volumetric expansion indicated by surface area measurements.

The method can also be used to study the effect of other diseases that affect fluid uptake or secretion of epithelium of small intestine, colon, stomach, or lung. An example of this is the effect of Cholera Toxin (FIG. 8).

Potential Applications:

Application of the described technology is exemplified, but not limited to:

1) The use of small intestinal tissue derived organoids for drug screening. The effect of the drugs for treatment of CF is measured by size change of the organoids in response to forskolin or any other agent resulting in a size change of the organoids due to fluid uptake or secretion.
2) Personalised Medicine. The use of patient derived small intestinal organoids for the assessment of the individual responsiveness to certain treatment options.
3) CF diagnosis. CF diagnosis can be established by measurement of size change of organoids in response to forskolin or any other agent.
4) The method using the organoids can be used to study severity or effect of the mutation resulting in CF. The response of patient specific organoids to correctors that assist mutant CFTR folding or potentiators that assist CFTR gating and/or opening probability or other drugs used to treat CF.
5) The method using the organoids can be used to test individual patient response to drugs such as correctors or potentiators or other drugs used to treat CF.
6) The method using the organoids can be used to test effect of novel drugs to treat CFTR deficiency through CFTR function correction.
7) The method using the organoids can be used to test effect of novel drugs to treat CFTR deficiency by ways not directly influencing CFTR function.
8) The method using the organoids can be used by measuring a rapid increase in volume measured after a few minutes to 48 hours (e.g. 10 min).
9) The method using the organoids can be used by measuring a slow increase in volume measured after a few days to a few weeks.
10) The method using the organoids can be used for other diseases or afflictions resulting in altered fluid and electrolyte uptake or secretion of small intestine epithelium.
11) The applications-described in 1-10 can also be used in combination with colon or lung epithelium, or cells from other human tissues.
12) The applications-described in 1-10 can also be used in combination with organoids derived from non-human species.

Novelty

The method described makes use of organoids as previously described (Sato 2009, Sato 2011) which contain primary cells derived from patients. The novel finding is the rapid increase in the lumen and total surface area of the organoids of the small intestine in response to drugs targeting CFTR. This increase in size is affected by mutation of the CFTR gene and CF drugs that control CFTR. This led us to develop a novel technique for the measurement of the expansion of the organoids as a measure of the effect of CFTR mutation and drug treatments. This allows for the use of this method to efficiently screen drug treatment and or patients for effect on the uptake and secretion of fluid, the control of which is effected in several diseases such as CF and Cholera.

Procedure

Crypt Isolation and Organoid Culturing

Murine and human organoids were generated from isolated small intestinal or colonic crypts and maintained in culture by methods described previously by Sato et al in 2009 and 2011.

Organoid Labeling

For confocal live cell imaging experiments, organoids were labeled with different cell-permeable dyes that gain fluorescence upon metabolic conversion by living cells, including Cell Tracker-Orange, Cell Tracker-Green and Calcein-Green (all from Invitrogen). While incubation with Cell Tracker-Orange and Cell Tracker-Green resulted in poor cell staining, high background staining and accumulation of the dye in the organoid lumen, we found excellent organoids labeling with low background levels using Calcein-Green. We tested different labeling conditions, and found optimal cell staining upon 10 µM Calcein-Green incubation for 60 minutes.

Live Cell Imaging

We tested different assay setups, and found that organoids were most suitable for forskolin-induced swelling analysis one to two days after passaging, plated in a 96-wells plate in 5 µl matrigel. To improve penetration of compounds into the matrigel, we used matrigel dilutions up to 50%. Murine organoids were preincubated with CFTR inhibitors (50 µM) for 60 minutes, simultaneously with Calcein-Green. For optimal CFTR-inhibition effects in human organoids, we extended incubation time to 3 hours with simultaneous Calcein-Green staining during the last hour. Chemical compounds (10 µM) were preincubated for 24 hours in both human and mouse organoids. Calcein-Green-labeled organoids were stimulated with 5 µM forskolin and directly analyzed by confocal live cell imaging using the LSM Zeiss microscope.

Quantification of Organoid Swelling

Figure 9:
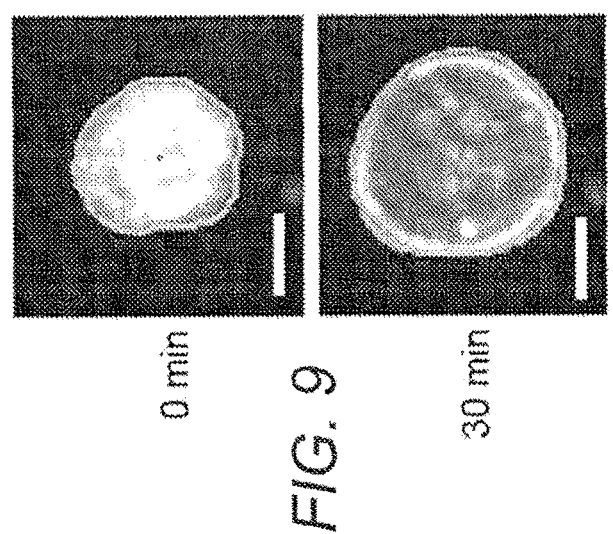
FIG. 9 shows a fluorescence confocal image of a calcein-green-labeled organoid with object recognition (green line) by volocity image analysis software at the start or after 30 minutes of forskolin stimulation.

We used Volocity quantification software to analyze organoids during forskolin stimulation. We started analyzing expansion of the lumen together with decrease in cell height of the epithelial monolayer. Under our labeling conditions, the software was not able to discriminate between cell layer and lumen due to the lack of contrast. Therefore, total and normalized organoid area increase was analyzed during forskolin-induced swelling, easily measured by the software (FIG. 9).

REFERENCES FOR EXAMPLE 1

Single Lgr5 stem cells build crypt-villus structures in vitro without a mesenchymal niche. Sato T, Vries R G, Snippert H J, van de Wetering M, Barker N, Stange D E, van Es J H, Abo A, Kujala P, Peters P J, Clevers H. *Nature.* 2009 May 14; 459(7244):262-5

Long-term expansion of epithelial organoids from human colon, adenoma, adenocarcinoma, and Barrett's epithelium. Sato T, Stange D E, Ferrante M, Vries R G, Van Es J H, Van den Brink S, Van Houdt W J, Pronk A, Van Gorp J, Siersema P D, Clevers H. *Gastroenterology.* 2011 November; 141(5):1762-72.

Example 2

We have recently established conditions allowing long-term expansion of epithelial organoids from human intestine, recapitulating essential features of the in vivo tissue architecture. Here, we apply this technology to study primary intestinal organoids of patients that suffer from cystic fibrosis (CF), a disease caused by cystic fibrosis transmembrane conductance regulator (CFTR) gene mutations. Forskolin induces rapid swelling of organoids derived from healthy controls (HC) or wild-type mice, which is strongly reduced in CF patients or F508del mutant mice and is absent in Cftr-null organoids. This phenomenon is phenocopied by CFTR-specific inhibitors. Forskolin-induced swelling of in vitro expanded rectal HC and CF organoids corresponds quantitatively with forskolin-induced anion currents in ex vivo freshly excised rectal biopsies. Function of F508del-CFTR is restored upon incubation at low temperature, as well as by CFTR-restoring compounds. This relatively simple and robust assay will facilitate diagnosis, functional studies, drug development and personalized medicine approaches in CF.

Introduction

The cystic fibrosis transmembrane conductance regulator (CFTR) protein functions as an anion channel, and is essential for fluid and electrolyte homeostasis at epithelial surfaces of many organs, including lung and intestine. The autosomal-recessive disorder cystic fibrosis (CF) is caused by mutations in the CFTR gene[1-3]. CF disease is highly variable, and patients have a median life expectancy of approximately 40 years. Loss-of-function mutations cause altered ion and fluid transport that result in accumulation of viscous mucus in the pulmonary and gastrointestinal tract. This is associated with bacterial infections, aberrant inflammation and malnutrition[4]. Over 1900 mutations have been identified, but the most dominant mutation (~67% of total mutant alleles world wide) is a deletion of phenylalanine at position 508 (F508del-CFTR) (genet.sickkids.on.ca). This causes misfolding, ER-retention and early degradation of the CFTR protein that prevents its function at the plasma membrane[5]. Other mutations in the CFTR gene that have been found in CF patients also impair protein folding or production, gating, conductance, splicing and/or interactions with other proteins[6].

Current therapies for CF are mainly symptomatic and focus on reduction of bacterial pressure, inflammation, and normalization of nutrient uptake and physical growth. In the last years, multiple compounds have been identified that target mutation-specific defects of the CFTR protein itself[6,7]. Clinical trials are currently performed using compounds that induce (i) premature stopcodon read-through, (ii) correction of plasma membrane trafficking of CFTR (correctors), and (iii) enhancement of CFTR gating (potentiators). Recently, a phase III clinical trial has been completed successfully for the potentiator VX-770 (Ivacaftor, Kalydeco) in CF patients with a G551D-CFTR mutation, demonstrating that mutation-specific drug targeting is feasible in CF[8]. Combination therapy of a corrector (VX-809)

and potentiator (VX-770) is currently assessed in a phase II clinical trial for the dominant patient group harboring the F508del-CFTR mutation.

Although these recent developments are very promising, the level of functional restoration of CFTR by these drugs is still limited[9-11]. In addition, patients show variable responses to these therapies due to yet undefined mechanisms[8,12-14]. The inability to predict a patient's responsiveness to a corrector compound limits clinical efficacy and drug registration. Together, this indicates that development of new compounds and screening of drug efficacy at the level of individual patients are urgently needed. Thus far, there is only a limited number of primary cell models available to screen for compounds that restore mutant CFTR function. When such an in vitro model can be further expanded to allow analysis of drug responses of individual patients, it may improve drug efficacy by selecting subgroups of responding patients.

Here, we demonstrate a rapid and simple quantitative assay for CFTR function in a murine and human primary intestinal crypt-based culture method that was recently developed[15-17]. This culture method enables intestinal stem cells to expand into closed organoids containing crypt-like structures and an internal lumen lined by differentiated cells, recapitulating the in vivo tissue architecture. Intestinal CFTR is predominantly expressed at the apical membrane of the crypt cells where its activation drives secretion of electrolytes and fluids[18-20]. We found that forskolin[21] induces rapid swelling of both human healthy control (HC) and murine wild-type organoids that completely depends on CFTR, as demonstrated by stimulation of intestinal organoids derived from CFTR-deficient mice or CF patients, or upon chemical inhibition of wild-type CFTR. Levels of forskolin-induced swelling by in vitro expanded rectal organoids are comparable with forskolin-induced anion currents measured in ex vivo human rectal biopsies. Temperature and chemical correction of F508del-CFTR function was easily detected by organoid-based fluid transport measurements, and responses to a panel of CFTR-restoring drugs were variable between rectal organoids derived from different F508del homozygous patients. This robust assay is the first functional readout developed in human organoids, and will facilitate diagnosis, functional studies, drug development, and personalized medicine for CF.

Results

Quantification of Forskolin-Induced Organoid Swelling

We first assessed whether forskolin, which raises intracellular cAMP and thereby activates CFTR, could mediate fluid secretion into the lumen of small intestinal organoids derived from wild-type mice. Using live cell microscopy, we observed a rapid expansion of the lumen and total organoid surface area when forskolin was added, while DMSO-treated organoids were unaffected (FIG. 10A). This forskolin-induced swelling (FIS) of organoids was reversed upon removal of forskolin by washing (FIG. 15).

Next, we quantified these responses by unbiased image analysis. We found excellent cell labelling whilst background levels of the surrounding matrigel remained negative using calcein-green, a cell-permeable dye that gains fluorescence and is retained within the cell upon metabolic conversion by living cells. The fluorescent intensity of calcein-green-labelled objects was on average >100 times larger as compared to background levels. We quantified FIS of organoids using live cell confocal microscopy and imaging software that calculated the relative increase in the total area of all fluorescent objects for each time point upon forskolin addition per well (representative examples of object recognition, and FIS for single organoids are indicated in FIGS. 10B and 10C; FIG. 16A). The majority of organoids respond to forskolin stimulation (FIG. 10D). Approximately 5-10% of structures that are either very small, or irregularly-shaped non-viable organoids do not respond to forskolin (FIGS. 16B and 16C). Since they only represent a minor fraction of the total organoid surface area in a well, quantification of FIS was not different with or without preselection of responding structures (FIG. 16D). Measurements of three independent wells show limited variation (FIG. 10E). We observed a dose-dependent relation between forskolin and increase of surface area over time (FIG. 10F). FIS of murine organoids is shown for the first 10 minutes, as some wild-type organoids burst and collapsed when stimulations longer than 10 minutes were performed (FIG. 17A). Together, these results show that forskolin-induced organoid swelling can be quantified by unbiased fluorescent image analysis.

Forskolin-Induced Swelling of Murine Organoids is CFTR Dependent

High levels of Cftr mRNA in these organoids supported a possible role for CFTR in forskolin-induced swelling (FIG. 18). To demonstrate that FIS is CFTR dependent, we used chemical inhibitors of CFTR[22,23], and Cftr[1-24] as well as F508del-CFTR mutant mice[25,26]. Pre-incubation (2 hours) with the CFTR inhibitors CFTR$_{inh}$-172[22] and GlyH-101[23] independently reduced FIS by respectively ~90% and ~75% compared to vehicle treatment (FIG. 11A). Their combined action fully prevented FIS at the time points analysed. We further confirmed CFTR-dependent FIS using organoids isolated from Cftr-deficient mice. FIS was absent when organoids of Cftr-deficient mice were assayed (FIGS. 11B and 11D). Calcein-green labelling was comparable between wild-type and mutant organoids, indicating that Cftr-deficient cells were viable. Organoids of F508del-CFTR expressing mice displayed low but detectable FIS, suggesting residual CFTR activity, consistent with earlier observations in this mouse model[25,26] (FIGS. 11C and 11E). In support of this, the attenuated FIS of F508del-CFTR organoids was sensitive to CFTR$_{inh}$-172 (FIG. 11F). Together, these data demonstrate that FIS in murine organoids is completely dependent on CFTR.

Temperature and Chemical Correction of Murine F508del-CFTR

To further indicate that the assay is sensitive to correction of CFTR function, we performed temperature-rescue experiments, a widely accepted method to increase F508del-CFTR function[27]. F508del-CFTR misfolding is reduced at 27° C. leading to enhanced levels of functional CFTR at the plasma membrane. We observed increased levels of FIS upon overnight incubation at 27° C. (FIG. 11F). Chemical inhibition of CFTR activity strongly reduced FIS in organoids grown at reduced and normal temperature (FIG. 11F). We next used the chemical correctors VRT-325[28] and Corr-4a[29] to restore F508del-CFTR function. Pre-incubation (24 hours) with VRT-325 enhanced FIS whereas Corr-4a only slightly improved FIS, and was additive to correction by VRT-325 (FIG. 11G). Chemical inhibition of CFTR indicated that the VRT-325- and Corr-4a-induced FIS was fully CFTR dependent. Collapse of rescued F508del-CFTR organoids was rarely observed (FIG. 17B). Collectively, these results demonstrated that FIS of murine organoids can reveal functional restoration of F5O$_8$del-CFTR by correction approaches.

Forskolin-Induced Swelling of Human Organoids is CFTR Dependent

We next applied our assay conditions to human intestinal organoid cultures. While both mature CFTR (C-band, 170 kDa) and immature CFTR (B-band, 130 kDa) was detected by Western blot analysis in human HC organoids, only immature CFTR was detected in CF organoids. No CFTR B- or C-band was observed in organoids carrying E60X[30] and a non-reported allele that induces a frame shift in NBD2 at residue 1250 (4015delATTT). E60X and the newly identified 4015delATTT mutation most likely result in the production of a truncated, non-functional protein. CFTR B-band and C-band specificity was further indicated by Endo H and PNGase F treatment[5], respectively (FIG. 12A). CFTR expression at the apical membrane was demonstrated in healthy control organoids by immunocytochemistry, but not in CF organoids, as indicated by colocalization with apical actin (FIG. 12B). In agreement with the murine experiments, we observed rapid forskolin-stimulated swelling of healthy control organoids that was reduced upon 3 hours pre-incubation with CFTR$_{inh}$-172 or GlyH-101, and completely inhibited by combined treatment with these inhibitors (FIG. 12C). Human organoids show somewhat slower kinetics when compared to murine organoids and rarely collapse during long-time forskolin treatment (FIG. 12C; FIG. 17C).

We analysed FIS in a large number of intestinal organoids primarily derived from rectum but also from duodenum, ileum, and colon. We observed strong FIS in organoids derived from HC subjects (rectal organoids from HC or CF patients are shown in FIG. 11D, all organoids are presented in FIG. 19A). Rectal organoids derived from patients that are compound heterozygote for F508del and A455E[31], a genotype that is associated with mild CF[3], clearly displayed reduced FIS levels compared to healthy control organoids. Patients with severe CF genotypes (homozygous for F508del; compound heterozygous for F508del and L927P[33], or G542X[31]) displayed much lower but still detectable FIS that was variable between individual patients (FIG. 12E). No FIS was measured in E60X/4015delATTT organoids. Chemical inhibition of CFTR abolished all FIS responses of CF organoids (FIGS. 19B and 19C).

FIS measurements of in vitro expanded rectal HC organoids or CF organoids subdivided into severe and mild genotypes correlated tightly with forskolin-induced intestinal current measurements (ICM) performed on rectal suction biopsies[34,35] from which these organoids originated (FIG. 12F). Most ICM tracings of biopsies from individual patients showed residual forskolin-induced anion currents that corresponded with a quantitatively similar CFTR-dependent forskolin response in the FIS assay (a representative ICM tracing, a paired analysis of FIS and ICM for individual patients and Spearman's rank correlation analysis (R=0.84, p=0.001) is provided in FIGS. 20A to 20C, respectively). Together, these data indicated that FIS in human organoids can accurately measure CFTR function, and show that residual CFTR function in intestinal rectal organoids may differ between individuals homozygous for the F508del-CFTR mutation.

Chemical CFTR Correction in Human Rectal CF Organoids

We next assessed if F508del-CFTR function could be increased in human organoids by low temperature incubation, or by the known chemical correctors VRT-325, Corr-4a, C8 (cftrfolding.org), VX-809[36] and the potentiator VX-770[9]. Incubation of F508del homozygous organoids at low temperature increased FIS as expected, and was inhibited by chemical CFTR inhibitors (FIG. 13A). We next established dose-response curves for single treatment of VX-809 (upon 24 h pre-incubation) or VX-770 (added simultaneously with forskolin) in organoids from 6 homozygous F508del patients (FIG. 13I), and measured EC50 values of 135±40 nM, and 161±39 nM, respectively. These dose-response curves are within ranges previously reported in human bronchial epithelial cells[9,36]. The combination of VX809 and VX770 induced increased levels of FIS, which was abolished by chemical CFTR inhibition (representative examples are shown in FIG. 13C). Next the capacity of various correctors to restore FIS upon 24 h pre-incubation was analysed in F508del homozygous organoids. All correctors increased FIS albeit with a different efficacy (FIGS. 13D to 13F; see FIG. 21 for responses in non-rectal organoids). Increased FIS responses by combination therapies were completely inhibited by the presence of CFTR inhibitors. We observed that VRT-325/Corr-4a or C$_8$/Corr-4a synergistically increased FIS (see also FIG. 22), which was in clear contrast with the additive effect of VRT-325/Corr-4a treatment observed in murine organoids (FIG. 11G). These data indicate that FIS can reliably measure correction or potentiation of F508del-CFTR.

Differential Responses to CFTR-Restoring Drugs in Rectal Organoids

We next studied FIS responses to a panel of CFTR restoring drugs in rectal organoids derived from 9 individuals harbouring various severe CFTR mutations, including 6 F508del homozygous patients. Between the F508del homozygote organoids, we observed differences in drug-induced FIS (FIGS. 14A to 14C). In general, FIS was variable between organoids upon incubation with single drugs, and the distribution of high and low responders was unique for a restoration approach (FIGS. 14A to 14C; patient order is similar to FIG. 12E in the 'Severe CF' panel). CF5 appears to be a general low responder to any corrector or VX-770, but showed an exceptionally small response to VRT-325. CF3 and CF5 organoids have similar responses to VX-809, but differ in their response to C$_8$. We observe that combinations of VRT-325 and Corr-4a in general synergized more strongly to induce FIS than C$_8$ and Corr-4a. The measured FIS over expected FIS (additive values of single treatment; illustrated in FIG. 22) is rather constant among most patients. All F508del compound heterozygote organoids also respond to correction (see FIG. 23 for F508del/A455E organoids), but no correction or potentiation was observed in E60X/4015delATTT organoids (FIGS. 14A to 14C). In this case the failure to correct CFTR is expected because no CFTR B- or C-band was detected in these organoids by Western blot (FIG. 12A). We next compared the drug responses of F508del organoids to FIS levels of mock-treated mild CF or HC organoids (FIG. 14D). This comparison indicated that VX-809 is the most potent corrector, and that combined treatment with VX-809 and VX-770 induces FIS beyond the levels observed in F508del/A455E organoids, reaching ~60% of HC levels. Together, these results demonstrate that the potency of CFTR-targeting compounds to restore CFTR function varies widely between organoids of individual CF patients, including homozygotes for F508del-CFTR.

Discussion

Collectively, our results indicate that forskolin-induced swelling of both mouse and human intestinal organoids is CFTR dependent. The rapid increase in surface area induced by forskolin likely results from the near-physiological characteristics of intestinal organoids. Previous data indicate that forskolin can increase luminal expansion in organoid-like structures grown from renal MDCK, colonic LIM1863 cell lines or murine intestinal spheroids,[20,37,38] but the larger amplitude and rate of the FIS response likely results from higher CFTR expression levels in the primary tissue culture model used here.

Fluid transport measured by FIS in rectal organoids correlated to the ICM performed on the corresponding rectal suction biopsies. This fluid transport assay can therefore be a valuable supplement to the electrical measurements of CFTR function currently carried out in CF centres and may serve to complement data obtained by ICM. Using ICM and FIS, we found that most F508del-CFTR patients showed some residual CFTR function, suggesting that F508del-CFTR is expressed at the apical surface at low levels**[1]. This is also supported by the induction of FIS by the potentiator VX-770 in the absence of correctors, an effect that was previously reported for human bronchial epithelial cells[9]. Clinical data also support the concept that F508del-CFTR is expressed at low levels in the apical membrane of epithelia from F508del homozygous CF patients[42,43].

The paired FIS and ICM allows comparison of fluid secretion rates and ion fluxes as measured by ICM. Based on the geometry of the organoids during FIS, and the assumptions that the average organoid lumen is a sphere and that the average swelling is similar in all three dimensions and linear over the time course of an experiment, we calculated an initial fluid secretion rate of $26\pm23$ $\mu l$ $h^{-1}$ $cm^{-2}$ in HC organoids (corresponding with an estimated $1.0\times10^2$ $\mu Amp/cm^2$ based on isotonic chloride secretion). When we assume isotonic chloride secretion during ICM, we estimated that the measured currents would correspond with an approximate fluid secretion rate of 12 $\mu l$ $h^{-1}$ $cm^{-2}$. This rate largely exceeds values reported previously for cysts from MDCK cells[44], and for airway epithelium[45].

This study clearly demonstrates that FIS can be restored by drugs with known CFTR-restoring capacity. Interestingly, we observed that drug responses of organoids are variable between CF patients, even between F508del-CFTR homozygous organoids. This raises the possibility that this in vitro assay may predict in vivo drug-responsiveness of individual patients. An ideal therapeutic model for CF would be to screen effectiveness of available CFTR-restoring drugs directly after CF diagnosis to optimize treatment at the personal level before disease onset. Personalized medicine approaches may also facilitate the development and approval of drugs to which only subgroups of patients respond, and limit the economic risks associated with drug research. Furthermore, it can be used for approval of drugs in patients that are genotypically mismatched with drugs that have been validated for a specific CFTR-genotype. Interim phase II results of a current trial published on websites of the North American Cystic Fibrosis Foundation (cff.org) and Vertex (vrtx.com) indicate that drug-responses to VX-809 and VX770, or VX-770 monotreatment[14], in CFTR F508del subjects are highly variable between patients. However, the predictive potential of organoid-based CFTR function measurements for in vivo drug responsiveness remains to be established.

Currently, patient-specific drug responses may be predicted using ex vivo rectal biopsies[4] or primary airway tissue culture models[47]. Compared with these techniques, organoid cultures appear superior in allowing the generation of large and robust data sets from individual patients. CFTR function analysis in organoid cultures is relatively easy, fast and robust. The organoids auto-differentiate into tissue-recapitulating structures in 96-well plates that allows measurement of up to 80 organoids per well and up to 96 conditions per experiment. In this format, dose-response curves measured in triplicate for multiple drugs per individual patient can be easily generated at multiple culture time points as demonstrated in this study.

Using the image analysis approach described here, higher throughput approaches to identify novel compounds that restore CFTR function may be developed when automated plating and stimulation of organoids is feasible. When we compare the drug responses in organoids with the limited clinical data that has been published in F508del-CFTR homozygous patients[13,14] (cff.org), only the combination treatment of VX-809 and VX-770 has been reported to improve lung function in approximately 50% of F508del homozygous patients. This combination induces approximately 1.5 fold higher FIS levels in F508del-CFTR homozygous organoids as compared to untreated F508del/A455E organoids, and up to 60% of FIS levels of HC organoids. It is not uncommon that treatment effects in in vitro models are superior to effects measured in vivo, but the fold correction in the FIS assay also exceeds the correction in cultured human bronchial epithelium by approximately 2-fold[9,36]. This may indicate that tissue-specific factors may control corrector efficacy. It is also likely that FIS rates are underestimated in HC when CFTR expression is no longer rate limiting for FIS beyond a particular threshold by e.g. basolateral ion transport. These data may suggest that novel CFTR-restoring drugs may have clinical impact when FIS reaches levels up to ~60% of wild-type FIS.

Two important aspects of organoid cultures render this technology highly suitable for follow-up studies. Firstly, organoids can be greatly expanded while maintaining intact stem cell compartments during long-term culture (over 40 passages)[16]. Generation of large cell numbers will aid cell biological and biochemical studies of CFTR-dependent cellular alterations, and is a prerequisite for high throughput screens. Secondly, organoids can be stored in liquid nitrogen, allowing generation of primary cell banks from CF patients. These can be used to identify and study cellular factors associated with clinical phenotypes in CF patients, and would allow for patient-specific analysis of newly developed drugs using materials that have been previously acquired.

In addition to possible applications in CF research, this assay may be suitable for development of drugs to treat secretory diarrhoea, a life threatening condition that results from CFTR hyper-activation by pathogenic toxins such as cholera toxin[48] (FIG. 24), and for electrolyte homeostasis studies in general.

In summary, we described a quick and robust assay for quantification of CFTR function using primary intestinal culture model that recapitulates essential features of the in vivo tissue architecture. This relatively simple assay will facilitate diagnosis, functional studies, drug development as well as personalized medicine approaches in CF.

METHODS

Mice

Cftr$^{tm1Cam}$ knockout mice (Cftr$^{1-}$)[24] were back-crossed with FVB mice and Cftr$^{tm1eur}$ (F508del-CFTR)[25,26] were back-crossed with C57Bl/6 (F12) mice. Congenic FVB Cftr$^{1-}$ mice or C57Bl/6 F508del-CFTR mice were used with their wild-type littermates. The mice were maintained in an environmentally controlled facility at the Erasmus Medical Center Rotterdam and approved by the local Ethical Committee.

Human Material

Approval for this study was obtained by the Ethics Committee of the University Medical Centre Utrecht and the Erasmus Medical Centre Rotterdam. Rectal HC and CF organoids were generated from four rectal suction biopsies after intestinal current measurements (ICM) obtained (i) during standard CF care (E60X/4015ATTTdel; F508delG542X; F508del/L927P; 5× F508del/F508del), (ii) for diagnostic purposes (1× HC) or (iii) during voluntary participation in CF studies approved by the local Ethics Committee (2× HC, 1× F508del/F508del). Material from a F508del-CFTR homozygous CF patient and a healthy control was derived from proximal ileum rest-sections upon surgery due to meconium ileus (Material was kindly provided by Dr K. Tenbrock, Department of Pediatrics, the RWTH Aachen University). Four duodenal biopsies were obtained from 2 CF patients by flexible gastroduodenoscopy to generate F508del/F508del and F508del/Exon17del organoids. The same procedure was used to obtain 4 biopsies from 2 patients with suspected celiac disease. The biopsies were macroscopically and pathologically normal and used to generate HC organoids.

Crypt Isolation and Organoid Culture from Murine Intestine

Murine organoids were generated from isolated small intestinal (SI) crypts and maintained in culture as described previously[15]. Rspo1-conditioned medium (stably transfected Rspo-1 HEK293T cells were kindly provided by Dr. C. J. Kuo, Department of Medicine, Stanford, CA) was used instead of recombinant Rspo-1 and added to the culture medium at a 1:10 dilution. Cftr, and F508del-CFTR organoids were obtained from proximal and distal SI segments, respectively. Organoids from Passage 1-10 were Used for Confocal Imaging.

Crypt Isolation and Organoid Culture from Human Biopsies

Crypt isolation and culture of human intestinal cells have been described previously[16]. In short, biopsies were washed with cold complete chelation solution and incubated with 10 mM EDTA for 30 (small intestine) or 60 (rectum) minutes at 4° C. Supernatant was harvested and EDTA was washed away. Crypts were isolated by centrifugation and embedded in matrigel (growth factor reduced, phenol-free, BD bioscience) and seeded (50-200 crypts per 50 µl matrigel per well) in 24-well plates. The matrigel was polymerized for 10 minutes at 37° C. and immersed in complete culture medium: advanced DMEM/F12 supplemented with penicillin/streptomycin, 10 mM HEPES, Glutamax, N2, B27 (all from Invitrogen), 1 µM N-acetylcysteine (Sigma) and growth factors: 50 ng/ml mEGF, 50% Wnt3a-conditioned medium (WCM) and 10% Noggin-conditioned medium (NCM), 20% Rspo1-conditioned medium, 10 µM Nicotinamide (Sigma), 10 nM Gastrin (Sigma), 500 nM A83-01 (Tocris) and 10 µM SB202190 (Sigma). The medium was refreshed every 2-3 days and organoids were passaged 1:4 every 7-10 days. Organoids from passage 1-10 were used for confocal live cell imaging. For production of WCM and NCM, Wnt3a-producing L-Cells (ATCC, nr: CRL-264) were selected for high expressing sub-clones and human full-length noggin was stably transfected into HEK293T cells, respectively (both were kindly provided by the Clevers Laboratory). Amounts and activity of the expressed factors in each batch were assessed using dot blots and luciferase reporter plasmids (TOPflash and FOPflash; Millipore) as described previously[49,50].

Stimulation Assays

Human or mouse organoids from a 7 day-old culture were seeded in a flat-bottom 96-well culture plate (Nunc) in 5 µl matrigel commonly containing 20-80 organoids and 100 µl culture medium. One day after seeding, organoids were incubated for 60 minutes with 100 µl standard culture medium containing 10 µM calcein-green (Invitrogen). For optimal CFTR inhibition, organoids were pre-incubated for 2h (mouse) or 3h (human) with 50 µM CFTR$_{inh}$-172, 50 µM GlyH-101 or their combined treatment (both from Cystic Fibrosis Foundation Therapeutics, Inc). After calcein-green treatment (with or without CFTR inhibition), 5 µM forskolin was added and organoids were directly analyzed by confocal live cell microscopy (LSM710, Zeiss, 5× objective). Three wells were used to study one condition and up to 60 wells were analyzed per experiment. For CFTR correction, organoids were pre-incubated for 24 hours with 10 µM VRT-325, 10 µM Corr-4a, 10 µM C$_8$ (all from Cystic Fibrosis Foundation Therapeutics, Inc), 3 µM VX-809 (Selleck Chemicals LLC, Houston, USA) or combinations as indicated. For CFTR potentiation, 3 µM VX-770 (Selleck Chemicals LLC) was added simultaneously with forskolin. Dilutions of VX-809 and VX-770 were used as indicated in FIG. 13B.

Quantification of Organoid Surface Area

Forskolin-stimulated organoid swelling was automatically quantified using Volocity imaging software (Improvision). The total organoid area (XY plane) increase relative to T=0 of forskolin treatment was calculated and averaged from three individual wells per condition. The area under the curve (AUC) was calculated using Graphpad Prism.

Statistical Analysis

A Kolmogorov-Smirnov test was used to test whether the ICM and FIS data were normally distributed. A paired student's T-test was used to compare FIS with or without pre-selection of responding organoids (FIG. 16D). A Spearman's rank correlation test was used to correlate ICM measurements with organoid swelling (FIG. 20C). A p-value <0.05 was considered as statistically significant. All data were analyzed in SPSS statistics version 20.0 for Windows.

RNA Isolation and qPCR

From human duodenal organoids that were cultured for >12 weeks, RNA was isolated with the RNeasy minikit (Qiagen) and quantified by optical density. cDNA was synthesized from 1 μg of RNA by performing a reverse-transcription PCR (Invitrogen). From murine small intestinal organoids that were cultured for >6 weeks, RNA was isolated using Trizol (Invitrogen) and quantified by optical density. cDNA was generated from 500 ng by the iScript™ cDNA synthesis kit (Bio Rad). Messenger RNA (mRNA) levels of human CFTR and mouse Cftr were determined by quantitative real-time RT-PCR with the SYBR Green method (Bio-Rad). Glyceraldehyde-3-phosphate dehydrogenase (GADPH) or p2M mRNA abundance was used to measure cDNA input.

Western Blot Analysis

For CFTR protein detection, HC or CF organoids were lysed in Laemmli buffer supplemented with complete protease inhibitor tablets (Roche). Lysates were analyzed by SDS-PAGE and electrophoretically transferred to a polyvinylidene difluoride membrane (Millipore). The membrane was blocked with 5% milk protein in TBST (0.3% Tween, 10 mM Tris pH8 and 150 mM NaCl in $H_2O$) and probed overnight at 4° C. with a combination of the mouse monoclonal anti-CFTR antibodies 450, 769 and 596 (1:5000, Cystic Fibrosis Folding consortium), followed by incubation with HRP-conjugated secondary antibodies and ECL development. For CFTR deglycosylation, HC organoids were lysed in RIPA buffer (50 mM Tris pH 8.0, 150 mM NaCl, 0.1% SDS, 0.5% sodium deoxycholate and 1% triton) supplemented with complete protease inhibitor tablets and incubated with PNGase F and Endo H for 3h at 33° C. (both from New England BioLabs).

Immunocytochemistry

Complete organoids from a 5-day culture were incubated with methanol (sigma) for 10 minutes at −20° C. Organoids were probed with the mouse monoclonal anti-CFTR antibody M3A7 (1:25; from Abcam) for 16 hours at 4° C., followed by simultaneous incubation of alexa fluor 649-conjugated secondary antibodies (1:500; from Sigma) and phalloidin-FITC for 1 hour at 4° C. (1:200; from Sigma). Organoids were embedded in Mowiol containing DAPI (1:10000) and analyzed by confocal microscopy as described previously[51].

Intestinal Current Measurement (ICM)

Transepithelial chloride secretion in human rectal suction biopsies (4 per subject) was measured as described previously using a recent amendment (repetitive prewashing)[3] which better accentuates forskolin-induced anion current responses by reducing basal cAMP levels. In short, the biopsies were collected in phosphate-buffered saline on ice and directly mounted in adapted micro-Ussing chambers (aperture 1.13 or 1.77 $mm^2$). After equilibration, the following compounds were added in a standardized order to the mucosal (M) or serosal (S) side of the tissue: amiloride (0.01 mM, M), to inhibit amiloride sensitive electrogenic $Na^+$ absorption; carbachol (0.1 mM, S), to initiate the cholinergic $Ca^{2+}$—and protein kinase C-linked $Cl^-$ secretion; DIDS (0.2 mM, M), to inhibit DIDS-sensitive, non-CFTR $Cl^-$ channels like the $Ca^{2+}$-dependent $Cl^-$ channels (CaCCs); histamine (0.5 mM, S), to reactivate the $Ca^2$-dependent secretory pathway and to measure the DIDS-insensitive component of $Ca^{2+}$-dependent $Cl^-$ secretion; forskolin (0.01 mM, S), to fully activate CFTR-mediated anion secretion. Crude Isc values (μA) were converted to $μA/cm^2$ based on the surface area of the aperture.

REFERENCES FOR EXAMPLE 2

1. Riordan, J. R. et al. Identification of the cystic fibrosis gene: cloning and characterization of complementary DNA. *Science* 245, 1066-1073 (1989).
2. Rommens, J. M. et al. Identification of the cystic fibrosis gene: chromosome walking and jumping. *Science* 245, 1059-1065 (1989).
3. Kerem, B. et al. Identification of the cystic fibrosis gene: genetic analysis. *Science* 245, 1073-1080 (1989).
4. Ratjen, F. & Döring, G. Cystic fibrosis. *Lancet* 361, 681-689 (2003).
5. Cheng, S. H. et al. Defective intracellular transport and processing of CFTR is the molecular basis of most cystic fibrosis. *Cell* 63, 827-834 (1990).
6. Riordan, J. R. CFTR function and prospects for therapy. *Annu. Rev. Biochem.* 77, 701-726 (2008).
7. Clancy, J. P. & Jain, M. Personalized medicine in cystic fibrosis: dawning of a new era. *Am. J. Respir. Crit. Care Med.* 186, 593-597 (2012).
8. Ramsey, B. W. et al. A CFTR potentiator in patients with cystic fibrosis and the G551D mutation. *N. Engl. J. Med.* 365, 1663-1672 (2011).
9. Van Goor, F. et al. Rescue of CF airway epithelial cell function in vitro by a CFTR potentiator, VX-770. *Proc. Natl. Acad. Sci. U.S.A.* 106, 18825-18830 (2009).
10. Rabeh, W. M. et al. Correction of both NBD1 energetics and domain interface is required to restore ΔF508 CFTR folding and function. *Cell* 148, 150-163 (2012).
11. Welch, E. M. et al. PTC124 targets genetic disorders caused by nonsense mutations. *Nature* 447, 87-91 (2007).
12. Sermet-Gaudelus, I. et al. Ataluren (PTC124) induces cystic fibrosis transmembrane conductance regulator protein expression and activity in children with nonsense mutation cystic fibrosis. *Am. J. Respir. Crit. Care Med.* 182, 1262-1272 (2010).
13. Clancy, J. P. et al. Results of a phase IIa study of VX-809, an investigational CFTR corrector compound, in subjects with cystic fibrosis homozygous for the F508del-CFTR mutation. *Thorax* 67, 12-18 (2011)
14. Flume, P. A. et al. Ivacaftor in subjects with cystic fibrosis who are homozygous for the F508del-CFTR mutation. *Chest* 142, 718-724 (2012).
15. Sato, T. et al. Single Lgr5 stem cells build crypt-villus structures in vitro without a mesenchymal niche. *Nature* 459, 262-265 (2009).
16. Sato, T. et al. Long-term expansion of epithelial organoids from human colon, adenoma, adenocarcinoma, and Barrett's epithelium. *Gastroenterology* 141, 1762-1772 (2011)
17. Sato, T. et al. Paneth cells constitute the niche for Lgr5 stem cells in intestinal crypts. *Nature* 469, 415-418 (2011).
18. Field, M. Intestinal ion transport and the pathophysiology of diarrhea. *J. Clin. Invest.* 111, 931-943 (2003).
19. Venkatasubramanian, J., Ao, M. & Rao, M. C. Ion transport in the small intestine. *Curr. Opin. Gastroenterol.* 26, 123-128 (2010).
20. Currid, A., Ortega, B. & Valverde, M. A. Chloride secretion in a morphologically differentiated human colonic cell line that expresses the epithelial Na+ channel. *J. Physiol. (Lond.)* 555, 241-250 (2004).

21. Cunningham, S. A., Worrell, R. T., Benos, D. J. & Frizzell, R. A. cAMP-stimulated ion currents in Xenopus oocytes expressing CFTR cRNA. *Am. J. Physiol.* 262, $C_{783}$-788 (1992).
22. Thiagarajah, J. R., Song, Y., Haggie, P. M. & Verkman, A. S. A small molecule CFTR inhibitor produces cystic fibrosis-like submucosal gland fluid secretions in normal airways. *FASEB J.* 18, 875-877 (2004).
23. Muanprasat, C. et al. Discovery of glycine hydrazide pore-occluding CFTR inhibitors: mechanism, structure-activity analysis, and in vivo efficacy. *J. Gen. Physiol.* 124, 125-137 (2004).
24. Ratcliff, R. et al. Production of a severe cystic fibrosis mutation in mice by gene targeting. *Nat. Genet.* 4, 35-41 (1993).
25. French, P. J. et al. A delta F508 mutation in mouse cystic fibrosis transmembrane conductance regulator results in a temperature-sensitive processing defect in vivo. *J. Clin. Invest.* 98, 1304-1312 (1996).
26. Wilke, M. et al. Mouse models of cystic fibrosis: phenotypic analysis and research applications. *J. Cyst. Fibros.* 10 Suppl 2, S152-71 (2011).
27. Denning, G. M. et al. Processing of mutant cystic fibrosis transmembrane conductance regulator is temperature-sensitive. *Nature* 358, 761-764 (1992).
28. Loo, T. W., Bartlett, M. C. & Clarke, D. M. Rescue of DeltaF508 and other misprocessed CFTR mutants by a novel quinazoline compound. *Mol. Pharm.* 2, 407-413 (2005).
29. Pedemonte, N. et al. Small-molecule correctors of defective DeltaF508-CFTR cellular processing identified by high-throughput screening. *J. Clin. Invest.* 115, 2564-2571 (2005).
30. Strandvik, B. et al. Spectrum of mutations in the CFTR gene of patients with classical and atypical forms of cystic fibrosis from southwestern Sweden: identification of 12 novel mutations. *Genet. Test.* 5, 235-242 (2001).
31. Kerem, B. S. et al. Identification of mutations in regions corresponding to the two putative nucleotide (ATP)-binding folds of the cystic fibrosis gene. *Proc. Natd. Acad. Sci. U.S.A.* 87, 8447-8451 (1990).
32. Zielenski, J. Genotype and phenotype in cystic fibrosis. *Respiration* 67, 117-133 (2000).
33. Hermans, C. J., Veeze, H. J., Drexhage, V. R., Halley, D. J. & van den Ouweland, A. M. Identification of the L927P and delta L1260 mutations in the CFTR gene. *Hum. Mol. Genet.* 3, 1199-1200 (1994).
34. de Jonge, H. R. et al. Ex vivo CF diagnosis by intestinal current measurements (ICM) in small aperture, circulating Ussing chambers. *J. Cyst. Fibros.* 3 Suppl 2, 159-163 (2004).
35. De Boeck, K. et al. New clinical diagnostic procedures for cystic fibrosis in Europe. *J. Cyst. Fibros.* 10 Suppl 2, S53-66 (2011).
36. Van Goor, F. et al. Correction of the $F5O_8$del-CFTR protein processing defect in vitro by the investigational drug VX-809. *Proc. Natl. Acad. Sci. U.S.A.* 108, 18843-18848 (2011).
37. Liu, J., Walker, N. M., Cook, M. T., Ootani, A. & Clarke, L. L. Functional Cftr in crypt epithelium of organotypic enteroid cultures from murine small Intestine. *Am. J. Physiol., Cell Physiol.* 302, $C_{1492}$-1503 (2012)
38. Li, H., Yang, W., Mendes, F., Amaral, M. D. & Sheppard, D. N. Impact of the cystic fibrosis mutation F508del-CFTR on renal cyst formation and growth. *Am. J. Physiol. Renal Physiol.* 303, F1176-1186(2012).
39. Gee, H. Y., Noh, S. H., Tang, B. L., Kim, K. H. & Lee, M. G. Rescue of ΔF508-CFTR trafficking via a GRASP-dependent unconventional secretion pathway. *Cell* 146, 746-760 (2011).
40. Luo, Y., McDonald, K. & Hanrahan, J. W. Trafficking of immature DeltaF508-CFTR to the plasma membrane and its detection by biotinylation. *Biochem. J.* 419, 211-9-2 p following 219 (2009).
41. Rennolds, J., Boyaka, P. N., Bellis, S. L. & Cormet-Boyaka, E. Low temperature induces the delivery of mature and immature CFTR to the plasma membrane. *Biochem. Biophys. Res. Commun.* 366, 1025-1029 (2008).
42. Chen, E. Y. T., Yang, N., Quinton. P. M. & Chin, W.-C. A new role for bicarbonate in mucus formation. *Am. J. Physiol. Lung Cell Mol. Physiol.* 299, L542-549 (2010).
43. Geborek, A. & Hjelte, L. Association between genotype and pulmonary phenotype in cystic fibrosis patients with severe mutations. *J. Cyst. Fibros.* 10, 187-192 (2011).
44. Sullivan, L. P., Wallace, D. P. & Grantham, J. J. Coupling of cell volume and membrane potential changes to fluid secretion in a model of renal cysts. *Kidney Int.* 45, 1369-1380 (1994).
45. Smith, J. J. & Welsh, M. J. Fluid and electrolyte transport by cultured human airway epithelia. *J. Clin. Invest.* 91, 1590-1597 (1993).
46. Roth, E. K. et al. The K+ channel opener 1-EBIO potentiates residual function of mutant CFTR in rectal biopsies from cystic fibrosis patients. *PLoS ONE* 6, e24445 (2011).
47. Wong, A. P. et al. Directed differentiation of human pluripotent stem cells into mature airway epithelia expressing functional CFTRTR protein. *Nat. Biotechnol.* 30, 876-882 (2012).
48. Thiagarajah, J. R. & Verkman, A. S. CFTR inhibitors for treating diarrheal disease. *Clin. Pharmacol. Ther.* 92, 287-290 (2012).
49. de Lau, W. et al. Lgr5 homologues associate with Wnt receptors and mediate R-spondin signalling. *Nature* 476, 293-297 (2011).
50. Korinek, V. et al. Constitutive transcriptional activation by a beta-catenin-Tcf complex in APC-/- colon carcinoma. *Science* 275, 1784-1787 (1997).
51. Beekman, J. M. et al. Syntenin-mediated regulation of Sox4 proteasomal degradation modulates transcriptional output. *Oncogene* 31, 2668-2679 (2012)

Further Observations

Further observation 1. Murine wild-type organoids show rapid swelling upon forskolin treatment.

Further observation 2. Forskolin-induced swelling is absent in organoids derived from CFTR-deficient mice.

Further observation 3. Organoids of F508del-CFTR expressing mice display low but detectable FIS, suggesting residual CFTR activity.

Further observation 4. Human healthy control organoids show rapid swelling upon forskolin treatment.

Further observation 5. Forskolin-induced swelling in organoids derived from a CF patient with a mild genotype (F508del/A455E).

Further observation 6. Low FIS is observed in organoids derived from a F508del homozygous patient.

Further observation 7. No FIS is detected in rectal organoids derived from a E60X/4015ATTTdel patient.

Further observations 8-16. Restoration of FIS in rectal F508del homozygous organoids by VRT-325 (8), Corr-4a (9), $C_8$ (10), VX-809 (11), VX-770 (12), VRT-325+Corr-4a (13), C₈+Corr-4a (14), VX-809+VX-770 (15) or VX-809+ VX-770 and CFTR inhibition (16).

Example 3

Cystic fibrosis transmembrane conductance regulator (CFTR) functions as anion channel, and is essential for fluid and electrolyte homeostasis at epithelial surfaces of many organs, including lung and intestine. The autosomal-recessive disorder cystic fibrosis (CF) is caused by mutations of the CFTR gene. CF disease is highly variable, and patients have a median life expectancy of approximately 40 years. Loss-of-function mutations cause altered ion and fluid transport that results in accumulation of viscous mucus in the pulmonary and gastrointestinal tract. This is associated with bacterial infections, aberrant inflammation and malnutrition. Over 1500 mutations have been described, but the most dominant mutation (~67% of total mutant alleles worldwide) is a deletion of phenylalanine at position 508 (CFTR-delF508). This causes misfolding, ER-retention and early degradation of the CFTR protein which prevents function at the plasma membrane. Other mutations in the CFTR gene that have been found in CF patients also impair protein folding or impair protein production, gating, conductance, splicing and/or interactions with other proteins {Riordan: 2008dp}.

Current therapy for CF is mainly symptomatic and focuses on reduction of bacterial pressure, inflammation, and normalization of nutrient uptake and physical growth. Recently, multiple compounds have been identified that target mutation-specific defects of the CFTR protein itself (Accurso:2010jx, Clancy:2011ic). Clinical trials are currently performed using compounds that induce i) premature stopcodon readthrough, ii) correction of plasmamembrane trafficking of CFTR (correctors), and iii) enhance CFTR gating (potentiators) {Rogan:2011es}. Recently, a phase III clinical trial has successfully been completed for a potentiator in CF patients with a CFTR-G551D mutation, demonstrating that mutation-specific drug targeting is feasible in CF {Shah:2011gu}. Combinations of correctors and potentiators are currently assessed in a phase II trial for the dominant patient-group harboring the CFTR-delF508 mutation.

Although these recent developments are very promising, the level of functional restoration of CFTR by these drugs in in vitro model systems is still limited. In addition, patients show variable responses to these therapies due to yet undefined mechanisms. The inability to select these non-responding subgroups limits clinical efficacy and drug registration. Together, this indicates that development of new compounds and screening of drug efficacy at the level of individual patients are urgently needed. Thus far, there are only limited primary cell models available to screen for compounds that restore mutant CFTR function. When such an in vitro model can be further expanded to allow analysis of drug responses of individual patients, it may improve drug efficacy by selecting subgroups of responding patients.

We here demonstrate a rapid, quantitative assay for CFTR function in a murine and human primary intestinal crypt-based culture method. This culture method enables intestinal stem cells to expand into closed organoids containing crypt-like structures and an internal lumen {Sato:2011fy, Sato:2009jg}. Intestinal CFTR is predominantly expressed at the apical membrane of the crypt cells where its activation drives secretion of electrolytes and fluids {Venkatasubramanian:2010jc, Currid:2004ck}. In this study, we assessed whether forskolin, which raises intracellular cAMP and thereby activates CFTR, could mediate fluid-transport into the organoid lumen. Using live cell microscopy, we observed a rapid expansion of the lumen, and total organoid surface area when forskolin was added, while DMSO-treated organoids were unaffected (FIG. 25A). This forskolin-induced swelling (FIS) of organoids was reversed upon removal of forskolin by washing (FIG. 29). High levels of CFTR mRNA in these organoids further supported a possible role for CFTR in FIS of organoids (FIG. 30).

Next, we quantified these responses by unbiased image analysis. We found excellent cell labelling whilst background levels of the surrounding matrigel remained negative using calcein-green, a cell-permeable dye that upon metabolic conversion by living cells gains fluorescence and is retained within the cell. We quantified FIS of individual organoids using live cell confocal microscopy and imaging software that calculated the surface area of the fluorescent object for each time point upon forskolin addition (FIGS. 25B and 25C). Multiple organoids in a single well were simultaneously stimulated and analysed (FIG. 25D). We observed a dose-dependent relation between forskolin and increase of surface area in time (FIG. 25D). FIS of murine organoids is shown for the first 10 minutes, as some wild type organoids collapsed when stimulations up to 30 minutes were performed (FIG. 31A). Together, these results show that forskolin-induced organoid expansion can be quantified by unbiased fluorescent image analysis.

To demonstrate a role for CFTR in forskolin-induced swelling, we used chemical inhibitors of CFTR, and CFTR-delF508 mutant as well as CFTR knockout mice (French: 1996hb, Ratcliff:1993ik). Pre-incubation with the CFTR inhibitors CFTRinh-172 {Thiagarajah:2004ck} and GlyH-101 {Muanprasat:2004fx} independently reduced FIS by ~80% compared to vehicle treatment (FIG. 26A). Their combined action fully prevented FIS at the time points analysed. We further confirmed CFTR-dependent FIS using organoids isolated from CFTR-deficient mice. FIS was completely absent when organoids of CFTR-deficient mice were assayed (FIGS. 26B and 26C). Calcein green labelling was similar indicating that CFTR-deficient cells were viable. Absolute sizes of the selected organoids at the start of the experiments were not different (FIGS. 26D and 26G). Organoids of CFTR-delF508 expressing mice displayed low but detectable FIS, suggesting residual CFTR activity, consistent with earlier observations in this mouse model {French, 1996, Wilke 2011} and in a subcategory of F508del CFTR patients {Bronsveld/Veeze}(FIGS. 26E and 26F). In support of this, the FIS in CFTR-delF508 mice is partially sensitive to CFTRinh-172 (FIG. 26H).

To further indicate that our assay is sensitive to correction of CFTR function, we performed temperature-rescue experiments, a widely accepted method to increase CFTR-delF508 function {Denning:1992hs}. CFTR-delF508 misfolding is reduced at 27° C. leading to enhanced levels of functional CFTR at the plasma membrane. We observed increased levels of FIS upon overnight incubation at 27° C. (FIG. 26H). Although FIS of CFTR-delF508 organoids under these conditions reaches levels comparable to wild type organoids, organoid collapse within 30 minutes rarely occurs (FIG. 31B). Chemical inhibition of CFTR activity severely reduced FIS in organoids grown at reduced and normal temperature (FIG. 26H). Collectively, these results demonstrated that FIS in murine organoids is fully CFTR dependent, and is sensitive to detect increased function of CFTR-delF508 by a standard correction approach described in literature.

We next applied our assay conditions to human organoid cultures. Culture conditions for human and mouse organoids differ significantly, leading to a cyst-like phenotype of human organoids when compared to mouse organoids (FIG. 27A, left panel). This cyst-like phenotype results from high amounts of Wnt3a in the standard culture medium {Barker: 2010cp, Sato:2011fy}. We observed that organoids reshape to a budding phenotype when cultured under low Wnt3a concentrations (FIG. 27A, right panel), a condition that prevents long-term expansion of the organoid culture, but does not immediately affect cell viability. We stimulated organoids cultured at high (FIGS. 27B and 27C) and low (FIGS. 27B and 27D) Wnt3a concentrations with forskolin, and observed larger FIS at low Wnt3a conditions, reaching levels comparable to murine organoids. In contrast to murine organoids, human organoid do hardly collide during FIS within 40 minutes (FIG. 31C). In both high and low Wnt3a conditions, FIS was fully inhibited by CFTR inhibitors. These data indicate that the FIS in human organoids is mediated by CFTR.

Next, we assayed human organoids derived from a homozygous F508del CFTR patient. No forskolin-induced swelling was observed in CF organoids (FIG. 28A). However, FIS was induced in CF organoids upon treatment with CFTR correctors VRT-325 and corr-4a (FIG. 28B). This further indicated that FIS in human organoids is CFTR dependent, and that our assay can be used to measure drugs that impact CFTR F508del function.

Collectively, our results indicate that forskolin-induced swelling of both mouse and human small intestinal organoid structures is CFTR-dependent. Our newly developed assay to measure CFTR-activity could be further developed for CF diagnosis and to perform high throughput screens to identify novel compounds that restore CFTR function. Furthermore, this assay may be suitable for development of drugs to treat secretory diarrhoea, a life threatening condition that results from CFTR hyper-activation by pathogenic toxins, and for electrolyte homeostasis studies in general. Swollen organoids reverse to normal phenotype upon forskolin washing (FIG. 29) and could therefore be possibly used as model for intestinal (re)absorption.

Two important aspects of organoid cultures render them highly suitable for follow up studies. Firstly, organoids can be greatly expanded while maintaining stemness during long term culture (over >30 passages). Generation of large cell numbers is required to generate insight into CFTR-dependent cellular alterations at the systems biology level, and a prerequisite for high throughput screens. Secondly, organoids can be stored in liquid nitrogen, allowing generation of primary cell banks of CF patients. These can be used to identify and study cellular factors associated with clinical phenotypes in CF patients. Another exciting possibility would be to use our in vitro assay to predict in vivo drug-responsiveness at the level of individual patients, and may be especially suited for drugs that target mutant CFTR directly. This may facilitate the development of drugs and the approval of drugs to which only subgroups of patients respond.

METHODS

Mice $Cftr^{tm1Cam}$ knockout mice (CFTR−/−) {Ratcliff:1993ik} were back-crossed with FVB mice and $Cftr^{tm1eur}$ (CFTR-delF508) {French:1996hb} were back-crossed with C57Bl/6 (F12) mice. Congenic FVB CFTR−/− mice or $C_{57}Bl/6$ CFTR-delF508 mice were used with their wild type littermates. The mice were maintained in an environmentally controlled facility at the Erasmus Medical Center Rotterdam and approved by the local Ethical Committee.

Patient Material

Two biopsies of 3-5 mm diameter were obtained from the bulbus and the pars horizontalis of the duodenum from a patient with suspected celiac disease by using flexible gastroduodenoscopy. The biopsies were macroscopically and pathologically normal. Approval for this study was obtained by the local Ethics Committee.

Crypt Isolation and Organoid Culture from Murine Intestine

Murine organoids were generated from isolated small intestinal (SI) crypts and maintained in culture as described previously {Sato:2009jg}. Rspo1-conditioned medium (cells were kindly provided by A. Ootani) was used instead of recombinant Rspo-1 and added to the culture medium at a 1:10 dilution. CFTR−/− and CFTR-delF508 organoids were obtained from proximal and distal SI segments, respectively. Organoids from passage 1-9 were used for confocal imaging.

Crypt Isolation and Organoid Culture from Human Biopsies

Crypt isolation and culture of human intestinal cells have been described previously (Sato, gastro 2011). In short, biopsies were washed with cold complete chelation solution and incubated with 10 mM EDTA for 5-15 min at 4° C. Supernatant was harvested and EDTA was washed away. Crypts were isolated by spinning and embedded in matrigel (growth factor reduced, phenol-free, BD bioscience) and seeded (500 crypts per 50 μl matrigel per well) in 24-well plates. The matrigel was polymerized for 10 min at 37° C. and immersed in complete culture medium: advanced DMEM/F12 supplemented with penicillin/streptomycin, 10 mM HEPES, Glutamax, N2, B27 (all from Invitrogen), 1 μM M-acetylcysteine (Sigma) and growth factors: 50 ng/ml mEGF, 50% Wnt3a-conditioned medium and 10% Noggin-conditioned medium (both kindly provided by the lab of Dr. H. Clevers), 20% Rspo1-conditioned medium, 10 μM Nicotinamide (Sigma), 10 nM Gastrin (Sigma), 500 nM A83-01 (Tocris) and 10 μM SB202190 (Sigma). The medium was refreshed every 2-3 days and organoids were passaged 1:4 every 7-10 days. From passage 6 onwards, the organoids were cultured with normal (50%) or reduced (5%) amounts of Wnt3a-conditioned medium for 5 days. Organoids from passage 6 and 7 were used for confocal live cell imaging.

Stimulation Assays

Human or mouse organoids from a 7 day-old culture were seeded in a flat-bottom 96-wells culture plate (Nunc) in 5 μl matrigel containing 10-40 organoids and 100 μl normal culture medium. One or two days after seeding, organoids were incubated for 60 minutes with 100 μl staining medium (advanced DMEM/F12 supplemented with penicillin/streptomycin, 10 mM HEPES and Glutamax) containing 10 μM calcein-green (Invitrogen). For CFTR inhibition, organoids were simultaneously incubated for 60 minutes with 10 μM calcein-green and 50 μM CFTRinh-172 (Sigma), 50 μM GlyH-101 (Calbiochem) or combined treatment of 50 μM CFTRinh-172 and 50 µM GlyH-101. After 60 minutes of calcein-green treatment (with or without CFTR inhibition), of 5 µM forskolinb was added and organoids were directly analyzed by confocal live cell microscopy (LSM710, Zeiss, 5× objective). Organoid surface area was calculated by Volocity imaging software.

RNA Isolation and qPCR

From human duodenal organoids that were cultured for >12 weeks, RNA was isolated with the RNeasy minikit (Qiagen) and quantified by optical density. cDNA was synthesized from 1 Mg of RNA by performing a reverse-transcription PCR (Invitrogen). From murine small intestinal organoids that were cultured for >6 weeks, RNA was isolated using Trizol (Invitrogen) and quantified by optical density. cDNA was generated from 500 Mg by the iScript™ cDNA synthesis kit (Bio Rad). Messenger RNA (mRNA) levels of human and mouse CFTR were determined by quantitative real-time RT-PCR with the SYBR Green method (Bio-Rad). Glyceraldehyde-3-phosphate dehydrogenase (GADPH) or P2M mRNA abundance was used to indicate cDNA input.

REFERENCES FOR TABLE 3

1 Ma, T., J. R. Thiagarajah, H. Yang, N. D. Sonawane, C. Folli, L. J. V. Galietta and A. S. Verkman. 2002. Thiazolidinone CFTR inhibitor identified by high-throughput screening blocks cholera toxin-induced intestinal fluid secretion. J. Clin. Invest. 110(11):1651-1658.

2 Muanprasat, C., N. D. Sonawane, D. Salinas, A. Taddei, L. J. V. Galietta and A. S. Verkman. 2004. Discovery of glycine hydrazide pore-occluding CFTR inhibitors: Mechanism, structure-activity analysis, and in vivo efficacy. J. Gen. Physiol. 124:125-137.

3 Singh, A. K., B. D. Schultz, W. van Driessche and R. J. Bridges. 2004. Transepithelial fluctuation analysis of chloride secretion. J. Cyst. Fibros. 3 Suppl 2:127-132.

4 Pedemonte, N., N. D. Sonawane, A. Taddei, J. Hu, O. Zegarra-Moran, Y. F. Suen, L. I. Robins, C. W. Dicus, D. Willenbring, M. H. Nantz, M. J. Kurth, L. J. Galietta and A. S. Verkman. 2005. Phenylglycine and sulfonamide correctors of defective delta F508 and G551D cystic fibrosis transmembrane conductance regulator chloride-channel gating. Mol. Pharmacol. 67(5):1797-1807.

5. Caci, E., C. Folli, O. Zegarra-Moran, T. Ma, M. F. Springsteel, R. E. Sammelson, M. H. Nantz, M. J. Kurth, A. S. Verkman and L. J. V. Galietta. 2003. CFTR activation in human bronchial epithelial cells by novel benzoflavone and benzimidazolone compounds. Am. J. Physiol. Lung Cell. Mol. Physiol. 285:L180-L188.

6 Yang, H., A. A. Shelat, R. K. Guy, V. S. Gopinath, T. Ma, K. Du, G. L. Lukacs, A. Taddei, C. Folli, N. Pedemonte Y, L. J. V. Galietta and A. S. Verkman. 2003. Nanomolar affinity small molecule correctors of defective DF508-CFTR chloride channel gating. J. Biol. Chem. 278(37): 35079-35085.

7 Ma, T., L. Vetrivel, H. Yang, N. Pedemonte, O. Zegarra-Moran, L. J. V. Galietta and A. S. Verkman. 2002. High-affinity activators of cystic fibrosis transmembrane conductance regulator (CFTR) chloride conductance identified by high-throughput screening. J. Biol. Chem. 277(40):37235-37241.

8 Devor, D. C., R. J. Bridges and J. M. Pilewski. 2000. Pharmacological modulation of ion transport across wild-type and DeltaF508 CFTR-expressing human bronchial epithelia. Am. J. Physiol. Cell Physiol. 279(2):C461-C479

9 Springsteel, M. F., L. J. V. Galietta, T. Ma, K. By, G. O. Berger, H. Yang, C. W. Dicus, W. Choung, C. Quan, A. Shelat, R. K. Guy, A. S. Verkman, M. J. Kurth and M. H. Nantz. 2003. Benzoflavone activators of the cystic fibrosis transmembrane conductance regulator: Towards a pharmacophore model for the nucleotide-binding domain. Bioorg. Med. Chem. 11:4113-4120.

10 Sammelson, R. E., T. Ma, L. J. V. Galietta, A. S. Verkman and M. J. Kurth. 2003. 3-(2-Benzyloxyphenyl)isoxazoles and isoxazolines: Synthesis and evaluation as CFTR activators. Bioorg. Med. Chem. Lett. 13:2509-2512

11 Pedemonte, N., G. L. Lukacs, K. Du, E. Caci, O. Zegarra-Moran, L. J. V. Galietta and A. S. Verkman. 2005. Small-molecule correctors of defective DF508-CFTR cellular processing identified by high-throughput screening. J. Clin. Invest. 115(9):2564-2571.

12 Van Goor, F., K. S. Straley, D. Cao, J. Gonzalez, S. Hadida, A. Hazlewood, J. Joubran, T. Knapp, L. R. V Makings, M. Miller, T. Neuberger, E. Olson, V. Panchenko, J. Rader, A. Singh, J. H. Stack, R. Tung, P. D. Grootenhuis and P. Negulescu. 2006. Rescue of {Delta}F508 CFTR trafficking and gating in human cystic fibrosis airway primary cultures by small molecules. Am. J. Physiol. Lung Cell Mol. Physiol. Epub 13 Loo, T. W., M. C. Bartlett, Y. Wang and D. M. Clarke. 2006. The chemical chaperone CFcor-325 repairs folding defects in the transmembrane domains of CFTR processing mutants. Biochem. J. Epub.

14 Makings, Lewis R.; Singh, Ashvani K.; Miller, Mark T.; Hadida Ruah, Sarah S.; Grootenhuis, Peter; Hamilton, Matthew; Hazelwood, Anna R.; Huang, Liming. Preparation of pyrimidine derivatives as modulators of ATP-binding cassette transporters. PCT Int. Appl. (2004), WO 20041111014 A1

15. Vangoor, Frederick F.; Hadida Ruah, Sarah S.; Singh, Ashvani K.; Olson, Eric R.; Makings, Lewis R.; Gonzalez, Jesus E., Ill; Rader, James A.; Chambers, Fred, Ill; Miller, Mark T.; Grootenhuis, Peter; Liu, Yahua. Preparation of substituted pyrazoles as modulators of ATP-binding cassette transporters. PCT Int. Appl. (2004) WO 2004080972 A1

16 Routaboul, Christel; Norez, Caroline; Melin, Patricia; Molina, Mare-Carmen; Boucherle, Benjamin; Bossard, Florian; Noel, Sabrina; Robert, Renaud; Gauthier, Chantal; Becq, Frederic; Décout, Jean-Luc. 2007. Discovery of a-Aminoazaheterocycle-Methylglyoxal adducts as a new class of high-affinity inhibitors of Cystic Fibrosis trans-membrane conductance regulator chloride channels. J. Pharmacol. Exp. Ther. 322(3):1023-1035.

17 Sonawane, N. D., Zegarra-Moran, O., Namkung, W., Galietta, L., and Verkman, A. S. 2008. a-Aminoazaheterocyclic-methylglyoxal adducts do not inhibit CFTR chloride channel activity. J. Pharmacol. Exp. Ther. Epub.

18 Robert, R., Carlile, G. W., Pavel, C., Liu, N., Anjos, S. M., Liao, J., Luo, Y., Zhang, D., Thomas, D. Y., and Hanrahan, J. W. 2008. Structural analog of sildenafil identified as a novel corrector of the F508del-CFTR trafficking defect. Mol. Pharmacol. 73(2):478-489.

19 Macia, E., Ehrlich, M., Massol., R., Boucrot, E., Brunner, C., and Kirchhausen, T. 2006. Dynasore, a cell-permeable inhibitor of dynamin. *Dev. Cell.* 10(6):839-850.
20 Yoo, C. L., Yu, G. J., Yang, B., Robins, L. I., Verkman, A. S., and Kurth, M. J. 2008. 4'-Methyl-4,5'-bithiazole-based correctors of defective delta F508-CFTR cellular processing. *Bioorg. Med. Chem. Lett.* 18(8):2610-2614.
21 Hirth, B. H., Qiao, S., Cuff, L. M., Cochran, B. M., Pregel, M. J., Gregory, J. S., Sneddon, S. F., and Kane, J. L. Jr. 2005. Discovery of 1,2,3,4-tetrahydroisoquinoline-3-carboxylic acid diamides that increase CFTR mediated chloride transport. *Bioorg. Med. Chem. Lett.* 15(8):2087-2091.
22. Tradtrantip, L., N. D. Sonawane, W. Namkung, A. S., Verkman 2009. Nanomolar potency Pyrimido-pyrrolo-quinoxalinedione CFTR inhibitor reduces cyst size in a polycystic kidney disease model. *J. Med. Chem.* 52(20): 6447-55.
23. Sonawane, N. D., A. S., Verkman 2008. Thiazolidinone CFTR inhibitors reduces with improved water solubility identified by structure-activity analysis. *Bioorg. Med. Chem.* 16(17):8175-95
24. Vertex Patent WO 2007/021982 A2; Compound #12 page 15.

The invention claimed is:

1. An in vitro method for diagnosing polycystic kidney disease, wherein the method comprises
measuring swelling of one or more organoids generated from primary kidney cells derived from a subject,
wherein swelling means an increase in size of the one or more organoids due to fluid uptake,
and
wherein a larger size of said one or more organoids compared to a control organoid indicates the presence of polycystic kidney disease.

2. The method according to claim 1, wherein the method comprises stimulation of the one or more organoids with one or more drugs.

3. The method according to claim 1, wherein the change in size is compared to a healthy control organoid.

4. The method according to claim 1, wherein the organoids are generated from primary human kidney cells.

5. The method according to claim 1, wherein the method comprises generating the one or more organoids by expanding kidney stem cells into closed organoids which include a closed lumen on the apical membrane of the cells.

* * * * *